US012715869B2

(12) United States Patent
D'Agostino et al.

(10) Patent No.: US 12,715,869 B2
(45) Date of Patent: Aug. 25, 2026

(54) MODULATORS OF CAMKK2 AS LIGAND DIRECTED DEGRADERS

(71) Applicant: Celgene Corporation, Princeton, NJ (US)

(72) Inventors: Laura Akullian D'Agostino, Sudbury, MA (US); Brandon Whitefield, San Diego, CA (US); Young Chen, San Marcos, CA (US)

(73) Assignee: Celgene Corporation, Princeton, NJ (US)

( * ) Notice: Subject to any disclaimer, the term of this patent is extended or adjusted under 35 U.S.C. 154(b) by 310 days.

(21) Appl. No.: 18/694,691

(22) PCT Filed: Oct. 7, 2022

(86) PCT No.: PCT/US2022/046031
§ 371 (c)(1),
(2) Date: Mar. 22, 2024

(87) PCT Pub. No.: WO2023/059873
PCT Pub. Date: Apr. 13, 2023

(65) Prior Publication Data

US 2025/0145607 A1 May 8, 2025

Related U.S. Application Data

(60) Provisional application No. 63/253,721, filed on Oct. 8, 2021.

(51) Int. Cl.
*C07D 417/14* (2006.01)
*A61K 31/517* (2006.01)

(52) U.S. Cl.
CPC .......... *C07D 417/14* (2013.01); *A61K 31/517* (2013.01)

(58) Field of Classification Search
CPC .................................................... C07D 417/14
See application file for complete search history.

(56) References Cited

FOREIGN PATENT DOCUMENTS

WO 2022240826 A1 11/2022

OTHER PUBLICATIONS

Bricelj et al., "E3 Ligase Ligands in Successful PROTACs: An Overview of Syntheses and Linker Attachment Points," Front. Chem., 2021, 9:707317, 46 pages.
Eduful et al., "Hinge Binder Scaffold Hopping Identifies Potent Calcium/Calmodulin-Dependent Protein Kinase Kinase 2 (CAMKK2) Inhibitor Chemotypes," J. Med. Chem., 2021, 64:10849-10877.
International Search Report and Written Opinion received in PCT/US2022/046031, dated Feb. 2, 2023, 15 pages.

*Primary Examiner* — Golam M Shameem
(74) *Attorney, Agent, or Firm* — McNeill PLLC

(57) ABSTRACT

Provided herein are compounds of formula (I) and compositions thereof for modulating CAMKK2. In some embodiments, the compounds and compositions are provided for treatment of cancer and/or obesity.

(I)

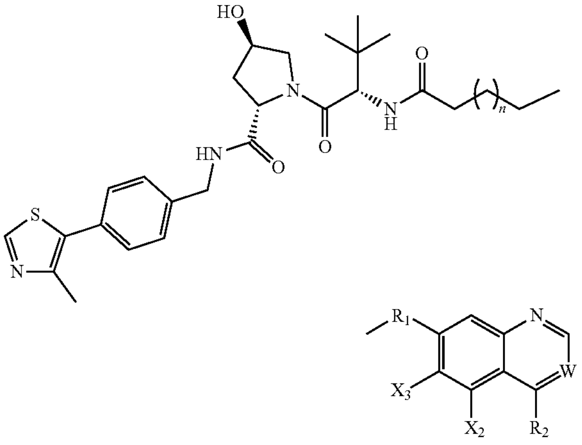

12 Claims, No Drawings

MODULATORS OF CAMKK2 AS LIGAND DIRECTED DEGRADERS

CROSS-REFERENCE TO RELATED APPLICATIONS

This application is a national stage entry pursuant to 35 U.S.C. § 371 of International Application No. PCT/US2022/046031, filed Oct. 7, 2022, which claims the benefit of priority of U.S. Provisional Application No. 63/253,721, filed Oct. 8, 2021, each of which is incorporated by reference herein in its entirety for any purpose.

FIELD

The present disclosure relates generally to compounds, compositions, and methods for their preparation and use of the compounds and compositions for treating cancer.

BACKGROUND

Tumor-associated myeloid cells play a pivotal role in the regulation of processes that control tumor growth and metastasis, and their accumulation in cancer tumors has been identified as an important negative prognostic factor. Calcium/calmodulin-dependent protein kinase kinase 2 (CAMKK2) has been shown to be highly expressed within intratumoral myeloid cells in mouse models of breast cancer, and its inhibition within myeloid cells suppresses tumor growth by increasing intratumoral accumulation of effector $CD8^+$ T cells and immune-stimulatory myeloid subsets (Racioppi et al., *Nat Commun.* 2019 Jun. 4; 10(1); 2450). Furthermore, depletion of CAMKK2 activity is associated with the accumulation of macrophages expressing high levels of the major histocompatibility molecule class II molecule I-A (MHC II I-A) and CD8+ T-cells within the tumor microenvironment (WO 2018/027223). Treatment with CAMKK2 inhibitors has been shown to block tumor growth and facilitate reprogramming of the microenvironment (WO 2018/027223). In human breast cancer biopsies, CAMKK2 expression levels correlate with tumor grade and in high-grade tumors, both tumor cells and tumor-associated macrophages express high levels of this enzyme (WO 2018/027223). These findings implicate CAMKK2 as a macrophage specific checkpoint, and demonstrate that CAMKK2 inhibition would be an innovative therapeutic strategy for treating cancer through reprogramming the tumor microenvironment.

In addition to cancer treatment, CAMKK2 inhibition promotes weight loss, which could have significant medical and social benefits. CAMKK2-null mice show a sustained reduction in feeding on a high-fat diet and have lower body weights, reduced adiposity, and improved glucose sensitivity relative to their wild-type littermates (Anderson et al., *Cell Metab.* 2008, 7, 377). From a mechanistic standpoint, CAMKK2-null mice are acutely resistant to ghrelin-induced food intake, and eat less than their wild-type counterparts upon refeeding after fasting, similar to neuropeptide Y (NPY)-depleted mice. These latter observations are corroborated by pharmacological inhibition of CAMKK2 using STO-609 delivered via intracerebroventricular administration (Anderson et al., *Cell Metab.* 2008, 7, 377), or using 2,4-diaryl 7-azaindoles delivered via oral administration (Price et al., *Bioorg. Med. Chem. Lett.* 2018 Jun. 1; 28(10): 1958-1963). Therefore, CAMKK2 is an attractive therapeutic target for the treatment of cancer and obesity.

Protein degradation is a highly regulated and essential process that maintains cellular homeostasis. Selective identification and removal of damaged, misfolded, or excess proteins is achieved through the ubiquitin-proteasome pathway (UPP). The UPP is central to the regulation of almost all cellular processes. Ubiquitination of the protein is accomplished by an E3 ubiquitin ligase that binds to a protein and adds ubiquitin molecules to the protein, thus marking the protein for proteasome degradation.

Harnessing the UPP for therapeutic use has received significant interest (Zhou et al., *Mol. Cell* 2000, 6, 751-756). One promising therapy uses proteolysis targeting chimeras, commonly referred to as PROTACs, to effect removal of unwanted proteins by protein degradation (Scheepstra et al., *Comp. Struct. Biotech. J.* 2019, 17, 160-176). PROTACS are ligand directed degraders that bring together an E3 ligase and a target protein that is to be degraded. These bivalent molecules usually consist of an E3 ligase ligand connected through a linker moiety to small molecule that binds to the target protein. A PROTAC positions the E3 ligase at the appropriate distance and orientation to the target protein, allowing the latter to be ubiquitinated. The ubiquitinated target protein is subsequently recognized by the proteasome, where it is degraded.

Accordingly, in one aspect, provided herein are compounds that target CAMKK2 for degradation.

SUMMARY

Described herein, in certain embodiments, are compounds and compositions thereof for degrading CAMKK2. In various embodiments, the compounds and compositions thereof may be used for treatment of cancer and/or obesity.

The present embodiments can be understood more fully by reference to the detailed description and examples, which are intended to exemplify non-limiting embodiments.

Embodiment 1 is a compound of Formula (I):

(I)

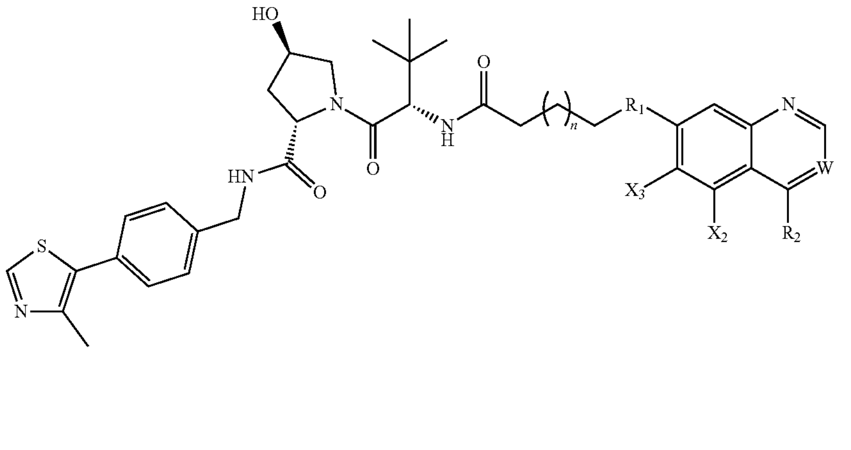

or a pharmaceutically acceptable salt thereof, wherein:

W is N or $CX_1$;

$R_1$ is O or optionally substituted heteroarylene;

$R_2$ is optionally substituted aryl;

$X_1$, $X_2$, and $X_3$ are independently hydrogen, halogen, or —CN; and n is 2-10.

Embodiment 2 is the compound of embodiment 1, or a pharmaceutically acceptable salt thereof, wherein:

$R_1$ is O.

Embodiment 3 is the compound of embodiment 1, or a pharmaceutically acceptable salt thereof, wherein:

$R_1$ is optionally substituted heteroarylene.

Embodiment 4 is the compound of embodiment 3, or a pharmaceutically acceptable salt thereof, wherein:

$R_1$ is pyrazolylene optionally substituted with methyl.

Embodiment 12 is the compound of any one of embodiments 1-10, or a pharmaceutically acceptable salt thereof, wherein:

W is $CX_1$.

Embodiment 13 is the compound of embodiment 12, or a pharmaceutically acceptable salt thereof, wherein:

$X_1$ is hydrogen or halogen.

Embodiment 14 is the compound of any one of embodiments 1-13, or a pharmaceutically acceptable salt thereof, wherein:

$X_2$ and $X_3$ are independently hydrogen or halogen.

Embodiment 15 is the compound of any one of embodiments 1-14, or a pharmaceutically acceptable salt thereof, wherein:

n is 4-9.

Embodiment 16 is the compound of claim 1, or a pharmaceutically acceptable salt thereof, wherein the compound is of Formula (Ia):

(Ia)

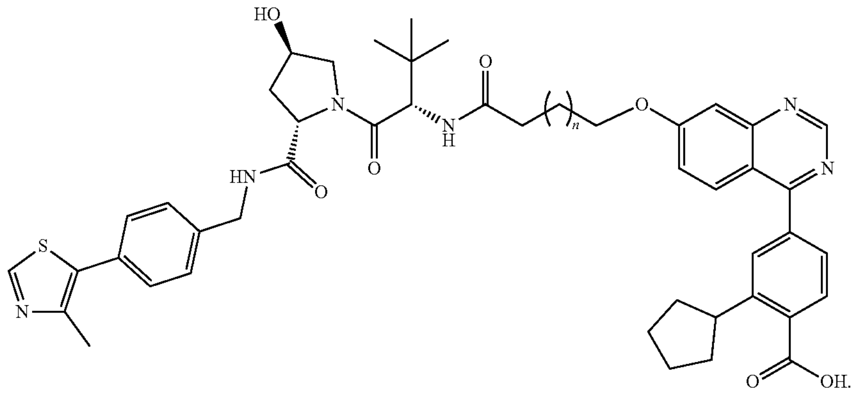

Embodiment 5 is the compound of any one of embodiments 1-4, or a pharmaceutically acceptable salt thereof, wherein:

$R_2$ is aryl optionally substituted by at least one substituent selected from alkyl, carbonyl, carbocyclyl, heterocyclyl, and heteroaryl.

Embodiment 6 is the compound of embodiment 5, or a pharmaceutically acceptable salt thereof, wherein:

$R_2$ is aryl optionally substituted by $C_1$-$C_3$ alkyl optionally substituted by halogen or $C_3$-$C_4$ carbocyclyl.

Embodiment 7 is the compound of embodiment 5, or a pharmaceutically acceptable salt thereof, wherein:

$R_2$ is aryl optionally substituted by —$CO_2H$ or —C(O)$NH_2$.

Embodiment 8 is the compound of embodiment 5, or a pharmaceutically acceptable salt thereof, wherein:

$R_2$ is aryl optionally substituted by $C_3$-$C_5$ carbocyclyl optionally substituted by halogen.

Embodiment 9 is the compound of embodiment 5, or a pharmaceutically acceptable salt thereof, wherein:

$R_2$ is aryl optionally substituted by a 6-membered heterocyclyl containing a nitrogen atom.

Embodiment 10 is the compound of embodiment 5, or a pharmaceutically acceptable salt thereof, wherein:

$R_2$ is aryl optionally substituted by tetrazolyl.

Embodiment 11 is the compound of any one of embodiments 1-10, or a pharmaceutically acceptable salt thereof, wherein:

W is N.

Embodiment 17 is the compound of embodiment 16, or a pharmaceutically acceptable salt thereof, wherein:

n is 4-9.

Embodiment 18 is the compound of embodiment 17, or a pharmaceutically acceptable salt thereof, wherein:

n is 4.

Embodiment 19 is the compound of embodiment 17, or a pharmaceutically acceptable salt thereof, wherein:

n is 5.

Embodiment 20 is the compound of embodiment 17, or a pharmaceutically acceptable salt thereof, wherein:

n is 6.

Embodiment 21 is the compound of embodiment 17, or a pharmaceutically acceptable salt thereof, wherein:

n is 7.

Embodiment 22 is the compound of embodiment 17, or a pharmaceutically acceptable salt thereof, wherein:

n is 8.

Embodiment 23 is the compound of embodiment 17, or a pharmaceutically acceptable salt thereof, wherein:

n is 9.

Embodiment 24 is a compound selected from the compounds of Table 1 or a pharmaceutically acceptable salt thereof.

Embodiment 25 is a pharmaceutical composition comprising the compound of any one of embodiments 1-24, or a pharmaceutically acceptable salt thereof, and a pharmaceutically acceptable excipient.

Embodiment 26 is a method of regulating gene transcription in a cell comprising modulating Calcium/calmodulin-dependent protein kinase kinase 2 (CAMKK2) activity by exposing CAMKK2 to the compound of any one of embodiments 1-24, or a pharmaceutically acceptable salt thereof, or the pharmaceutical composition of embodiment 25.

Embodiment 27 is a method of modulating calcium/calmodulin-dependent protein kinase kinase 2 (CAMKK2) comprising contacting CAMKK2 with an effective amount of the compound of any one of embodiments 1-24, or a pharmaceutically acceptable salt thereof, or the pharmaceutical composition of embodiment 25.

Embodiment 28 is a method of treating a cancer in a subject in need thereof, comprising administering to the subject an effective amount of the compound of any one of embodiments 1-24, or a pharmaceutically acceptable salt thereof, or the pharmaceutical composition of embodiment 25.

Embodiment 29 is the method of embodiment 28, wherein the cancer is acute myeloid leukemia (AML), acute lymphoblastic leukemia (ALL), small cell lung cancer (SCLC), non-small cell lung cancer (NSCLC), neuroblastoma, small round blue cell tumors, glioblastoma, glioma, prostate cancer, breast cancer, bladder cancer, lung cancer, or melanoma.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean ±20%, ±10%, ±5%, or ±1% of the indicated range, value, or structure, unless otherwise indicated.

"Amino" refers to the $—NH_2$ radical.

"Cyano" refers to the —CN radical.

"Nitro" refers to the $—NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Hydrazino" refers to the $=N—NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-Cis alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, $—OR^a$, $—SR^a$, $—OC(O)—R^a$, $—N(R^a)_2$, $—C(O)R^a$, $—C(O)OR^a$, $—C(O)N(R^a)_2$, $—N(R^a)C(O)OR^a$, $—OC(O)—N(R^a)_2$, $—N(R^a)C(O)R^a$, $—N(R^a)S(O)_tR^a$ (where t is 1 or 2), $—S(O)_tOR^a$ (where t is 1 or 2), $—S(O)_tR^a$ (where t is 1 or 2) and $—S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)C(O)OR^a$, —$R^b$—$N(R^a)C(O)R^a$, —$R^b$—

$N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $—R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $—R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $—R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula $—OR^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "carbocyclyl". Examples of monocyclic carbocyclyls include, e.g., cyclopropyl, cyclobutyl, cyclopentyl, cyclohexyl, cycloheptyl, and cyclooctyl. An unsaturated carbocyclyl is also referred to as "cycloalkenyl". Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7 dimethyl bicyclo[2.2.1] heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—OR^a$, $—SR^a$, $—OC(O)—R^a$, $—N(R^a)_2$, $—C(O)R^a$, $—C(O)OR^a$, $—C(O)N(R^a)_2$, $—N(R^a)C(O)OR^a$, $—OC(O)—N(R^a)_2$, $—N(R^a)C(O)R^a$, $—N(R^a)S(O)_tR^a$ (where t is 1 or 2), $—S(O)_tOR^a$ (where t is 1 or 2), $—S(O)_tR^a$ (where t is 1 or 2) and $—S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each Rb is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $—R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula $—O—R^c$-carbocyclyl where $R^c$ is an alkylene chain as defined above. The alkylene chain and the carbocyclyl radical is optionally substituted as defined above.

"Carbocyclylalkynyl" refers to a radical of the formula $—R^c$-carbocyclyl, where $R^c$ is an alkynylene chain as defined above. The carbocyclyl part of the carbocyclylalkynyl radical is optionally substituted as described above for an carbocyclyl group. In some embodiments the carbocyclyl group is a carbocyclyl group. The alkynylene chain part of the carbocyclylalkynyl radical is optionally substituted as defined above for an alkynylene chain.

"Carbonyl" refers to a radical of the formula $—C(O)R^{10}R^{20}$, wherein $R^{10}$ and $R^{20}$ is independently selected from —OH, halo, cyano, nitro, oxo, thioxo, imino, oximo, trimethylsilanyl, $—R^a$, $—OR^a$, $—SR^a$, $—OC(O)—R^a$, $—N(R^a)_2$, $—C(O)R^a$, $—C(O)OR^a$, $—C(O)N(R^a)_2$, $—N(R^a)C(O)OR^a$, $—OC(O)—N(R^a)_2$, $—N(R^a)C(O)R^a$, $—N(R^a)S(O)_tR^a$ (where t is 1 or 2), $—S(O)_tOR^a$ (where t is 1 or 2), $—S(O)_tR^a$ (where t is 1 or 2) and $—S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3 to 18 membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $—R^c$-heterocyclyl where $R^c$ is an alkylene chain as defined above. If the heterocyclyl is a nitrogen containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $—O—R^c$ heterocyclyl where $R^c$ is an alkylene chain as defined above. If the heterocyclyl is a nitrogen containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3 to 18 membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized $(4n+2)$ π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term “heteroaryl” is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

“N-heteroaryl” refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

“C-heteroaryl” refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

“Heteroarylalkyl” refers to a radical of the formula $—R^c$-heteroaryl, where $R^c$ is an alkylene chain as defined above. If the heteroaryl is a nitrogen containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

“Heteroarylalkoxy” refers to a radical bonded through an oxygen atom of the formula $—O—R^c$ heteroaryl, where $R^c$ is an alkylene chain as defined above. If the heteroaryl is a nitrogen containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

Embodiments of the disclosure are meant to encompass pharmaceutically acceptable salts, tautomers, isotopologues, and stereoisomers of the compounds provided herein, such as the compounds of Formula (I).

As used herein, the term “pharmaceutically acceptable salt(s)” refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride, formic, and mesylate salts. Others are well-known in the art, see for example, *Remington's Pharmaceutical Sciences,* $18^{th}$ eds., Mack Publishing, Easton PA (1990) or *Remington: The Science and Practice of Pharmacy,* $19^{th}$ eds., Mack Publishing, Easton PA (1995).

As used herein and unless otherwise indicated, the term “stereoisomer” or “stereoisomerically pure” means one stereoisomer of a particular compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds disclosed herein can have chiral centers and can occur as racemates, individual enantiomers or diastereomers, and mixtures thereof. All such isomeric forms are included within the embodiments disclosed herein, including mixtures thereof.

The use of stereoisomerically pure forms of the compounds disclosed herein, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); Wilen, S. H., Tables of *Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

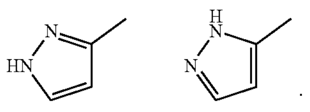

As readily understood by one skilled in the art, a wide variety of functional groups and other structures may exhibit tautomerism and all tautomers of compounds of Formula (I) are within the scope of the present disclosure.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan.

It should also be noted the compounds disclosed herein can contain unnatural proportions of atomic isotopes at one or more of the atoms. For example, the compounds may be radiolabeled with radioactive isotopes, such as for example tritium (H), iodine-125 ($^{125}I$), sulfur-35 ($^{35}S$), or carbon-14 ($^{14}C$), or may be isotopically enriched, such as with deuterium ($^{2}H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically encriched compounds are useful as therapeutic agents, e.g., cancer therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds disclosed herein, for example, the isotopologues are deuterium, carbon-13, and/or nitrogen-15 enriched compounds. As used herein, "deuterated", means a compound wherein at least one hydrogen (H) has been replaced by deuterium (indicated by D or $^{2}H$), that is, the compound is enriched in deuterium in at least one position.

It is understood that, independently of stereoisomerical or isotopic composition, each compound disclosed herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof disclosed herein, may otherwise vary independently from the selection of the pharmaceutically acceptable salt of the respective compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a cancer, as described herein, or symptoms thereof.

The term "effective amount" in connection with a compound disclosed herein means an amount capable of treating or preventing a disorder, disease or condition, or symptoms thereof, disclosed herein.

The term "subject" or "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an CaMKK2 mediated disease, or a symptom thereof.

Mammalian CAMKK2 proteins are 66-68-kDa kinases including unique N- and C-terminal domains, a central Ser/Thr-directed kinase domain, and a regulatory domain composed of overlapping autoinhibitory and CAM-binding regions. CAMKK2 proteins are auto-inhibited by a sequence located immediately C-terminal to its catalytic domain, and $Ca^{2+}$/CAM binding causes conformational changes that stimulate kinase activity. Once activated, CAMKK2 proteins can phosphorylate CAMKIV and CAMKI increasing their enzymatic activity. 5' AMP-activated protein kinase a (AMPKα) is an additional substrate of CAMKK2 proteins, and silencing of CAMKK2 proteins in mammalian cells almost completely abolishes AMPK activation. Although CAMKK2 proteins can be detected in many areas of the brain, outside this organ the expression of CAMKK2 proteins is less clear. In the immune system, CAMKK2 proteins have been found exclusively in myeloid cells, including hematopoietic progenitors, peritoneal macrophages and bone marrow-derived macrophages. Genetic ablation of CAMKK2 proteins interferes with development and function of myeloid cells, and in turn has important effects on the inflammatory response.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Compounds

In one aspect, provided herein is a compound of Formula (I):

(I)

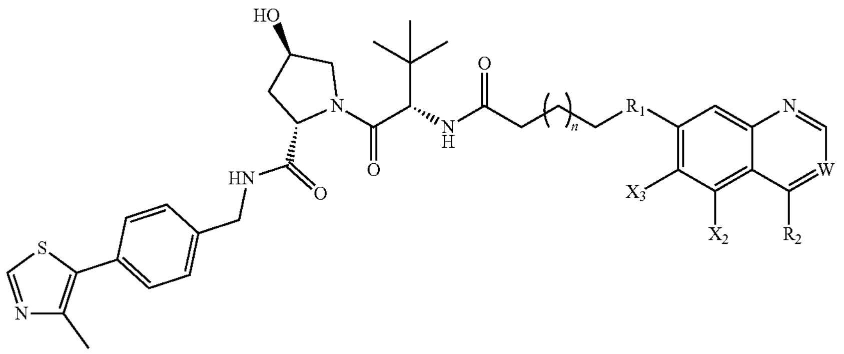

or a pharmaceutically acceptable salt thereof, wherein:

W is N or $CX_1$;

$R_1$ is O or optionally substituted heteroarylene;

$R_2$ is optionally substituted aryl;

$X_1$, $X_2$, and $X_3$ are independently hydrogen, halogen, or —CN; and n is 2-10.

In some embodiments, W is N. In other embodiments, W is $CX_1$.

In some embodiments, $X_1$ is hydrogen, halogen, or —CN. In some embodiments, $X_1$ is hydrogen or halogen.

In some embodiments, $X_1$ is hydrogen. In some embodiments, $X_1$ is —CN.

In some embodiments, $X_1$ is halogen. In some embodiments, $X_1$ is fluoro, chloro, or bromo. In some embodiments, $X_1$ is fluoro. In some embodiments, $X_1$ is chloro. In some embodiments, $X_1$ is bromo.

In some embodiments, $R_1$ is O.

In some embodiments, $R_1$ is optionally substituted heteroarylene. In some embodiments, the optionally substituted heteroarylene comprises 1-4 heteroatoms selected from N, O, and S. In some embodiments, the optionally substituted heteroarylene comprises 1-3 heteroatoms selected from N and O. In some embodiments, $R_1$ is optionally substituted 5- to 10-membered heteroarylene. In some embodiments, $R_1$ is optionally substituted 5- to 6-membered heteroarylene. In some embodiments, $R_1$ is optionally substituted 8- to 10-membered heteroarylene. In some embodiments, the optionally substituted heteroarylene is a monocylic ring. In some embodiments, the optionally substituted heteroarylene is a fused bicylic ring. In some embodiments, $R_1$ is pyrazolylene optionally substituted with methyl. In some embodiments, $R_1$ is optionally substituted pyridinylene. In some embodiments, $R_1$ is optionally substituted pyrazinylene, pyrimidinylene, pyridazinylene, triazinylene, quinolinylene, isoquinolinylene, quinazolinylene, quinoxalinylene, pyrrolylene, furanylene, imidazolylene, or triazolylene.

In some embodiments, $R_2$ is optionally substituted aryl. In some embodiments, $R_2$ is optionally substituted 6- to 10-membered aryl. In some embodiments, $R_2$ is optionally substituted phenyl. In some embodiments, the optionally substituted aryl is a monocylic ring. In some embodiments, the optionally substituted aryl is a bicylic ring. In some embodiments, $R_2$ is aryl optionally substituted by at least one substituent selected from alkyl, carbonyl, carbocyclyl, heterocyclyl, and heteroaryl. In some embodiments, $R_2$ is aryl optionally substituted by at least one substituent selected from $C_1$-$C_6$ alkyl, carbonyl, $C_3$-$C_{10}$ carbocyclyl, 4- to 10-membered heterocyclyl, and 4- to 10-membered heteroaryl. In some embodiments, $R_2$ is aryl optionally substituted by $C_1$-$C_3$ alkyl optionally substituted by halogen or $C_3$-$C_4$ carbocyclyl. In some embodiments, $R_2$ is aryl optionally substituted by —$CO_2$H or —C(O)$NH_2$. In some embodiments, $R_2$ is aryl optionally substituted by $C_3$-$C_5$ carbocyclyl optionally substituted by halogen. In some embodiments, $R_2$ is aryl substituted by $C_3$-$C_5$ carbocyclyl. In some embodiments, $R_2$ is aryl substituted by $C_5$ carbocyclyl. In some embodiments, $R_2$ is aryl substituted by —$CO_2$H. In some embodiments, $R_2$ is aryl substituted by $C_3$-$C_5$ carbocyclyl and $—CO_2H$. In some embodiments, $R_2$ is aryl substituted by $C_5$ carbocyclyl and $—CO_2H$. In some embodiments, $R_2$ is aryl optionally substituted by a 6-membered heterocyclyl containing a nitrogen atom. In some embodiments, $R_2$ is aryl optionally substituted by tetrazolyl.

In some embodiments, $X_2$ and $X_3$ are independently hydrogen, halogen, or —CN. In some embodiments, $X_2$ and $X_3$ are independently hydrogen or halogen. In some embodiments, $X_2$ and $X_3$ are each hydrogen.

In some embodiments, $X_2$ is hydrogen. In some embodiments, $X_2$ is —CN. In some embodiments, $X_2$ is halogen. In some embodiments, $X_2$ is fluoro, chloro, or bromo. In some embodiments, $X_2$ is fluoro. In some embodiments, $X_2$ is chloro. In some embodiments, $X_2$ is bromo.

In some embodiments, $X_3$ is hydrogen. In some embodiments, $X_3$ is —CN. In some embodiments, $X_3$ is halogen. In some embodiments, $X_3$ is fluoro, chloro, or bromo. In some embodiments, $X_3$ is fluoro. In some embodiments, $X_3$ is chloro. In some embodiments, $X_3$ is bromo.

In some embodiments, n is 2-10. In some embodiments, n is 3-10. In some embodiments, n is 4-10. In some embodiments, n is 2-9. In some embodiments, n is 3-9. In some embodiments, n is 4-9. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments,

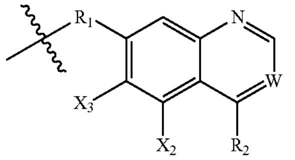

is a moiety selected from:

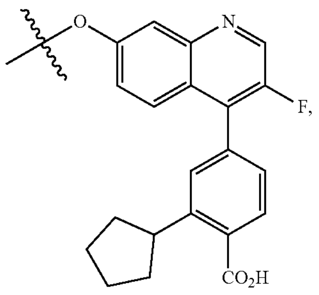

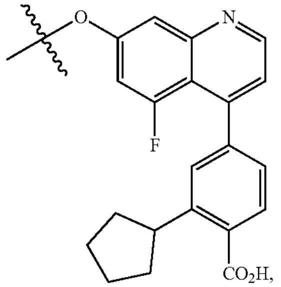

-continued

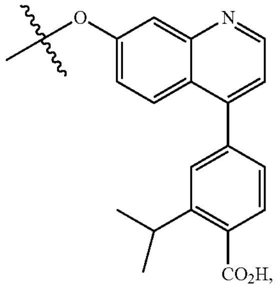

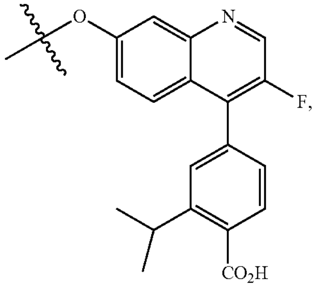

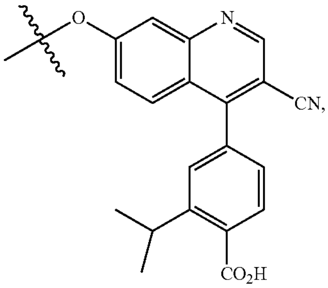

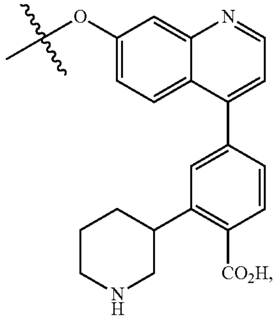

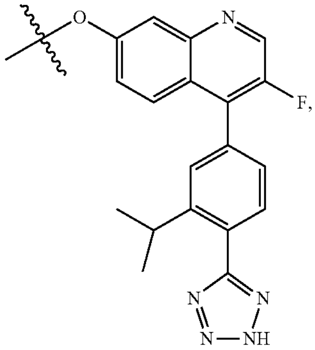

-continued
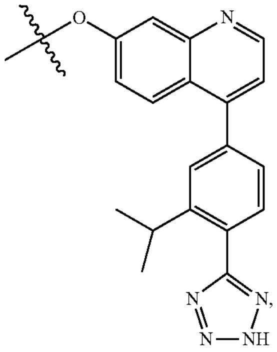
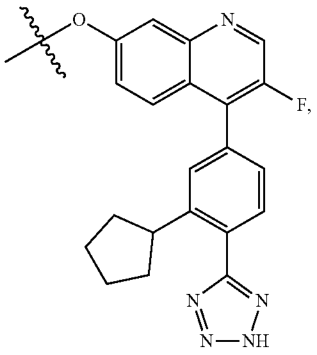
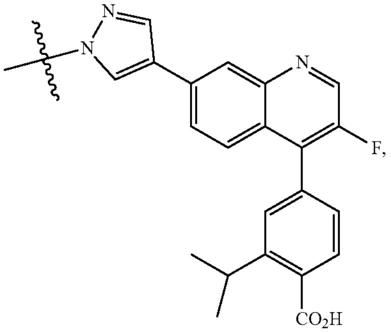
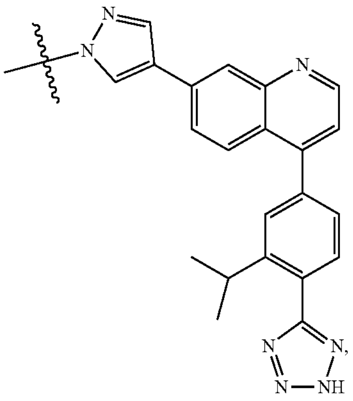
-continued
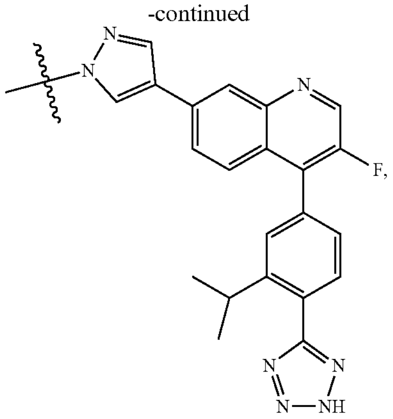
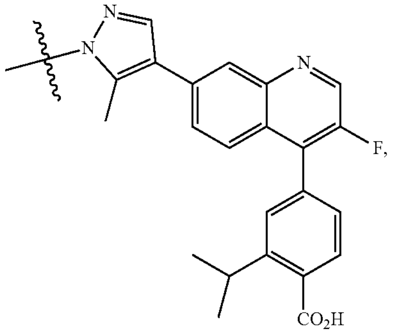
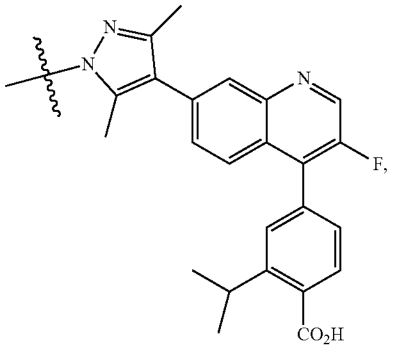
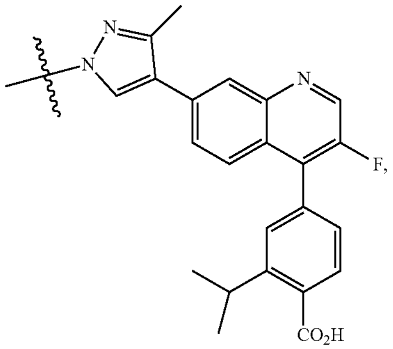
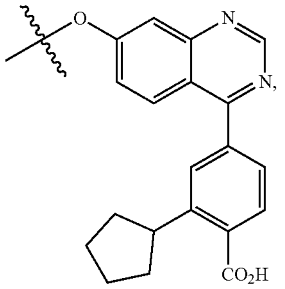

-continued
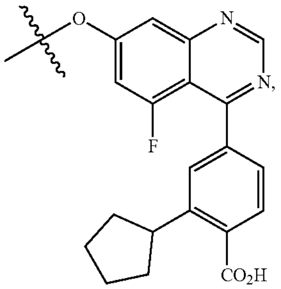
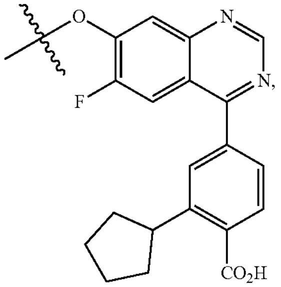
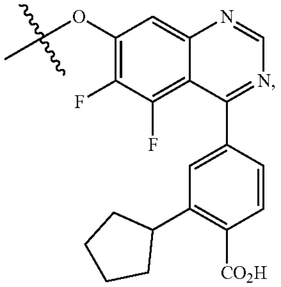
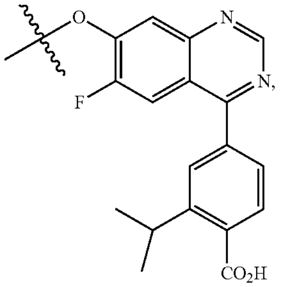
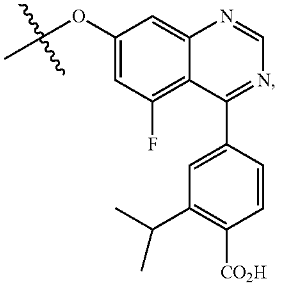
-continued
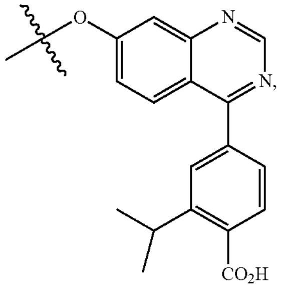
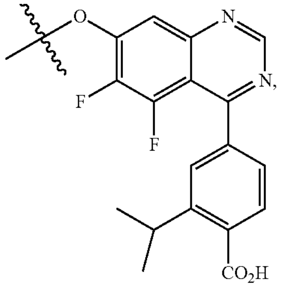
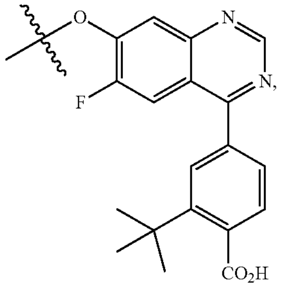
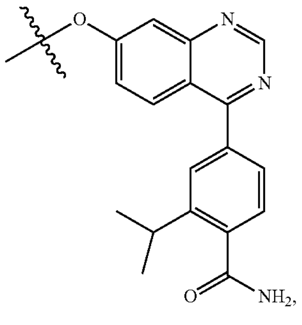
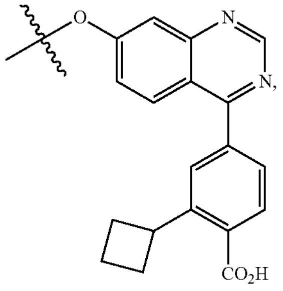

-continued
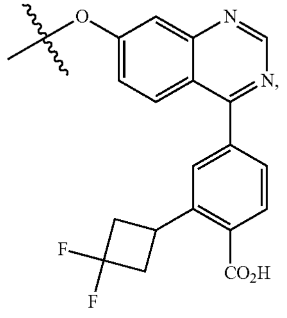
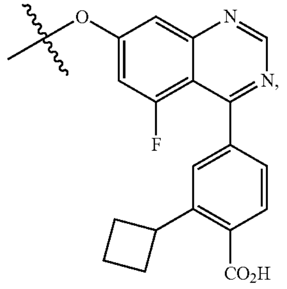
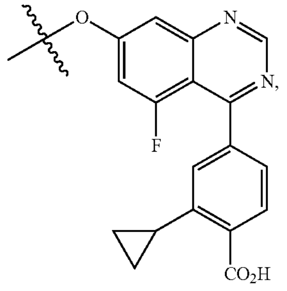
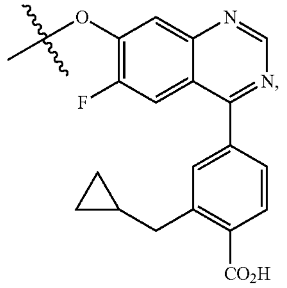
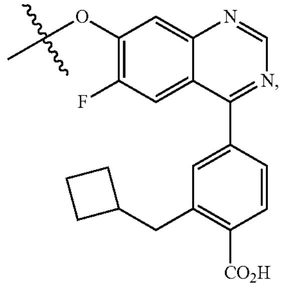
-continued
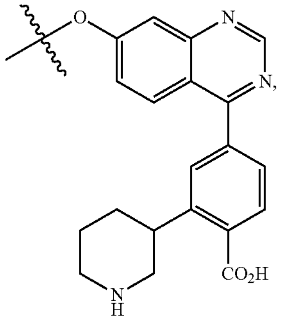
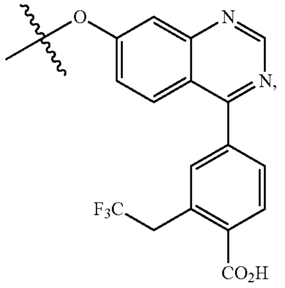
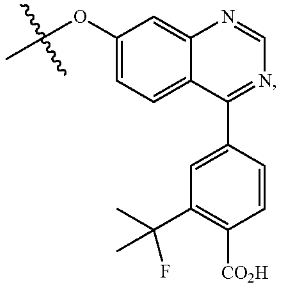
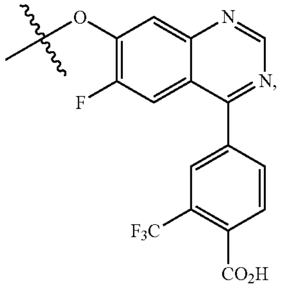
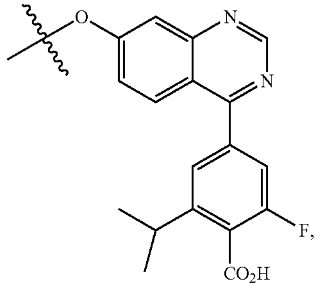

-continued
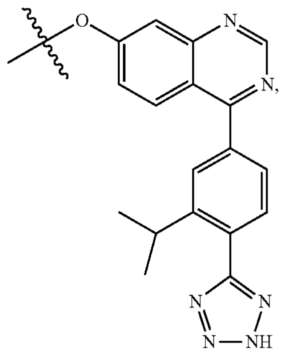
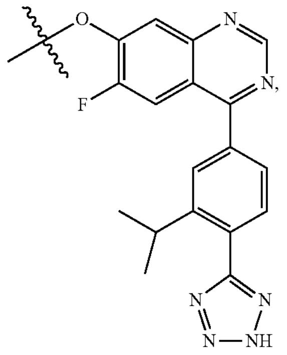
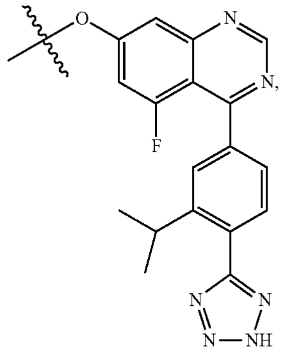
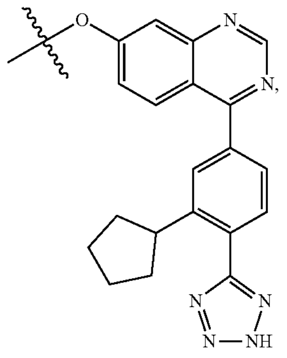
-continued
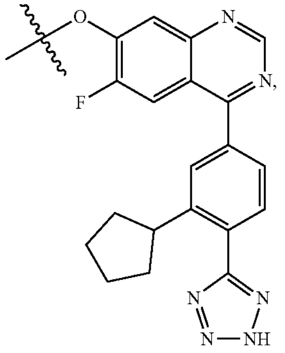
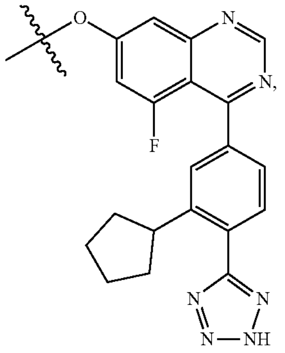
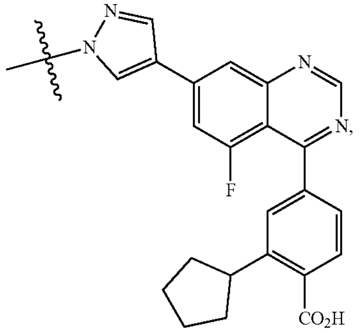
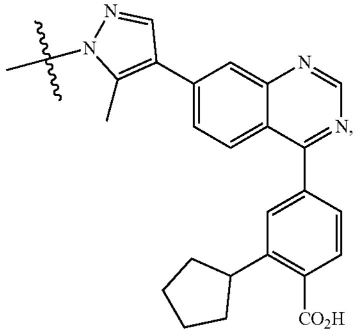
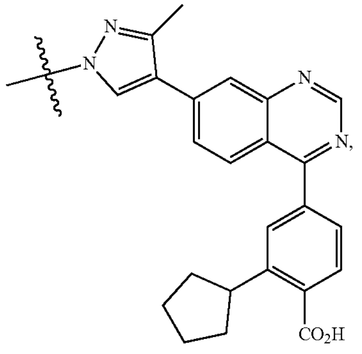

-continued
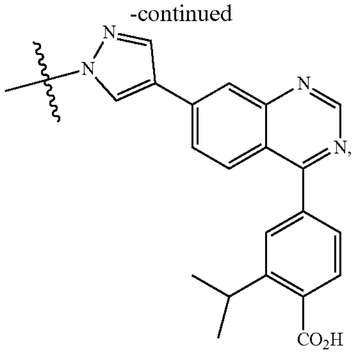
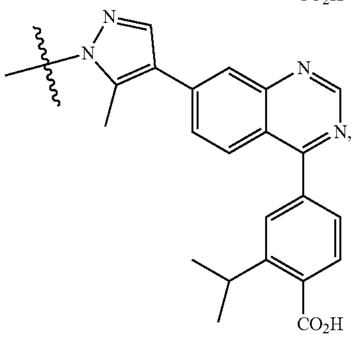
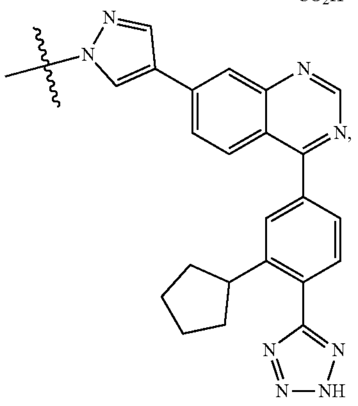
-continued
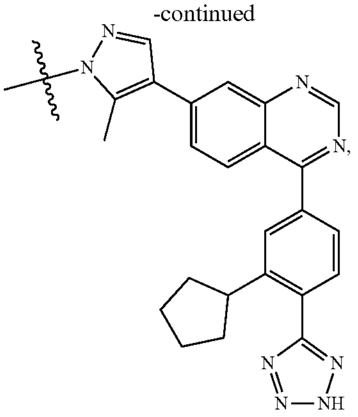
and
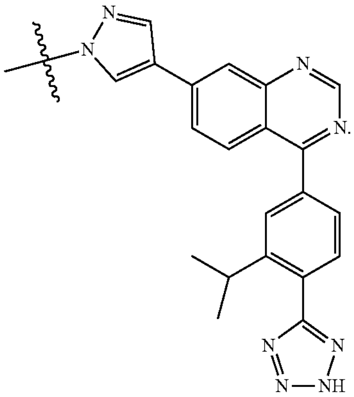 [SMILES: *n1cc(-c2ccc3c(-c4ccc(-c5nn[nH]n5)c(C(C)C)c4)ncnc3c2)cn1]
In some embodiments, the compound of Formula (I) is a compound of Formula (IA):
(IA)
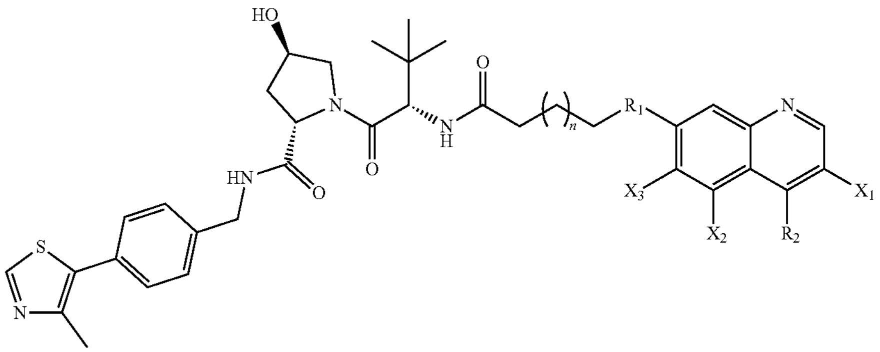
wherein $R_1$, $R_2$, $X_1$, $X_2$, $X_3$, and n are as described for Formula (I).

In some embodiments, the compound of Formula (I) is a compound is of Formula (IA-1) or (IA-2):
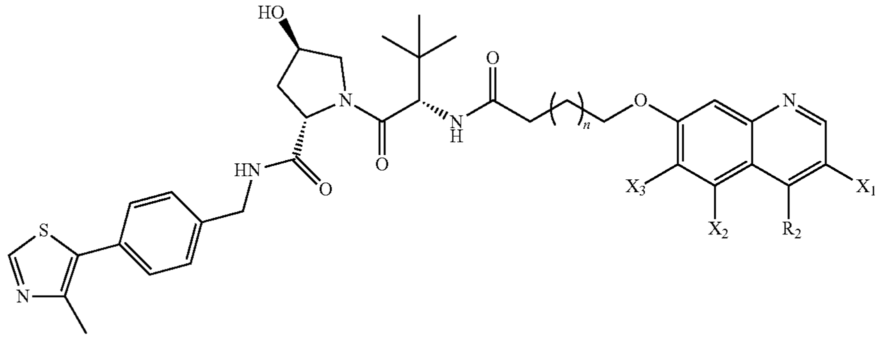
(IA-1)
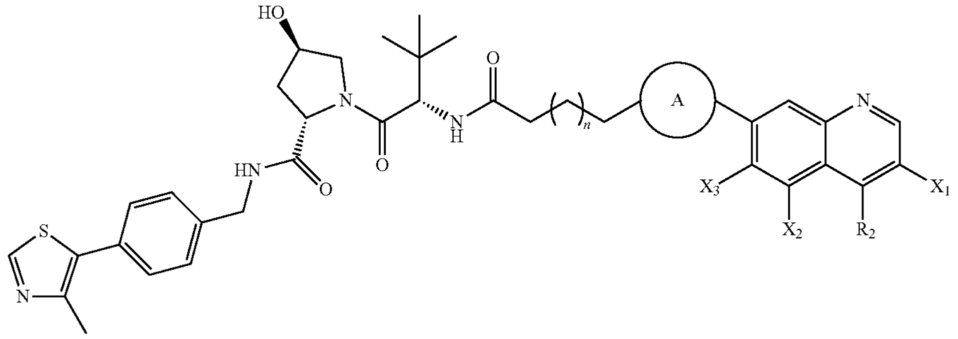
(IA-2)
wherein $R_2$, $X_1$, $X_2$, $X_3$, and n are as described for Formula (I), and Ring A is an optionally substituted heteroarylene.
In some embodiments, the compound of Formula (I) is a compound is of Formula (IB):
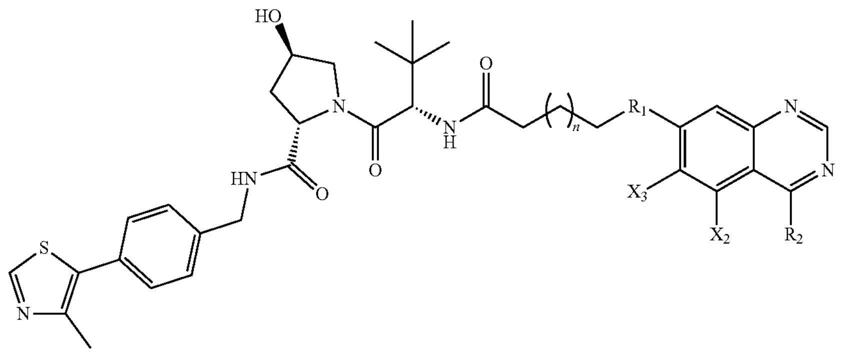
(IB)
wherein $R_1$, $R_2$, $X_2$, $X_3$, and n are as described for Formula (I).

In some embodiments, the compound of Formula (I) is a compound of Formula (IB-1) or (IB-2):
(IB-1)
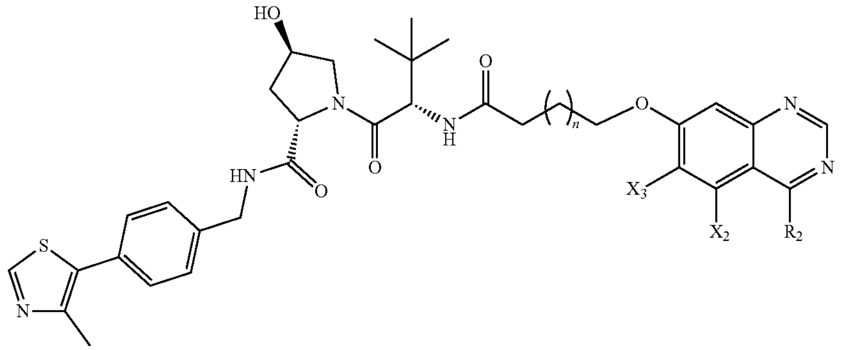
(IB-2)
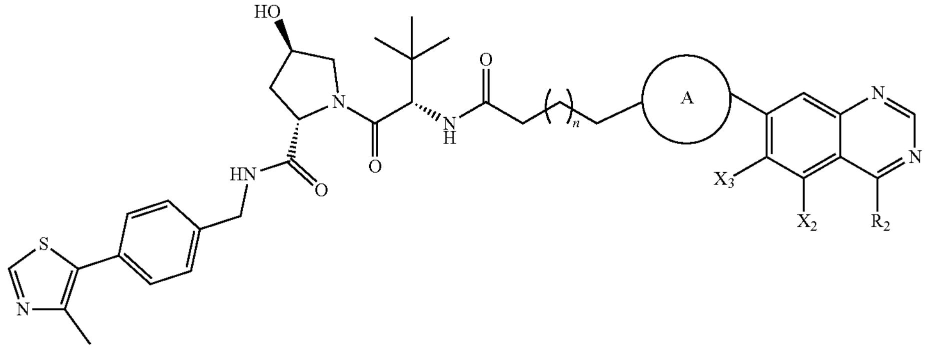
wherein $R_2$, $X_2$, $X_3$, and n are as described for Formula (I), and Ring A is an optionally substituted heteroarylene.
In some embodiments, the compound of Formula (I) is a compound is of Formula (IC-1) or (IC-2):
(IC-1)
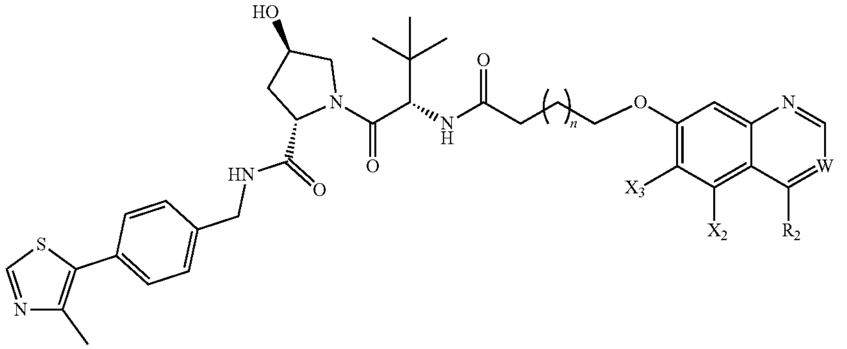
(IC-2)
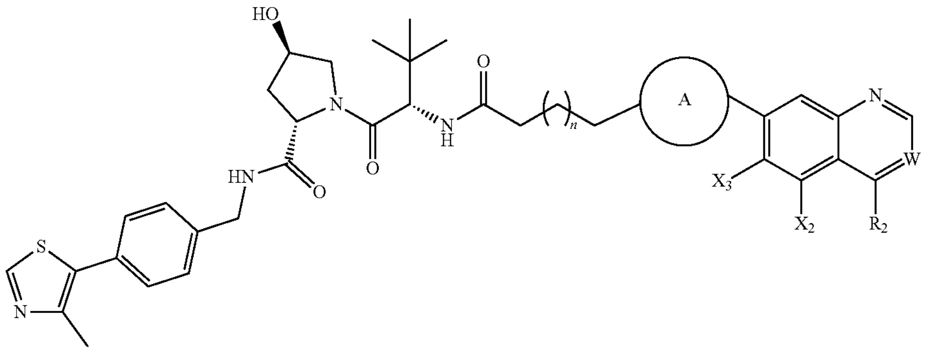

wherein W, $R_2$, $X_2$, $X_3$, and n are as described for Formula (I), and Ring A is an optionally substituted heteroarylene.

In some embodiments, the compound of Formula (I) is a compound is of Formula (Ia):

(Ia)

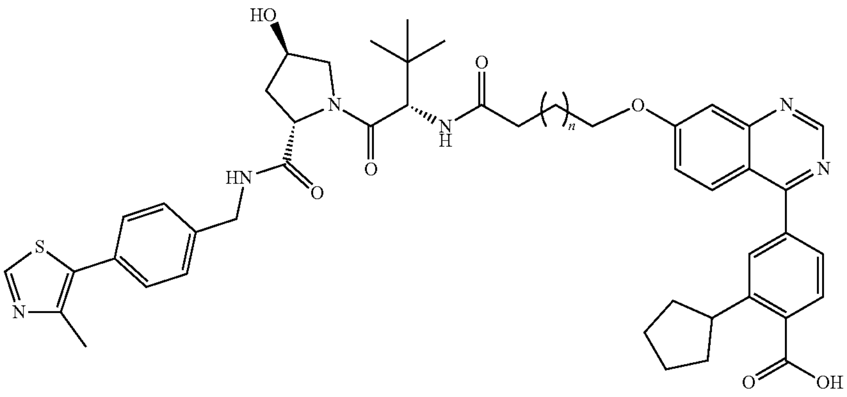

wherein n is as described for Formula (I).

In some embodiments, the compound of Formula (I) is a compound of Formula (Ib):

(Ib)

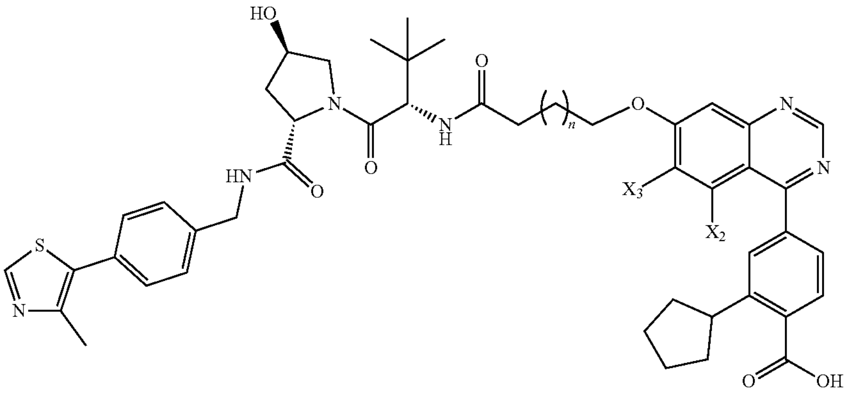

wherein $X_2$, $X_3$, and n are as described for Formula (I). In some embodiments, $X_2$ and $X_3$ are independently H or halo. In some embodiments, $X_2$ and $X_3$ are independently H, F, or $C_1$. In some embodiments, $X_2$ and $X_3$ are independently H or F.

In the descriptions herein, it is understood that all descriptions, variations, embodiments, or aspects of Formula (I), where applicable, apply equally to other formulae detailed herein, and are equally described, the same as if each and every description, variation, embodiment, or aspect were separately and individually listed. For example, every description, variation, embodiment, or aspect provided herein with respect to W of Formula (I) may be combined with every description, variation, embodiment, or aspect of $R_1$, $R_2$, $X_1$, $X_2$, $X_3$, and n, the same as if each and every combination were specifically and individually listed. It is also understood that all descriptions, variations, embodiments, or aspects of Formula (I), where applicable, apply equally to other formulae detailed herein, and are equally described, the same as if each and every description, variation, embodiment, or aspect were separately and individually listed for all formulae. For example, all descriptions, variations, embodiments, or aspects of Formula (I), where applicable, apply equally to any of the formulae as detailed herein, such as Formulae (IA), (IA-1), (IA-2), (IB), (IB-1), (IB-2), (Ia), and (Ib), and are equally described, the same as if each and every description, variation, embodiment, or aspect were separately and individually listed for all formulae.

In some embodiments, provided is a compound selected from the compounds in Table 1 or a pharmaceutically acceptable salt thereof. Although certain compounds described in the present disclosure, including in Table 1, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1, are herein described.

TABLE 1
| Compound No. | Structure |
| --- | --- |
| 1 | 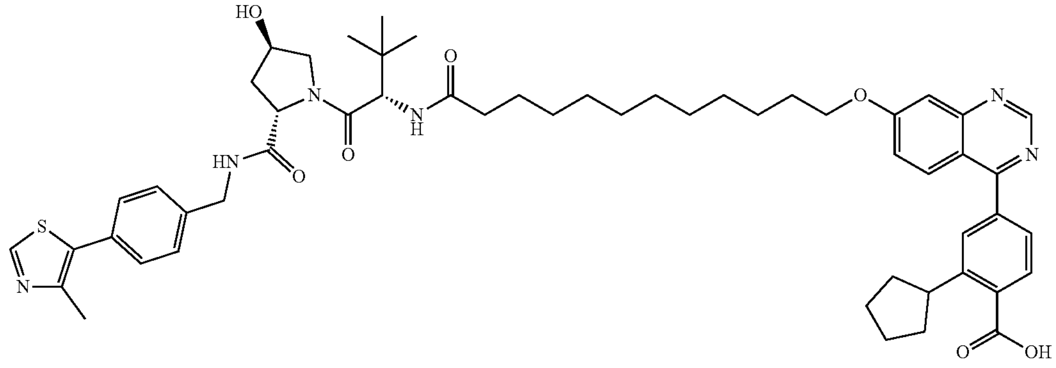 [SMILES: Cc1ncsc1-c1ccc(CNC(=O)[C@@H]2C[C@@H](O)CN2C(=O)[C@@H](NC(=O)CCCCCCCCCCCOc2ccc3c(-c4ccc(C(=O)O)c(C5CCCC5)c4)ncnc3c2)C(C)(C)C)cc1] |
| 2 | 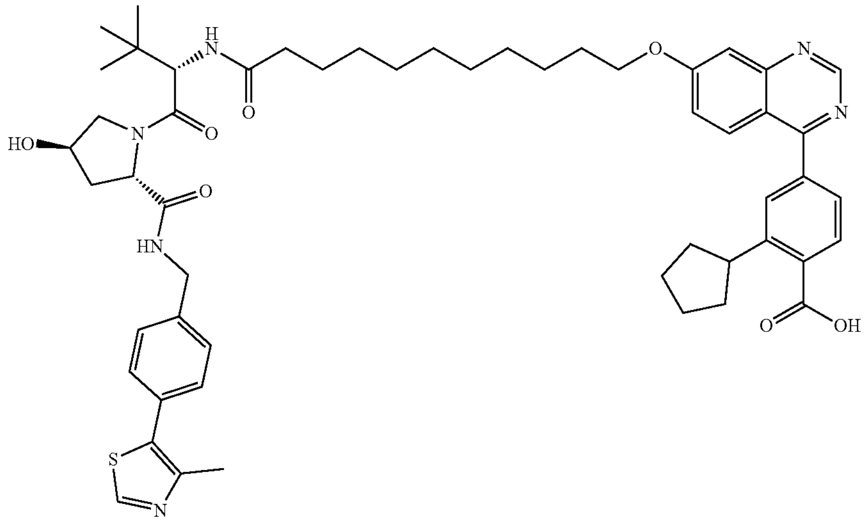 [SMILES: Cc1ncsc1-c1ccc(CNC(=O)[C@@H]2C[C@@H](O)CN2C(=O)[C@@H](NC(=O)CCCCCCCCCCOc2ccc3c(-c4ccc(C(=O)O)c(C5CCCC5)c4)ncnc3c2)C(C)(C)C)cc1] |
| 3 | 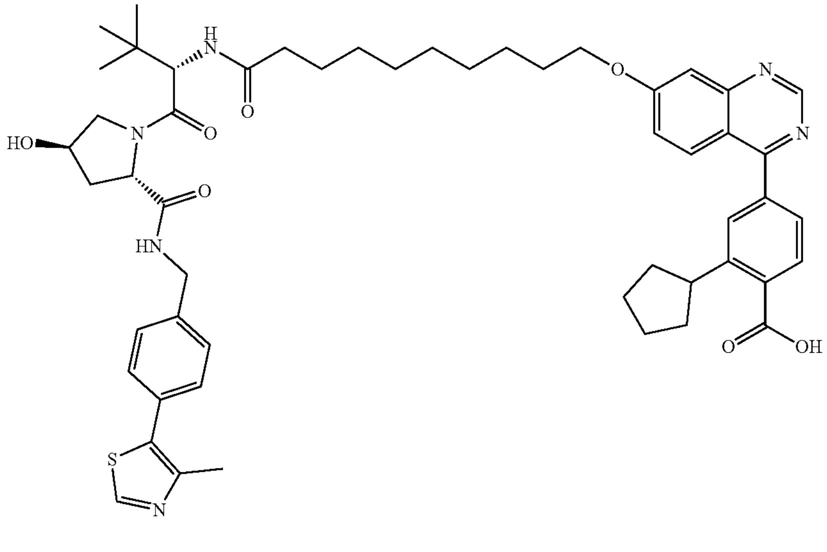 [SMILES: Cc1ncsc1-c1ccc(CNC(=O)[C@@H]2C[C@@H](O)CN2C(=O)[C@@H](NC(=O)CCCCCCCCCOc2ccc3c(-c4ccc(C(=O)O)c(C5CCCC5)c4)ncnc3c2)C(C)(C)C)cc1] |

TABLE 1-continued
| Compound No. | Structure |
|---|---|
| 4 | 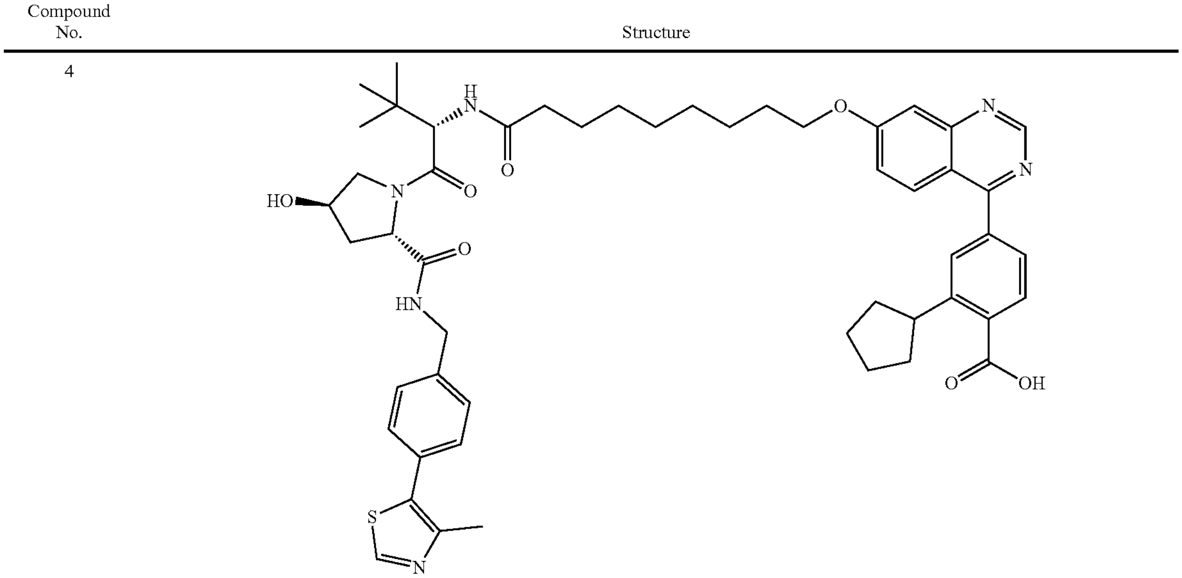 |
| 5 | 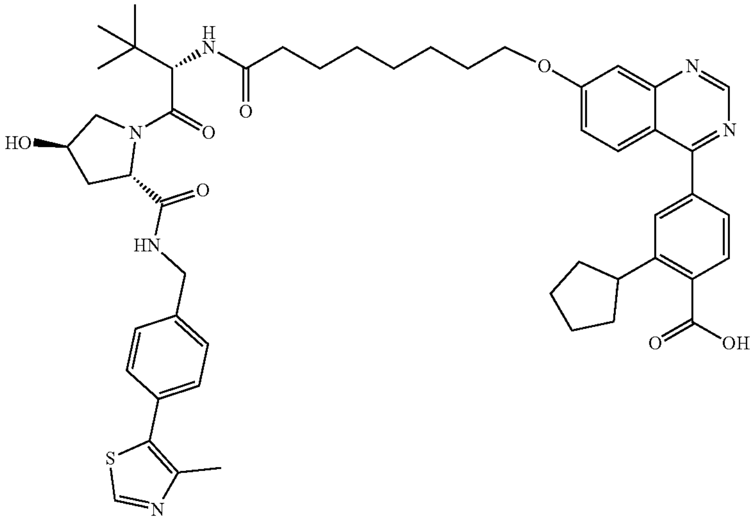 [SMILES: Cc1ncsc1-c1ccc(CNC(=O)[C@@H]2C[C@@H](O)CN2C(=O)[C@@H](NC(=O)CCCCCCCOc2ccc3c(-c4ccc(C(=O)O)c(C5CCCC5)c4)ncnc3c2)C(C)(C)C)cc1] |
| 6 | 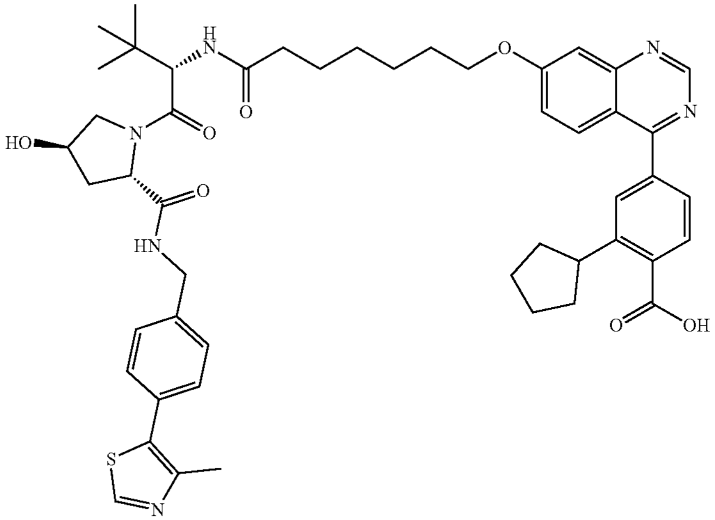 [SMILES: Cc1ncsc1-c1ccc(CNC(=O)[C@@H]2C[C@@H](O)CN2C(=O)[C@@H](NC(=O)CCCCCCOc2ccc3c(-c4ccc(C(=O)O)c(C5CCCC5)c4)ncnc3c2)C(C)(C)C)cc1] |
or a pharmaceutically acceptable salt thereof.

All compounds of Formula (I) that exist in free base or acid form can be converted to their pharmaceutically acceptable salts by treatment with the appropriate inorganic or organic base or acid by methods known to one skilled in the art. Salts of the compounds of Formula (I) can be converted to their free base or acid form by standard techniques.

Methods of Synthesis

The compounds described herein can be made using conventional organic syntheses and commercially available starting materials, or the methods provided herein. By way of example and not limitation, compounds of Formula (IC-1) can be prepared as outlined in Scheme 1, as well as in the Examples set forth herein. It should be noted that one skilled in the art would know how to modify the procedures set forth in the illustrative schemes and Examples to arrive at the desired products.

Scheme 1.

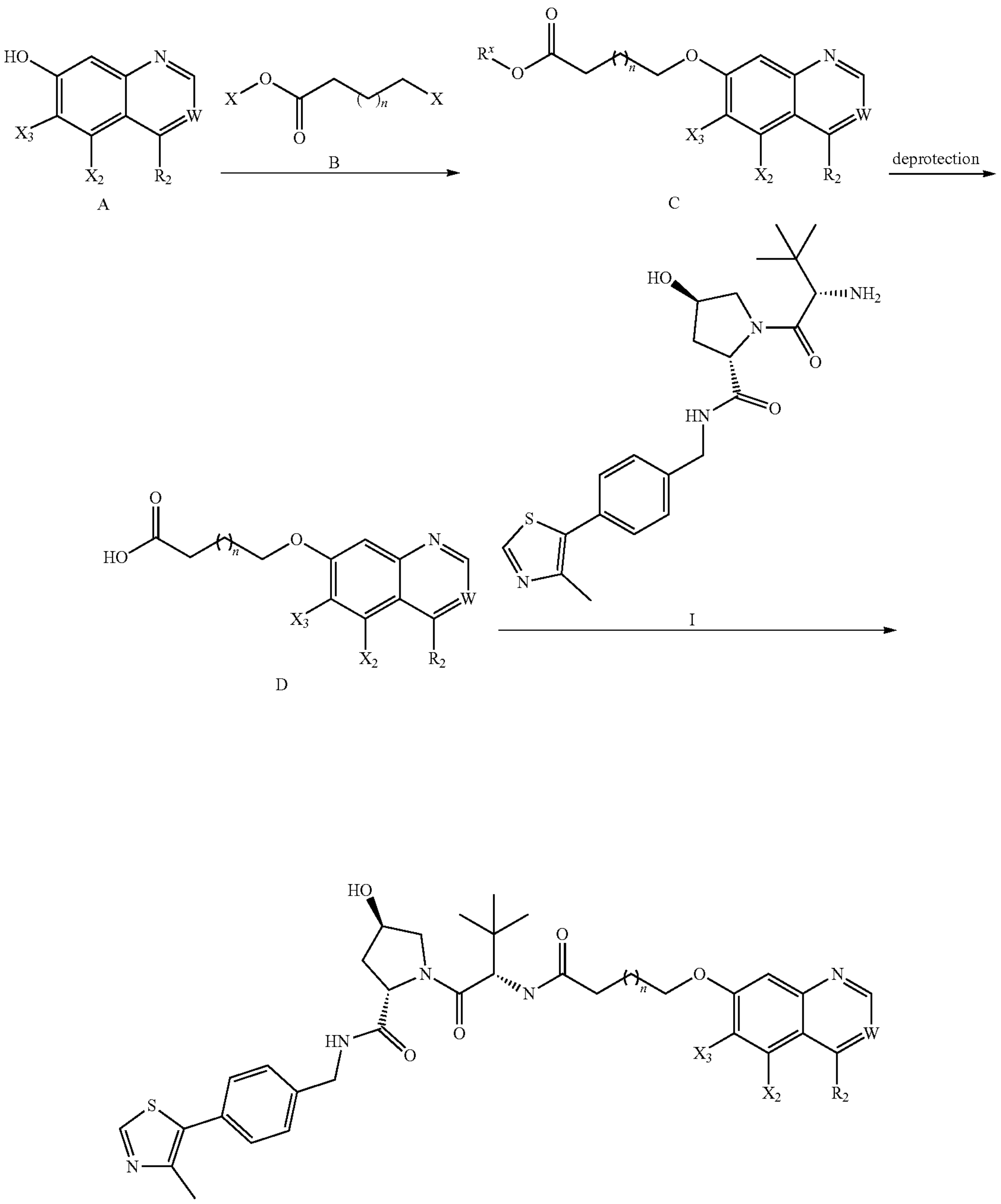

(IC-1)

wherein W, $X_2$, $X_3$, $R_2$, and n are as defined for the Formula (I); $R^x$ is an alkyl group, such as ethyl or methyl; and X is a halogen, such as Br.

Scheme 2.
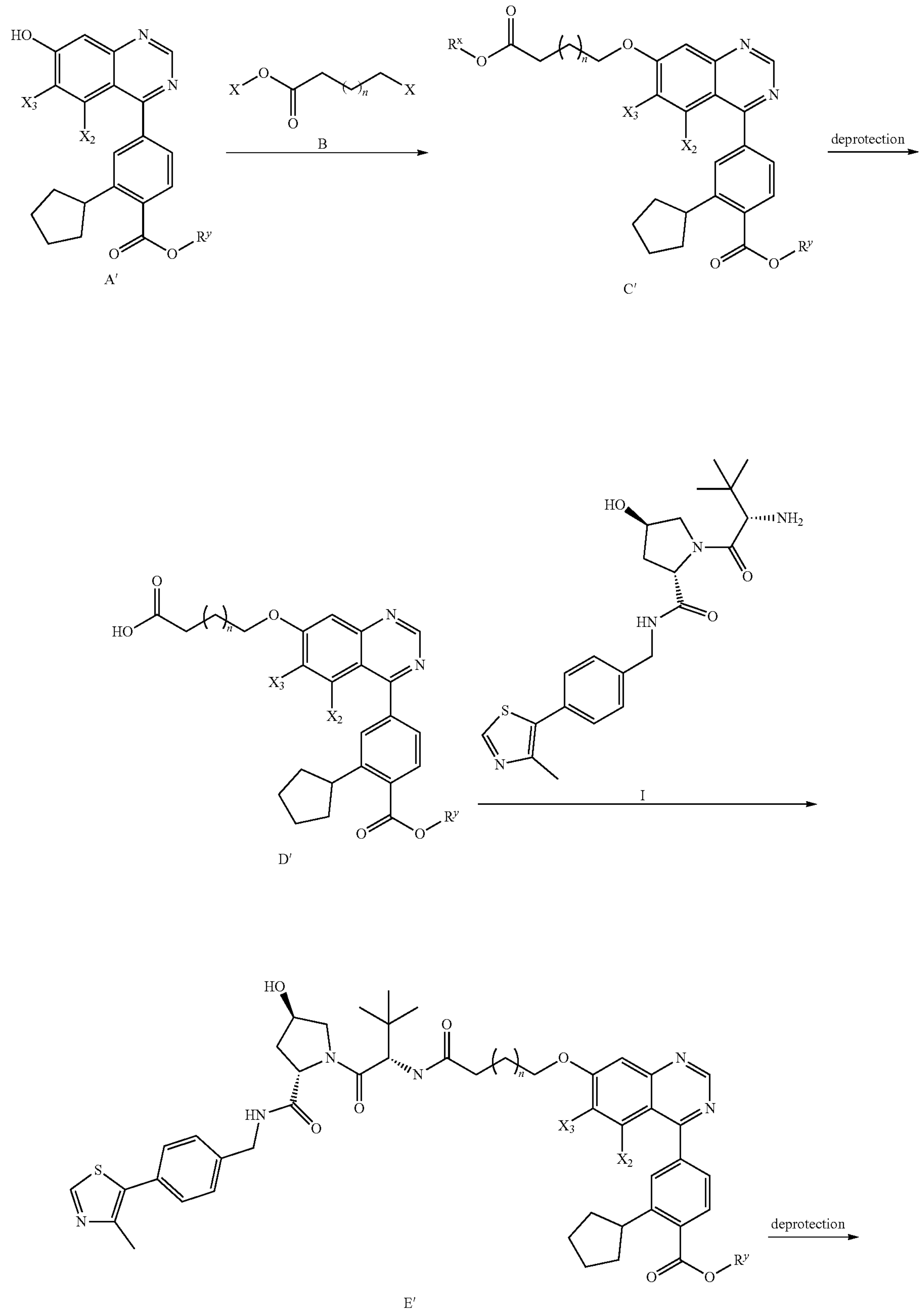
A′
C′
D′
E′

-continued

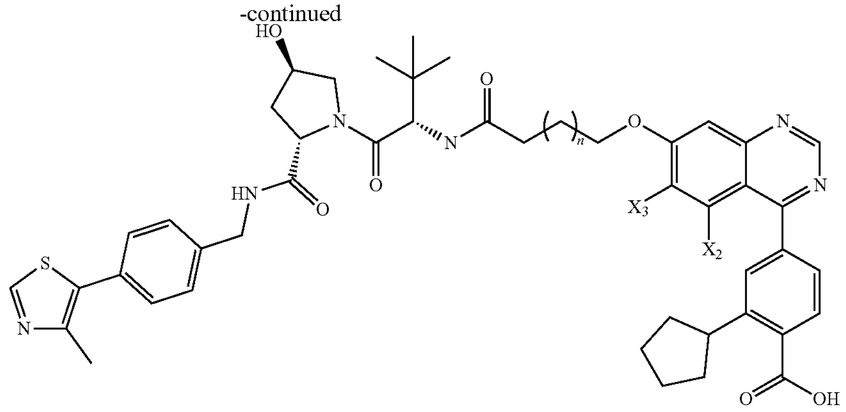

(Ib)

wherein $X_2$, $X_3$, $R_2$, and n are as defined for Formula (I); $R^x$ is an alkyl group, such as ethyl or methyl; X is a halogen, such as Br; and $R^y$ is an alkyl group, such as tert-butyl.

As outlined in Scheme 1, compounds of Formula (I) wherein $R_1$ is O, i.e., compounds of Formula (IC-1), can be synthesized from quinazoline derivative A via coupling to intermediate compounds B to afford intermediate compounds C, which are then deprotected to form intermediate compounds D, followed by coupling to intermediate I to form compounds of Formula (IC-1).

Scheme 2 provides a synthesis of compounds of Formula (Ib). Quinazoline derivative A' can be coupled to intermediate compounds B to afford intermediate compounds C', which are then deprotected to form intermediate compounds D', followed by coupling to intermediate I and subsequent deprotection of the ester by, for example acid, to form compounds of Formula (Ib).

Methods of Use

Embodiments of the present disclosure provide a method for modulating CAMKK2 in a subject in need thereof, the method comprising administering to the subject an effective amount of a compound of Formula (I). Modulation (e.g., inhibition or activation) of CAMKK2 can be assessed and demonstrated by a wide variety of ways known in the art. Kits and commercially available assays can be utilized for determining whether and to what degree CAMKK2 has been modulated (e.g., inhibited or activated).

In one aspect, provided herein is a method of modulating CAMKK2 comprising contacting CAMKK2 with an effective amount of a compound of Formula (I) or any embodiment or variation thereof. In some embodiments, the compound of Formula (I) inhibits CAMKK2. In some embodiments, the compound of Formula (I) causes degradation of CAMKK2.

In some embodiments, a compound of Formula (I) modulates the activity of CAMKK2 by about 1%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, a compound of formula (I) modulates the activity of CAMKK2 by about 1-100%, 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, 30-70%, or 40-60%.

Also provided in certain embodiments of the present disclosure is a method for degrading CAMKK2 in a subject in need thereof, the method comprising administering to the subject an effective amount of a compound of Formula (I). Degradation of CAMKK2 can be assessed and demonstrated by a wide variety of ways known in the art. Kits and commercially available assays, including cell-based assays, can be utilized for determining whether and to what degree CAMKK2 has been degraded.

In one aspect, provided herein is a method of degrading CAMKK2 comprising contacting CAMKK2 with an effective amount of a compound of Formula (I) or any embodiment or variation thereof. In some embodiments, the compound of Formula (I) partially degrades CAMKK2. In some embodiments, the compound of Formula (I) fully degrades CAMKK2.

In some embodiments, a compound of Formula (I) degrades CAMKK2 by about 1%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, a compound of Formula (I) degrades CAMKK2 by about 1-100%, 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, 30-70%, or 40-60%.

In some embodiments, provided herein is a method of regulating gene transcription in a cell comprising modulating CAMKK2 activity by exposing CAMKK2 to the compound of Formula (I). In some embodiments, the method of regulating gene transcription in a cell comprising degrading CAMKK2.

In another aspect, provided herein is a method for treating a cancer in a subject in need thereof, comprising administering to the subject an effective amount of a compound of Formula (I). In some embodiments, provided herein is a method for preventing a cancer in a subject in need thereof, comprising administering to the subject an effective amount of a compound of Formula (I). Non-limiting examples of a cancer include acute myeloid leukemia (AML), acute lymphoblastic leukemia (ALL), small cell lung cancer (SCLC), non-small cell lung cancer (NSCLC), neuroblastoma, small round blue cell tumors, glioblastoma, glioma, prostate cancer, breast cancer, bladder cancer, lung cancer, and melanoma.

In some embodiments, administering a compound of Formula (I) to a subject in need thereof diminishes the extent of the cancer (such as tumor size, tumor growth rate, metastasis) in the subject. In some embodiments, administering a compound of Formula (I) to a subject in need thereof stabilizes the cancer (prevents or delays the worsening of the cancer). In some embodiments, administering a compound of Formula (I) to a subject in need thereof delays the occurrence or recurrence of the cancer. In some embodiments, administering a compound of Formula (I) to a subject in need thereof slows the progression of the cancer. In some embodiments, administering a compound of Formula (I) to a subject in need thereof provides a partial remission of the cancer. In some embodiments, administering a compound of Formula (I) to a subject in need thereof provides a total remission of the cancer. In some embodiments, administering a compound of Formula (I) to a subject in need thereof decreases the dose of one or more other medications required to treat the cancer. In some embodiments, administering a compound of Formula (I) to a subject in need thereof enhances the effect of another medication used to treat the cancer. In some embodiments, administering a compound of Formula (I) to a subject in need thereof delays the progression of the cancer. In some embodiments, administering a compound of Formula (I) to a subject in need thereof increases the quality of life of the subject having a cancer. In some embodiments, administering a compound of Formula (I) to a subject in need thereof prolongs survival of a subject having a cancer.

In some aspects, provided herein is a method of slowing progression of a cancer in a subject, the method comprising administering a compound of Formula (I) to the subject. In some embodiments, provided herein is a method of stabilizing a cancer in a subject, the method comprising administering a compound of Formula (I) to the subject. In some embodiments, the method prevents the progression of the cancer. In some embodiments, the method delays the progression of the cancer. In some embodiments, the method provides a partial or total remission of the cancer.

In another aspect, provided herein is a method of delaying the occurrence or recurrence of a cancer in a subject, the method comprising administering a compound of Formula (I) to the subject.

In further aspects, provided herein is a method of decreasing the dose of one or more other medications required to treat a cancer in a subject, the method comprising administering a compound of Formula (I) to the subject. In some embodiments, provided herein is a method of enhancing the effect of another medication used to treat a cancer in a subject, the method comprising administering a compound of Formula (I) to the subject.

Also provided here is a method of delaying the progression of a cancer in a subject, the method comprising administering a compound of Formula (I) to the subject. In some embodiments, the method increases the quality of life of the subject having a cancer. In some embodiments, the method prolongs survival of the subject having a cancer.

In a further aspect, provided herein a method of promoting weight loss in a subject, the method comprising administering a compound of Formula (I) to the subject. In some embodiments, the method promotes reduced adiposity and/or improved glucose sensitivity in the subject. Accordingly, in some embodiments, provided herein is a method of treating obesity in a subject, the method comprising administering a compound of Formula (I) to the subject.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The compounds disclosed herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds of Formula (I) in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a compound of Formula (I) to be administered to a subject is rather widely variable and can be subject to the judgment of a health-care practitioner. In general, the compounds disclosed herein can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the compound of Formula (I) administered will depend on such factors as the solubility of the active component, the formulation used and the route of administration.

In some embodiments, a compound of Formula (I) is administered to a subject at a dose of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a compound of Formula (I).

In a particular embodiment, provided herein are unit dosage formulations comprising about 0.1 mg or 100 mg of a compound of Formula (I).

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a compound of Formula (I).

A compound of Formula (I) can be administered once, twice, three, four or more times daily. In a particular embodiment, doses of 100 mg or less are administered as a once daily dose and doses of more than 100 mg are administered twice daily in an amount equal to one half of the total daily dose.

A compound of Formula (I) can be administered orally for reasons of convenience. In one embodiment, when administered orally, a compound of Formula (I) is administered with a meal and water. In another embodiment, the compound of Formula (I) is dispersed in water or juice (e.g., apple juice or orange juice) or any other liquid and administered orally as a solution or a suspension.

The compounds disclosed herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound of Formula (I) without an additional carrier, excipient or vehicle.

In another embodiment, provided herein are compositions comprising an effective amount of a compound of Formula (I) and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a compound of Formula (I) with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound of Formula (I) as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound of Formula (I) can be delayed or prolonged by proper formulation. For example, a slowly soluble pellet of the compound of Formula (I) can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound of Formula (I) in oily or emulsified vehicles that allow it to disperse slowly in the serum.

It is understood that the pharmaceutical compositions described herein may include a mixture of compounds of Formula (I), including a racemic mixture of any of the compounds described herein.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

The following abbreviations may be relevant for the application.

Abbreviations

ACN, MeCN acetonitrile
DCM dichloromethane
DIEA diisopropylethylamine
DMF dimethylformamide
DMSO dimethyl sulfoxide
EA ethyl acetate
EDCl 1-ethyl-3-(3-dimethylaminopropyl)carbodiimide
h hour
HOBt hydroxybenzotriazole
HPLC high pressure liquid chromatography
LCMS liquid chromatography mass spectrometry
M molarity
min minute
N normality
NMI N-methyl imidazole
PE petroleum ether
Rf retention factor
rt room temperature
Rt retention time
TCFH 1-chloro-N,N,N',N'-tetranethylfornamidinium hexafluorophosphate
TFA trifluoro acetic acid
THE tetrahydrofuran

SYNTHETIC EXAMPLES

The following Examples describe the synthesis of compounds of Formula (Ia), wherein n is 4-9.

Example S1. Synthesis of Intermediate Compound I-1

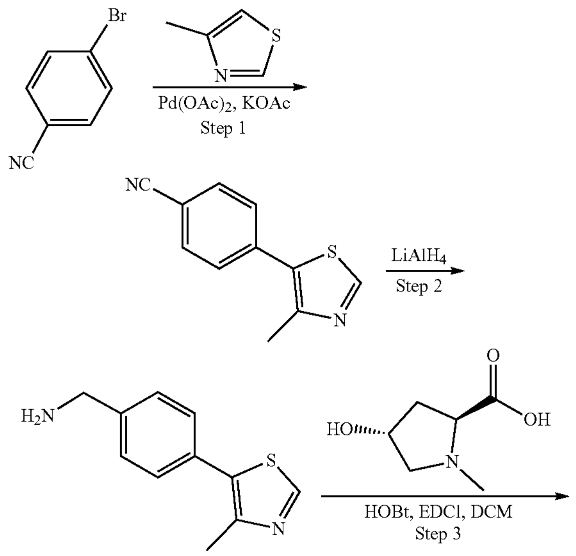

-continued

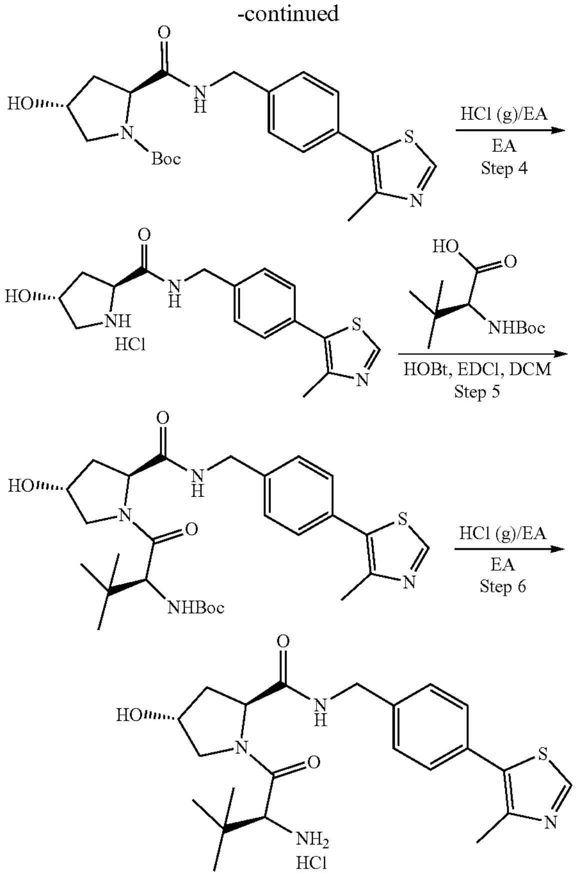

I-1

Step 1. Synthesis of 4-(4-methylthiazol-5-yl)benzonitrile

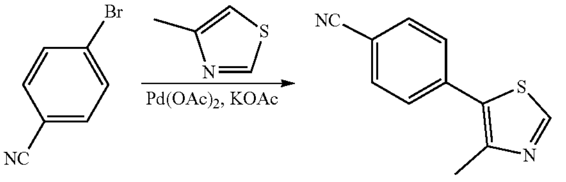

Two batches: To a solution of 4-bromobenzonitrile (300 g, 1.65 mol) in N,N-dimethylacetamide (3000 mL) was added 4-methylthiazole (180 g, 1.81 mol) and potassium acetate (323 g, 3.30 mol). To the reaction mixture was added palladium acetate (18.5 g, 82.4 mmol) under nitrogen atmosphere. The reaction mixture was stirred at 150° C. for 5 h. LCMS (Rt (product)=1.27 min) indicated that the reaction was finished. The reaction mixture was diluted with water (4000 mL) and extracted with ethyl acetate (4000 mL×2). The organic layers were combined, washed with brine (2000 mL), dried over sodium sulfate, filtered and concentrated. The crude was washed with (petroleum ether/ethyl acetate, 10:1, 1500 mL×3), the reaction mixture was filtered and the filtrate was concentrated to give 4-(4-methylthiazol-5-yl) benzonitrile (590 g, 89.4% yield) as a yellow oil.

LCMS: Rt (product)=1.27 min.

HPLC: Rt=2.56 min, 88% purity at 220 nm.

Step 2. Synthesis of [4-(4-methylthiazol-5-yl)phenyl]methanamine

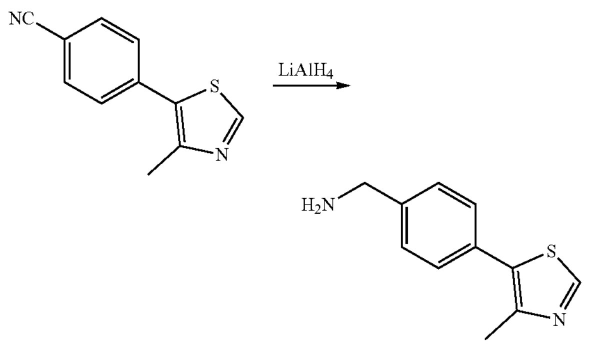

Five batches: To a stirred solution of 4-(4-methylthiazol-5-yl)benzonitrile (100 g, 499 mmol) in dry tetrahydrofuran (2500 mL) was added $LiAlH_4$ (38 g, 1.00 mol) in portions at 0° C. in 10 min under nitrogen atmosphere. The reaction mixture was stirred at 60° C. for 3 h. LCMS (Rt (product) =0.30 min) indicated that the reaction was finished. The reaction mixture was cooled to 10° C., water (38 mL) was added, then 15% solution of NaOH (76 mL) was added, and water (38 mL) was added. Then the mixture was filtered and the filtrate concentrated. The crude was combined, and water (3000 mL) was added slowly and then extracted with ethyl acetate (3000 mL×3). The combined organic phase was washed with brine (1500 mL), dried over anhydrous $Na_2SO_4$, filtered and concentrated to give [4-(4-methylthiazol-5-yl)phenyl]methanamine (275 g, crude) as red oil.

LCMS: Rt (product)=0.30 min.

HPLC: Rt (product)=2.33 min, 70% purity at 220 nm.

Step 3. Synthesis of tert-butyl (2S,4R)-4-hydroxy-2-[[4-(4-methylthiazol-5-yl)phenyl]methylcarbamoyl]pyrrolidine-1-carboxylate

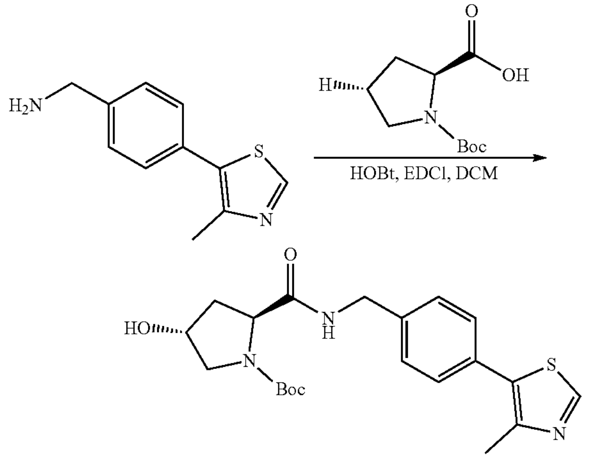

Two batches: To a solution of [4-(4-methylthiazol-5-yl)phenyl]methanamine (111.5 g, crude) in dichloromethane (1200 mL) was added HOBt (81.1 g, 600 mmol), EDCI (115 g, 600 mmol), DIEA (106 g, 818 mmol), and (2S,4R)-1-tert-butoxycarbonyl-4-hydroxy-pyrrolidine-2-carboxylic acid (151 g, 655 mmol) at 25° C. The reaction mixture was stirred at 25° C. for 16 h. LCMS (Rt (product)=1.1 min) indicated that the reaction was finished. The reaction mixtures were combined. Water (1000 mL) was added and separated. The organic phase was washed with brine (500 mL), dried with anhydrous $Na_2SO_4$, filtered, and concentrated in vacuum. The residue was combined purified by silica gel chromatography (petroleum ether/ethyl acetate, 2:1 to 0:1) to give tert-butyl (2S,4R)-4-hydroxy-2-[[4-(4-methylthiazol-5-yl)phenyl]methylcarbamoyl]pyrrolidine-1-carboxylate (110 g, 24.14% yield) as a yellow solid.

LCMS: Rt (product)=1.1 min.

HPLC: Rt=2.33 min, 85% purity at 220 nm.

Step 4. Synthesis of (2S,4R)-4-hydroxy-N-[[4-(4-methylthiazol-5-yl)phenyl]methyl]pyrrolidine-2-carboxamide

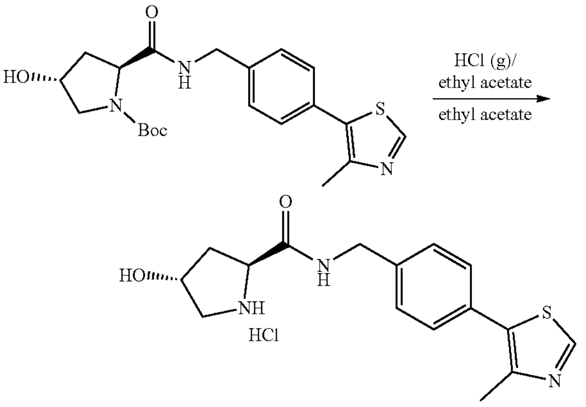

To a solution of tert-butyl (2S,4R)-4-hydroxy-2-[[4-(4-methylthiazol-5-yl)phenyl]methylcarbamoyl]pyrrolidine-1-carboxylate (110 g, 263 mmol) in ethyl acetate (1.2 L) was added HCl(g)/ethyl acetate (4 M, 528 mL) dropwise at 0-5° C. The reaction mixture was stirred at 25° C. for 4 h. TLC (Petroleum ether/Ethyl acetate=0/1, Rf (reactant)=0.20, Rf (product)=0.00) showed only trace amount of starting material remained. The mixture was filtered, and the filter cake was washed with ethyl acetate (200 mL). The solid was dried in vacuum to give (2S,4R)-4-hydroxy-N-[[4-(4-methylthiazol-5-yl)phenyl]methyl]pyrrolidine-2-carboxamide hydrochloride (104 g, crude) as white solid.

HPLC: Rt (product)=1.33 min, 92.89% purity at 220 nm.

Step 5. Synthesis of tert-butyl N-[(1S)-1-[(2S,4R)-4-hydroxy-2-[[4-(4-methylthiazol-5-yl)phenyl]methylcarbamoyl]pyrrolidine-1-carbonyl]-2,2-dimethylpropyl]carbamate

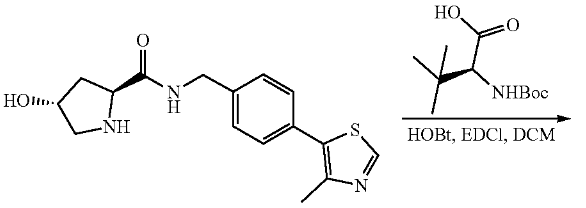

-continued

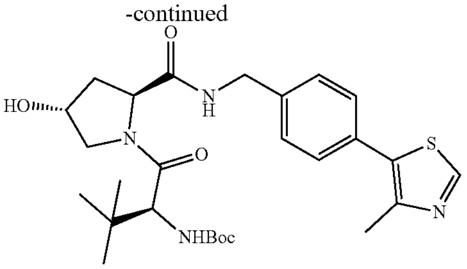

To a solution of (2S,4R)-4-hydroxy-N-[[4-(4-methylthiazol-5-yl)phenyl]methyl]pyrrolidine-2-carboxamide (104 g, crude) in dichloromethane (30 mL) was added HOBt (43.68 g, 323 mmol), EDCI (61.9 g, 323 mmol), DIEA (113.95 g, 881.69 mmol), and (2S)-2-(tert-butoxycarbonylamino)-3,3-dimethyl-butanoic acid (81.6 g, 353 mmol) at 25° C. The reaction mixture was stirred at 25° C. for 16 h. LCMS (Rt (product)=1.28 min) indicated that the reaction was finished. Water (1000 mL) was added and separated. The organic phase was washed with brine (500 mL), dried with anhydrous $Na_2SO_4$, filtered, and concentrated under vacuum. The residue was purified by silica gel chromatography (petroleum ether/ethyl acetate, 2:1 to 0:1) to give tert-butyl N-[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]carbamate (70 g, 44.9% yield) as colorless oil.

LCMS: Rt (product)=1.28 min, $[M+H]^+$ 531.50.

$^1H$ NMR: 400 MHz DMSO-$d_6$ δ: 8.98 (s, 1H), 8.56 (t, J=5.6 Hz, 1H), 7.44-7.38 (m, 4H), 6.46 (d, J=9.2 Hz, 1H), 5.14 (s, 1H), 4.45-4.14 (m, 5H), 3.66-3.61 (m, 2H), 2.44 (s, 3H), 2.04-1.89 (m, 2H), 1.38 (s, 9H), 0.93 (s, 9H).

Step 6. Synthesis of (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide

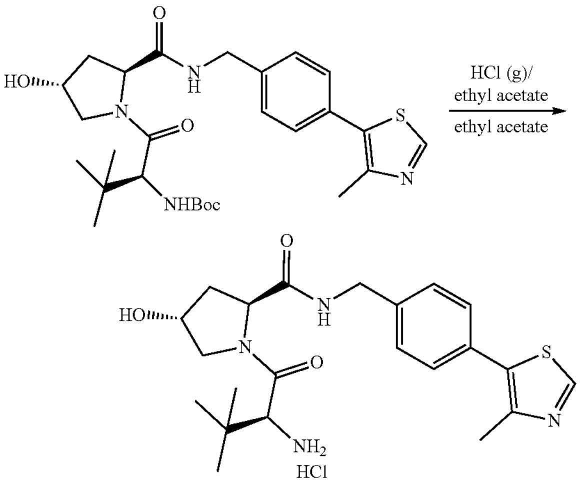

I-1

To a solution of tert-butyl N-[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]carbamate (71.8 g, 135 mmol) in ethyl acetate (7000 mL) was added HCl (g)/ethyl acetate (4 M, 33.82 mL) at 25° C., and the reaction mixture was stirred at 25° C. for 2 h. TLC (ethyl acetate, Rf (product)=0) indicated that the reaction was finished. The reaction mixture was filtered and the and the solid was washed with ethyl acetate (500 mL) and acetonitrile (300 mL) to give (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (I-1) (56.6 g, 89.6% yield, HCl) as a light-yellow solid.

$^1H$ NMR: 400 MHz DMSO-$d_6$ δ: 9.05 (s, 1H), 8.74 (t, J=6.0 Hz, 1H), 8.14 (d, J=4.0 Hz, 3H), 7.40 (s, 4H), 4.57-4.53 (m, 1H), 4.44-4.37 (m, 2H), 4.27-4.25 (m, 1H), 3.90 (d, J=5.6 Hz, 1H), 3.77 (d, J=11.2 Hz, 1H), 3.57-3.54 (m, 1H), 2.45 (s, 3H), 2.13-2.09 (m, 1H), 1.90-1.86 (m, 1H), 1.02 (s, 9H).

Example S2. Synthesis of Intermediate Compound tert-butyl 2-cyclopentyl-4-(7-hydroxyquinazolin-4-yl)benzoate

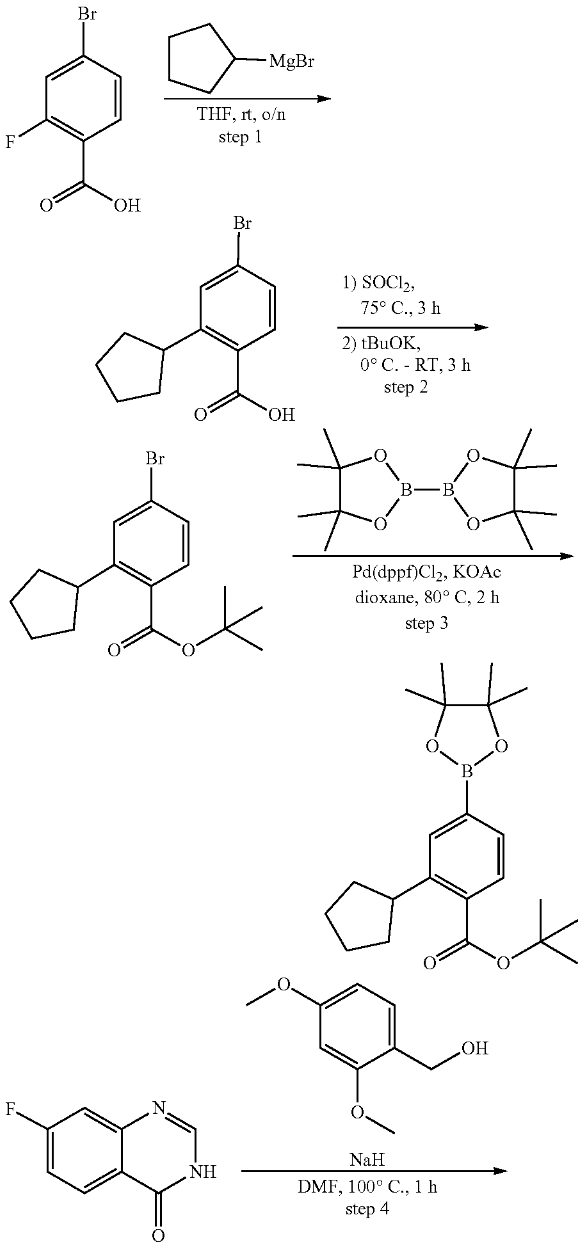

-continued

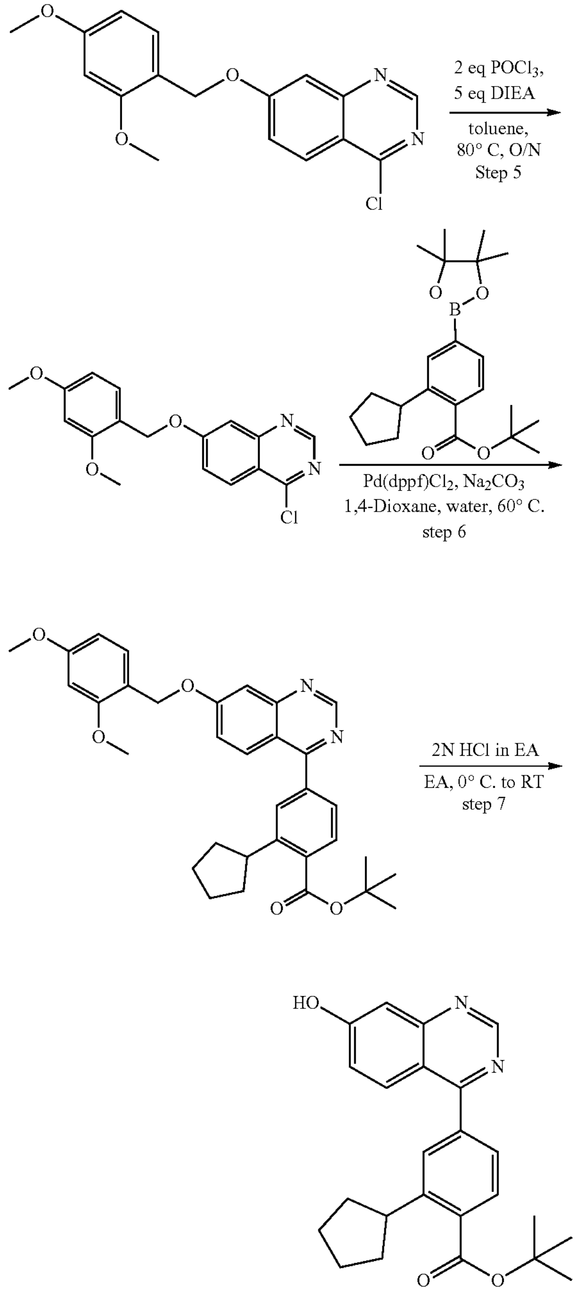

Step 1. Synthesis of 4-bromo-2-cyclopentyl-benzoic acid

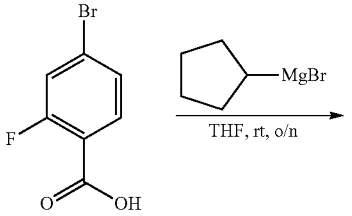

-continued

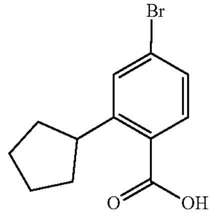

Into a 500 mL round bottom flask, to a stirred solution of 4-bromo-2-fluoro-benzoic acid (10.0 g, 45.66 mmol) in THF (100 mL) was added bromo(cyclopentyl)magnesium (114.15 mL, 114.15 mmol) dropwise at 0° C. under a nitrogen atmosphere. Upon complete addition, the resulting mixture was warmed to room temperature and stirred for overnight. The mixture was quenched by water at 0° C. and concentrated under reduced pressure. The mixture was filtered and the filtrate was collected. The pH value of the solution was adjusted to 3 with HCl (1 mol/L). The mixture was filtered. The filter cake was collected and concentrated under vacuum to give 4-bromo-2-cyclopentyl-benzoic acid (7.25 g, 59%) as an off-white solid. MS: m/z: Calc'd for $C_{12}H_{13}BrO_2$, $[M-H]^-$ 267; Found 267 $[M-H]^-$.

Step 2. Synthesis of tert-butyl 4-bromo-2-cyclopentyl-benzoate

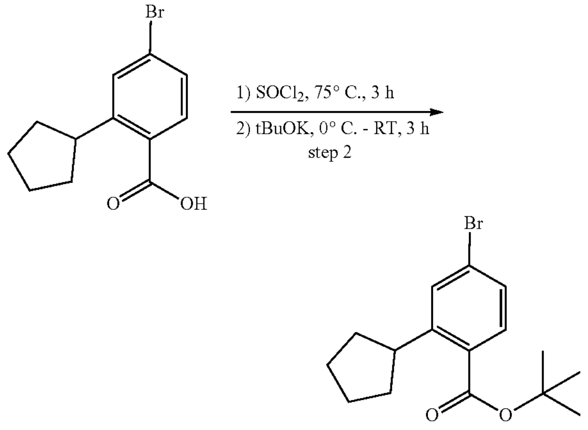

A solution of 4-bromo-2-cyclopentyl-benzoic acid (10 g, 37.17 mmol) in $SOCl_2$ (50 mL, 685.47 mmol) was stirred at 75° C. for 3 h. The resulting solution was concentrated to remove excess $SOCl_2$ to obtain 4-bromo-2-cyclopentyl-benzoyl chloride. Then to a stirred solution of t-BuOK (5841 mg, 52.16 mmol) in THE (100 mL) was added a solution of 4-bromo-2-cyclopentyl-benzoyl chloride in THE (50 mL) at 0° C. The reaction mixture was stirred at room temperature for 1 h. The resulting mixture was concentrated and the residue was added with water, extracted with EA, washed with brine, and the combined organic layers were dried over sodium sulfate, filtered and concentrated. The resulting residue was purified by column chromatography to obtain tert-butyl 4-bromo-2-cyclopentyl-benzoate (8 g, 66.2% yield) as an off-white solid.

Step 3. Synthesis of tert-butyl 2-cyclopentyl-4-(4,4,5,5-tetramethyl-1,3,2-dioxaborolan-2-yl)benzoate

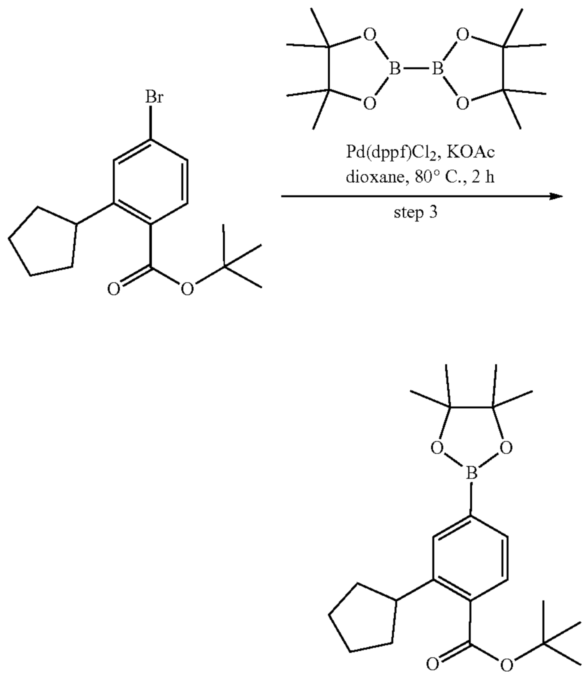

To a stirred solution of 4,4,5,5-tetramethyl-2-(4,4,5,5-tetramethyl-1,3,2-dioxaborolan-2-yl)-1,3,2-dioxaborolane (11.24 g, 44.27 mmol) in 1,4-dioxane (100 mL) were added tert-butyl 4-bromo-2-cyclopentyl-benzoate (12 g, 36.9 mmol) and Pd(dppf)$Cl_2$ (2.5 g, 3.41 mmol) at room temperature. The reaction mixture was purged with $N_2$ and stirred at 80° C. for 2 h. The reaction mixture was concentrated and the residue was purified by silica gel column to obtain tert-butyl 2-cyclopentyl-4-(4,4,5,5-tetramethyl-1,3,2-dioxaborolan-2-yl)benzoate (9 g, 65.5% yield) as a white solid. $^1$H NMR (300 MHz, $CDCl_3$) δ 7.81 (s, 1H), 7.63 (m, 1H), 7.55 (m, 1H), 3.67-3.48 (m, 1H), 2.07 (m, 2H), 1.92-1.78 (m, 2H), 1.78-1.66 (m, 4H), 1.60 (s, 10H), 1.35 (s, 12H).

Step 4. Synthesis of 7-[(2,4-dimethoxyphenyl)methoxy]-3H-quinazolin-4-one

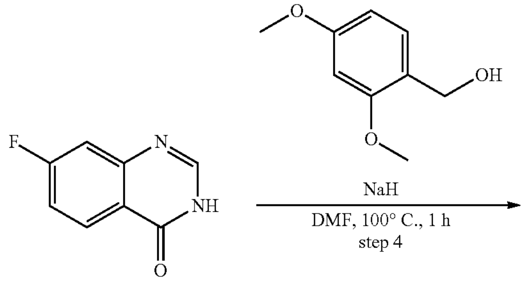

-continued

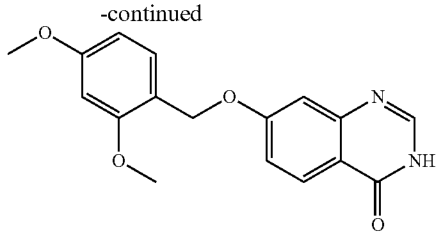

To a stirred solution of (2,4-dimethoxyphenyl)methanol (46 g, 274.16 mmol) in DMF (150 mL) was added 60% NaH (6.58 g, 274.16 mmol) at 0° C. portion-wise and the resulting suspension was warmed to room temperature for 30 min. Then 7-fluoro-3H-quinazolin-4-one (15 g, 91.39 mmol) was added to the above reaction mixture, and the resulting reaction was stirred at 100° C. for 1 h. The reaction mixture was quenched with water at 0° C., adjusted pH value to 6~7 with 1 N HCl, and filtered. The filter cake was collected and slurry with EA to obtain 7-[(2,4-dimethoxyphenyl)methoxy]-3H-quinazolin-4-one (22 g, 77.1% yield) as a white solid. MS: m/z: Calc'd for $C_{17}H_{16}N_2O_4$ $[M+H]^+$ 313, found 313.

Step 5. Synthesis of 4-chloro-7-[(2,4-dimethoxyphenyl)methoxy]quinazoline

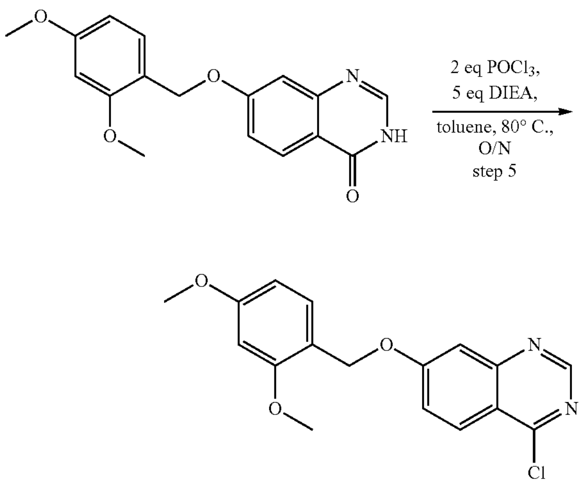

To a stirred solution of 7-[(2,4-dimethoxyphenyl)methoxy]-3H-quinazolin-4-one (22 g, 70.44 mmol) and DIEA (61.35 mL, 352.2 mmol) in toluene (150 mL) was added $POCl_3$ (13.13 mL, 140.88 mmol) dropwise at 0° C. The resulting mixture was warmed to room temperature, and then stirred at 80° C. overnight. After cooling to room temperature, the mixture was azeotroped with toluene, and the residue was taken up in EA. The organic phase was washed with saturated $NaHCO_3$, dried over sodium sulfate, filtered and concentrated. The crude product was purified by a silica gel column chromatography to obtain 4-chloro-7-[(2,4-dimethoxyphenyl)methoxy]quinazoline (17 g, 72.9% yield) as a yellow solid. MS: m/z: Calc'd for $C_{17}H_{15}ClN_2O_3$ $[M+H]^+$ 331, found 331.

Step 6. Synthesis of tert-butyl 2-cyclopentyl-4-[7-[(2,4-dimethoxyphenyl)methoxy]quinazolin-4-yl]benzoate

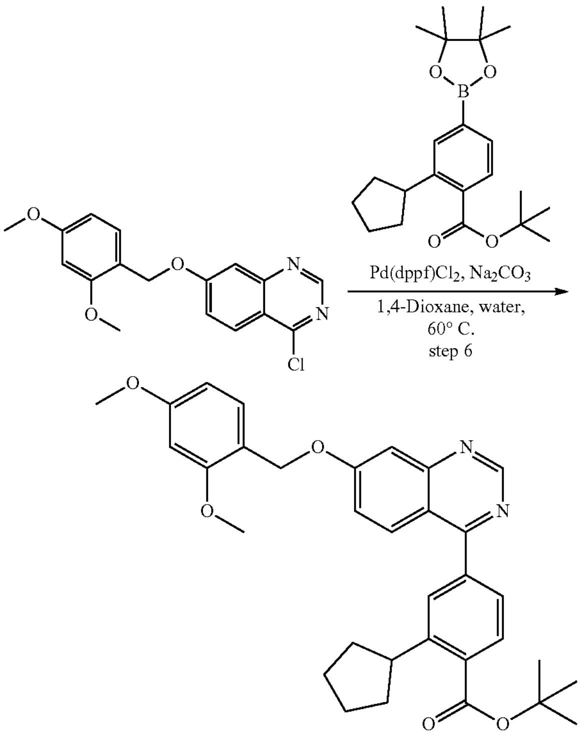

To a stirred solution of 4-chloro-7-[(2,4-dimethoxyphenyl)methoxy]quinazoline (22 g, 66.51 mmol) in 1,4-dioxane (200 mL) and water (40 mL) were added Pd(dppf)$Cl_2CH_2Cl_2$ (5.43 g, 6.65 mmol), $Na_2CO_3$ (21.15 g, 199.53 mmol) and tert-butyl-2-cyclopentyl-4-(4,4,5,5-tetramethyl-1,3,2-dioxaborolan-2-yl)benzoate (29.72 g, 79.81 mmol) at room temperature. The resulting mixture was purged with $N_2$ and stirred at 60° C. for 2 h. The reaction mixture was filtered and concentrated. The crude product was purified by a silica gel column chromatography to obtain tert-butyl 2-cyclopentyl-4-[7-[(2,4-dimethoxyphenyl)methoxy]quinazolin-4-yl]benzoate (31 g, 86.2% yield) as a light-yellow oil. MS: m/z: Calc'd for $C_{33}H_{36}N_2O_5$ $[M+H]^+$ 541, found 541.

Step 7. Synthesis of tert-butyl 2-cyclopentyl-4-(7-hydroxyquinazolin-4-yl)benzoate

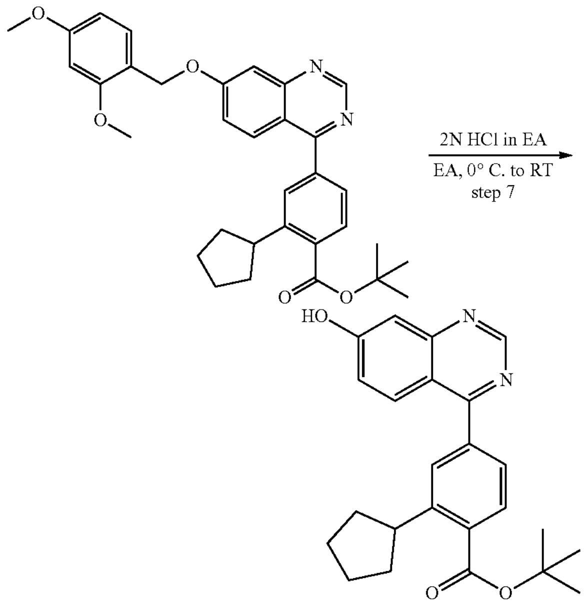

To a stirred solution of tert-butyl 2-cyclopentyl-4-[7-[(2,4-dimethoxyphenyl)methoxy]quinazolin-4-yl]benzoate (31 g, 57.34 mmol) in EA (300 mL) was added 2 N HCl (EA) (200 mL, 57.34 mmol) slowly at 0° C. The resulting mixture was warmed to room temperature and stirred for 3 h. After completion of the reaction as per TLC and LCMS, pH value of the reaction mixture was adjusted to 6-7 with sat. $NaHCO_3$ at 0° C. extracted with EA and washed with $H_2O$. The combined extracts were dried over sodium sulfate, filtered and concentrated. The crude was purified by silica gel column chromatography to obtain tert-butyl 2-cyclopentyl-4-(7-hydroxyquinazolin-4-yl)benzoate (17 g, 75.9% yield) as a yellow solid. MS: m/z: Calc'd for $C_{24}H_{26}N_2O_3$ [M+H]*391, found 391.

Example S3. Synthesis of Compound 6 (n=4)

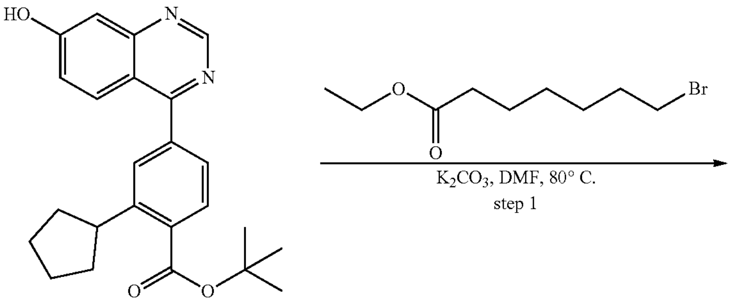

-continued
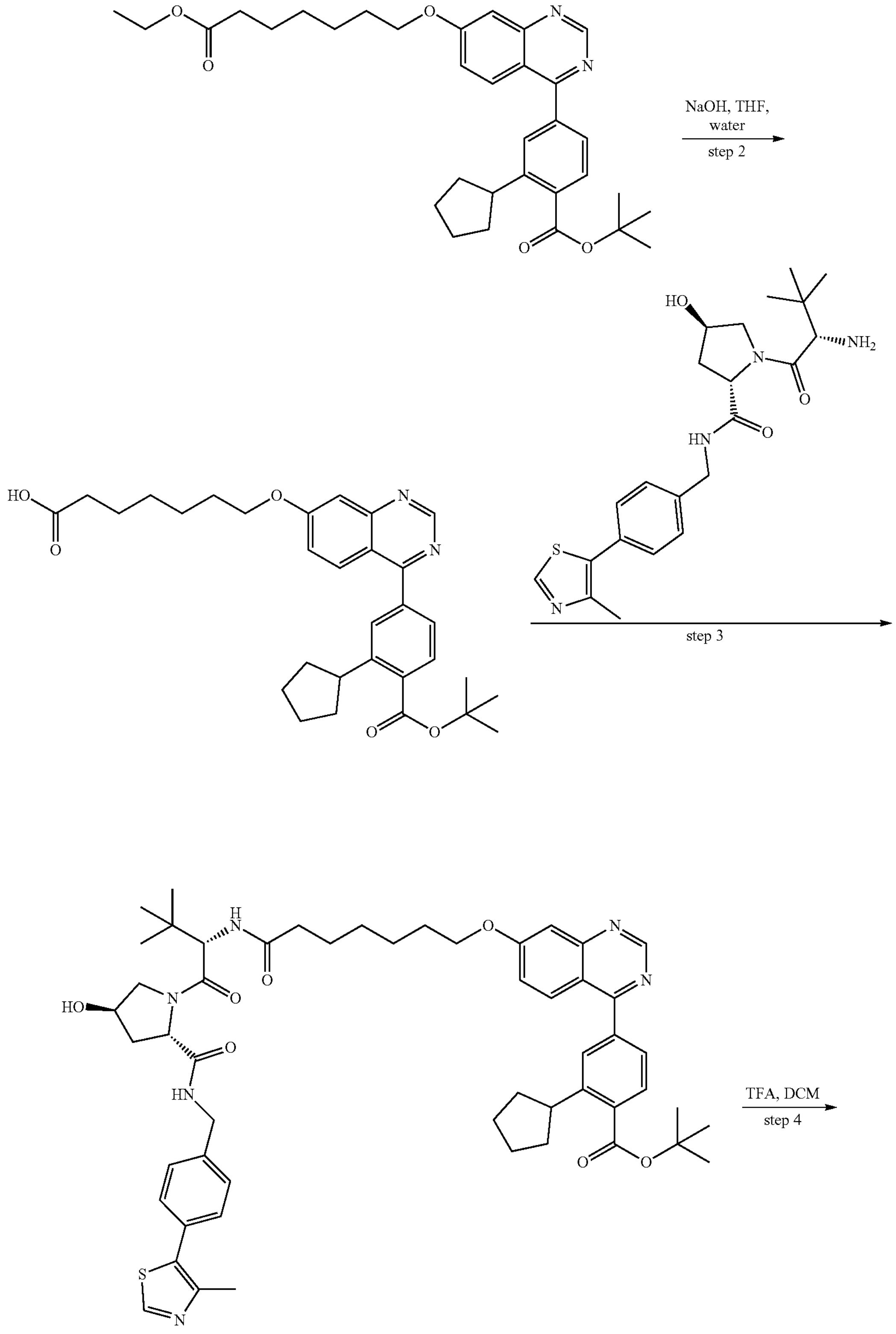

-continued

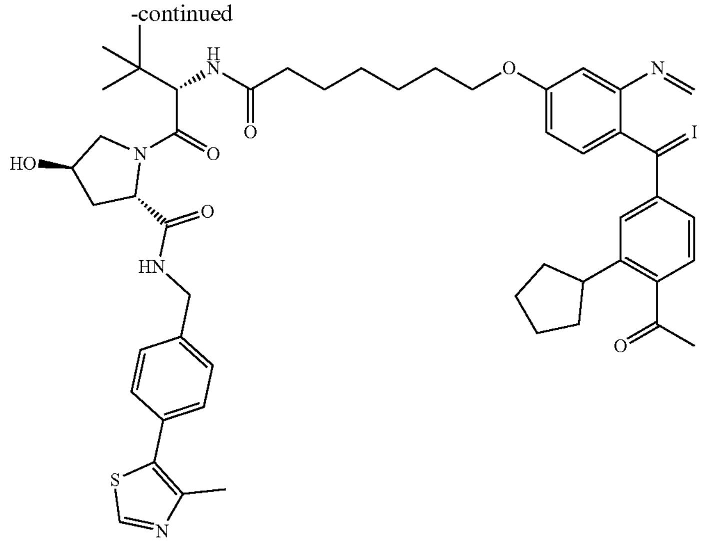

6

Step 1. Synthesis of tert-butyl 2-cyclopentyl-4-[7-(7-ethoxy-7-oxo-heptoxy)quinazolin-4-yl]benzoate

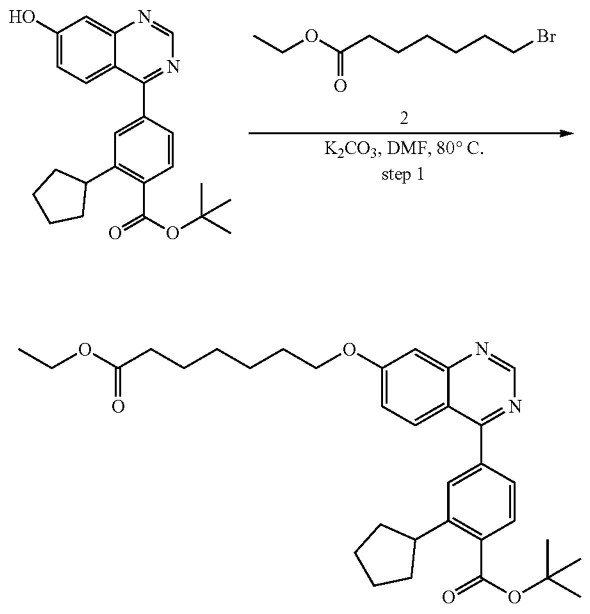

To a stirred solution of tert-butyl 2-cyclopentyl-4-(7-hydroxyquinazolin-4-yl)benzoate (250 mg, 0.64 mmol) in DMF (3 mL) was added ethyl 7-bromoheptanoate (182.19 mg, 0.77 mmol) and $K_2CO_3$ (169.67 mg, 1.6 mmol) at room temperature, and the resulting mixture was stirred at 80° C. for 2 h. The reaction mixture was quenched with water, and extracted with EA. The organic layer was washed with brine, concentrated and purified by column chromatography (PE/EA=5:4) to afford tert-butyl 2-cyclopentyl-4-[7-(7-ethoxy-7-oxo-heptoxy)quinazolin-4-yl]benzoate (320 mg, 86.39% yield) as a light-yellow oil.

MS: m/z: Calc'd for $C_{33}H_{42}N_2O_5$ $[M+H]^+$ 547, found $[M+H]^+$ 547.40.

Step 2. Synthesis of 7-[4-(4-tert-butoxycarbonyl-3-cyclopentyl-phenyl)quinazolin-7-yl]oxyheptanoic acid

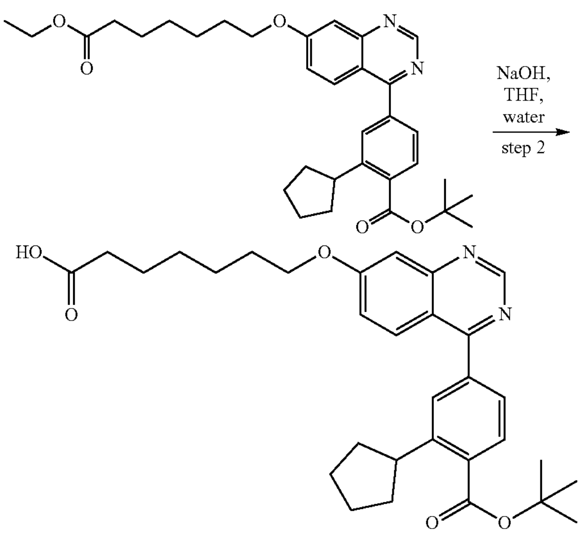

To a stirred solution of tert-butyl 2-cyclopentyl-4-[7-(7-ethoxy-7-oxo-heptoxy)quinazolin-4-yl]benzoate (310 mg, 0.57 mmol) in THF (3 mL) and water (0.60 mL) was added LiOH (67.9 mg, 2.84 mmol) at room temperature, and the resulting mixture was stirred at 60° C. for 3 h. The reaction mixture was concentrated. The residue was diluted with water and acidified to pH ~5 with 1 M HCl. The resulting precipitate was filtered, and the filter cake was washed with $H_2O$ (2×2 mL). The filter cake was dried in vacuo to give 7-[4-(4-tert-butoxycarbonyl-3-cyclopentyl-phenyl)quinazolin-7-yl]oxyheptanoic acid (290 mg, 92.39% yield) as a white solid.

MS: m/z: Calc'd for $C_{31}H_{38}N_2O_5$ $[M+H]^+$ 519, found 519.20 $[M+H]^+$.

Step 3. Synthesis of tert-butyl 2-cyclopentyl-4-[7-[7-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-7-oxo-heptoxy]quinazolin-4-yl]benzoate

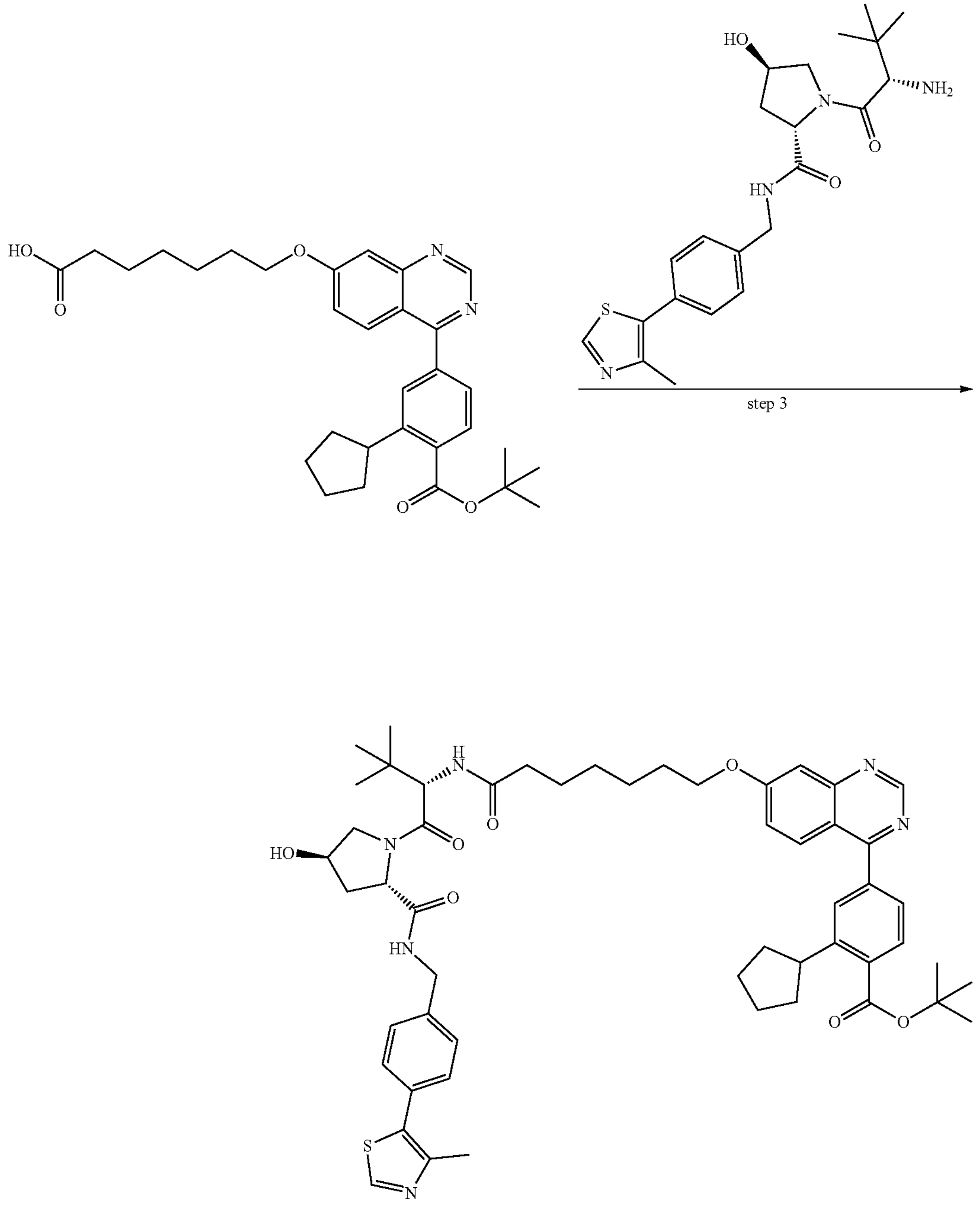

To a stirred solution of 7-[4-(4-tert-butoxycarbonyl-3-cyclopentyl-phenyl)quinazolin-7-yl]oxyheptanoic acid (50 mg, 0.10 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (I-1 from Example S1) (41.51 mg, 0.10 mmol) in DMF (2 mL) were added HATU (54.98 mg, 0.14 mmol) and DIEA (0.04 mL, 0.29 mmol), and the resulting mixture was stirred at room temperature for 2 h. The reaction mixture was purified by reverse flash chromatography to obtain tert-butyl 2-cyclopentyl-4-[7-[7-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-7-oxo-heptoxy]quinazolin-4-yl]benzoate (85 mg, 94.68% yield) as a white oil.

MS: m/z: Calc'd for $C_{53}H_{66}N_6O_7S$ $[M+H]^+$ 931; Found, 931 $[M+H]^+$.

Step 4. Synthesis of 2-cyclopentyl-4-[7-[7-oxo-7-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]heptoxy]quinazolin-4-yl]benzoic acid (Compound 6)

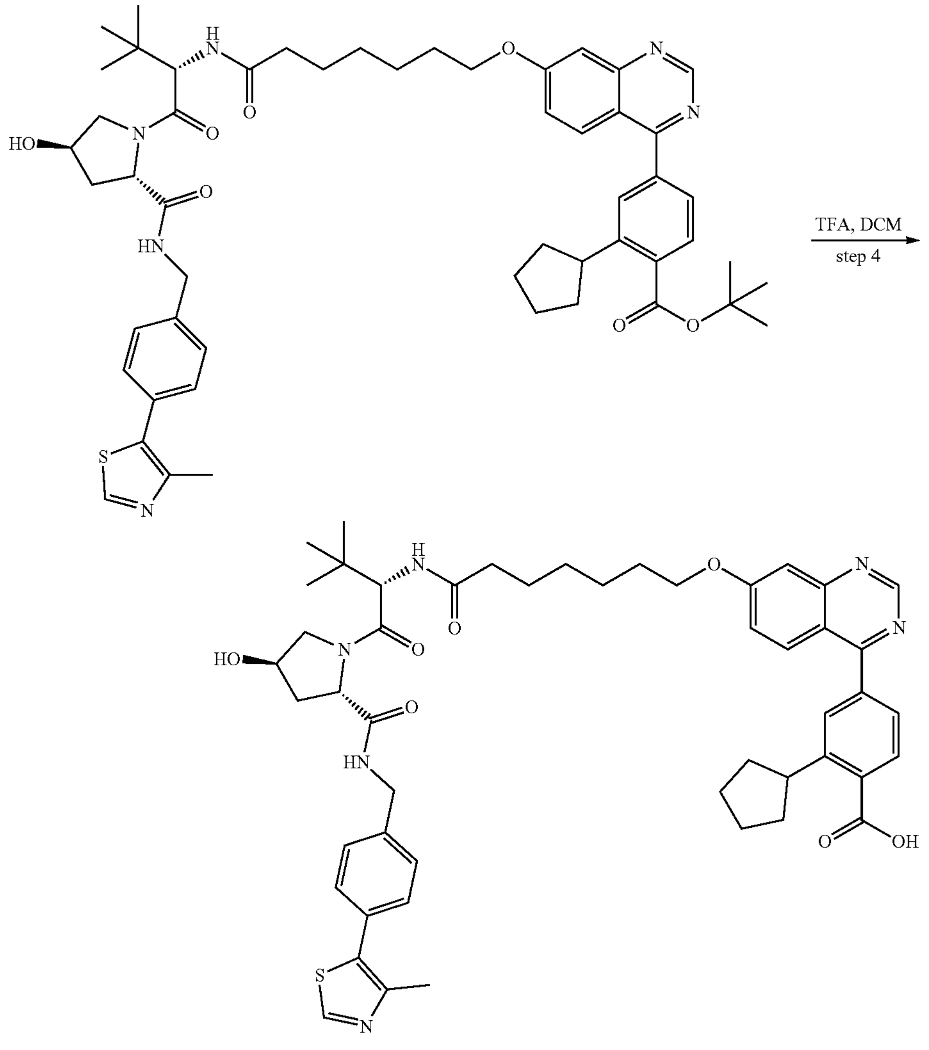

6

To a stirred solution of tert-butyl 2-cyclopentyl-4-[7-[7-oxo-7-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]heptoxy]quinazolin-4-yl]benzoate (80.17 mg, 0.09 mmol) in DCM (2 mL) was added TFA (1 mL) at 0° C. and the reaction mixture was stirred at room temperature for 2 h. The reaction mixture was concentrated. The residue was purified by Prep-HPLC to obtain 2-cyclopentyl-4-[7-[7-oxo-7-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]heptoxy]quinazolin-4-yl]benzoic acid (Compound 6) (34.9 mg, 46.09% yield) as a white solid.

MS: m/z: Calc'd for $C_{49}H_{58}N_6O_7S$ $[M+H]^+$ 875.4; Found, 875.3 $[M+H]^+$.

$^1H$ NMR (400 MHz, Methanol-d4) δ 9.21 (s, 1H), 8.97 (s, 1H), 8.03 (d, J=9.3 Hz, 1H), 7.95 (d, J=8.0 Hz, 1H), 7.83 (d, J=1.7 Hz, 1H), 7.64 (dd, J=8.0, 1.8 Hz, 1H), 7.52-7.38 (m, 6H), 4.65 (s, 1H), 4.63-4.49 (m, 3H), 4.37 (d, J=15.5 Hz, 1H), 4.27 (t, J=6.4 Hz, 2H), 3.93 (d, J=10.4 Hz, 2H), 3.82 (dd, J=11.0, 3.8 Hz, 1H), 2.49 (s, 3H), 2.42-2.24 (m, 2H), 2.20 (t, J=11.6 Hz, 3H), 2.10 (t, J=13.4 Hz, 1H), 1.93 (t, J=7.3 Hz, 2H), 1.87 (s, 2H), 1.78-1.68 (m, 6H), 1.59 (p, J=7.1 Hz, 2H), 1.47 (d, J=7.6 Hz, 2H), 1.05 (s, 9H).

Prep-HPLC purification conditions: [Column: Sunfire prep C18 column, 30*150 mm, 5 μm; Mobile Phase A: water (0.05% TFA), Mobile Phase B: ACN; Flow rate: 60 mL/min; Gradient: 40% B to 60% B in 7 min; 254 nm; Rtl: 6.77.

Example S4: Synthesis of Compound 5 (n=5)

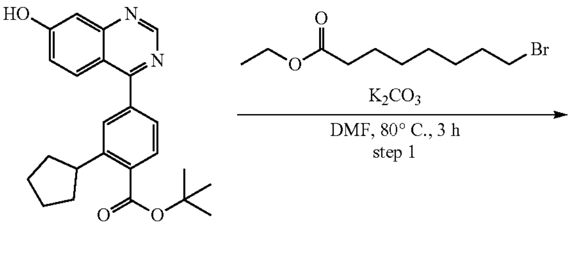

-continued

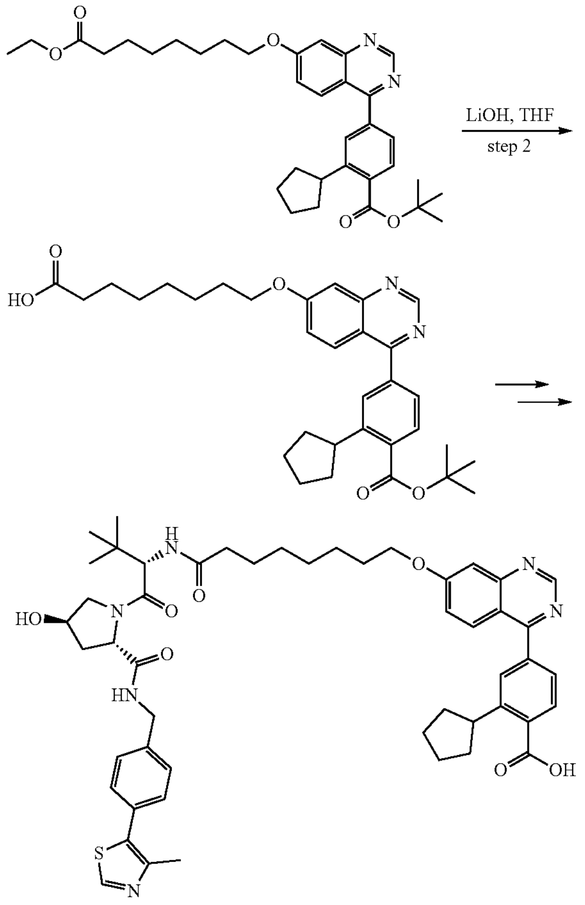

5

Step 1. Synthesis of tert-butyl 2-cyclopentyl-4-[7-(8-ethoxy-8-oxo-octoxy) quinazolin-4-yl]benzoate

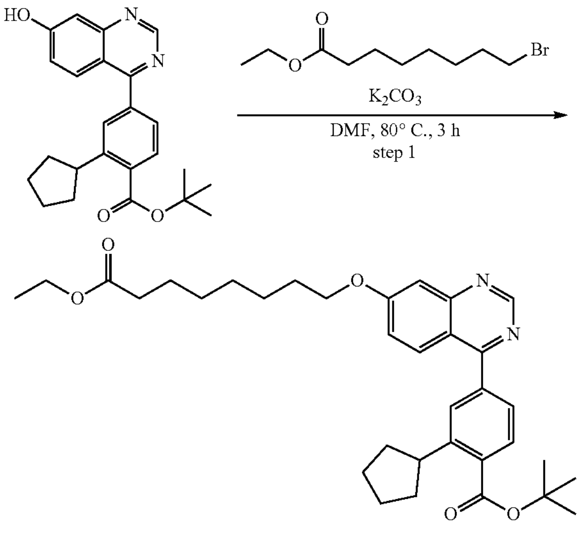

A mixture of tert-butyl 2-cyclopentyl-4-(7-hydroxyquinazolin-4-yl)benzoate (2.7 g, 6.91 mmol), $K_2CO_3$ (4.77 g, 34.57 mmol), and ethyl 8-bromooctanoate (8.68 g, 34.57 mmol) in DMF (100 mL) was stirred at 80° C. for 3 h. LCMS showed the reaction completed. The reaction mixture was diluted with EA and washed with brine 3-4 times. The combined organic layers were dried over sodium sulphate and concentrated. The product was passed though silica gel (PE/EA=1/1) to obtain tert-butyl 2-cyclopentyl-4-[7-(8-ethoxy-8-oxo-octoxy) quinazolin-4-yl]benzoate (2.5 g, 64.45% yield) as a colorless oil. MS: m/z: Calculated for $C_{34}H_{44}N_2O_5$, $[M+H]^+$ 561; Found 561.28.

Step 2. Synthesis of 8-[4-(4-tert-butoxycarbonyl-3-cyclopentyl-phenyl)quinazolin-7-yl]oxyoctanoic acid

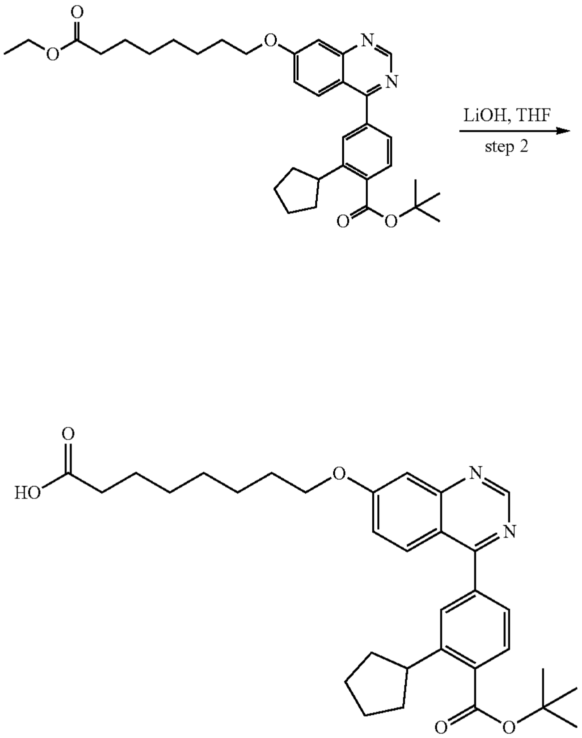

To a stirred solution of tert-butyl 2-cyclopentyl-4-[7-(8-ethoxy-8-oxo-octoxy)quinazolin-4-yl]benzoate (2.7 g, 4.82 mmol) in methanol (60 mL) and THE (60 mL) was added a solution of LiOH (576.62 mg, 24.08 mmol) in water (30 mL). The resulting mixture was stirred at room temperature overnight. LCMS showed the reaction completed. The reaction was diluted with water, the pH adjusted to between 4 and 5 with 1.0 N HCl. The product was extracted with EA, and the combined organic layers were dried over sodium sulphate and concentrated to afford 8-[4-(4-tert-butoxycarbonyl-3-cyclopentyl-phenyl)quinazolin-7-yl]oxyoctanoic acid (2.5 g, 97.47% yield) as a white solid. MS: m/z: Calculated for $C_{32}H_{40}N_2O_5$, $[M+H]^+$ 533; Found 533.20.

Synthesis of Compound 5. Compound 5 was prepared by following procedures similar to those described in Example S3.
Example S5: Synthesis of Compound 4 (n=6)
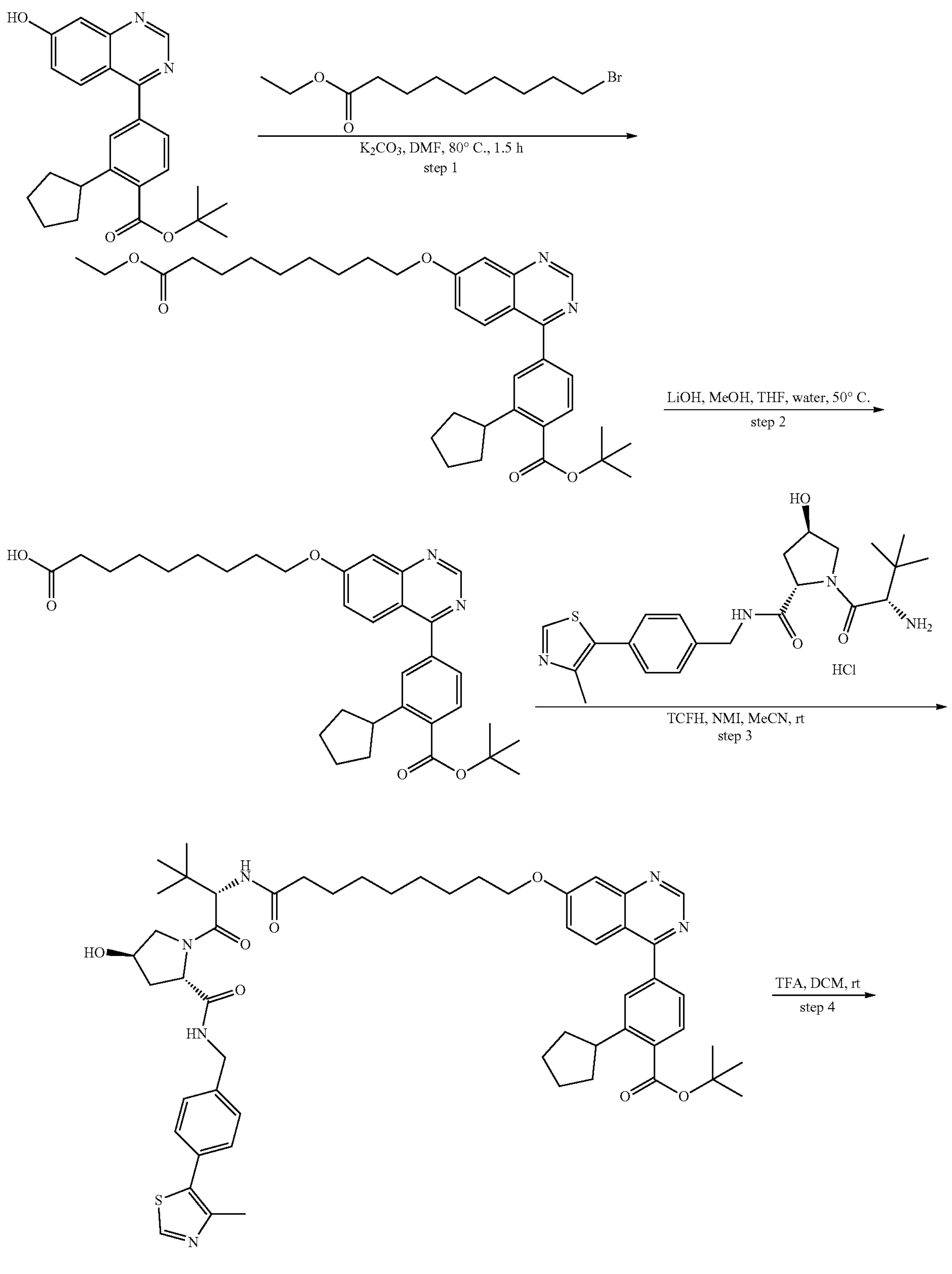

-continued

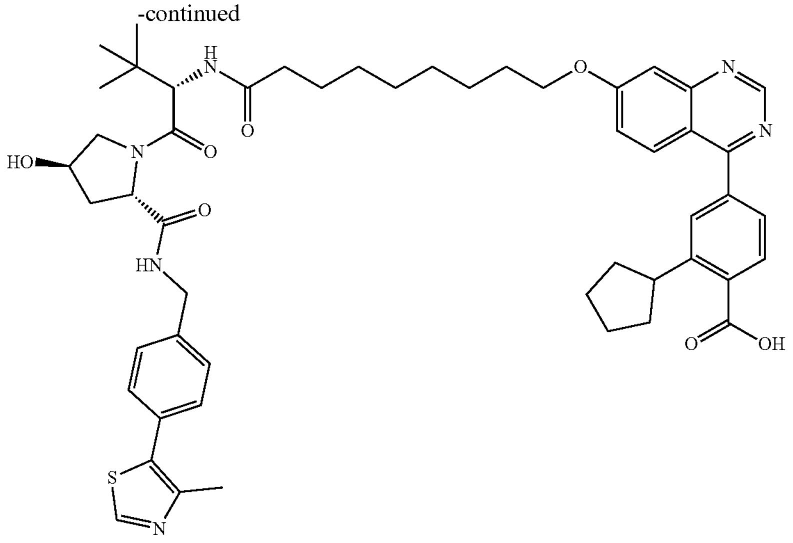

4

Step 1. Synthesis of tert-butyl 2-cyclopentyl-4-[7-(9-ethoxy-9-oxo-nonoxy)quinazolin-4-yl]benzoate

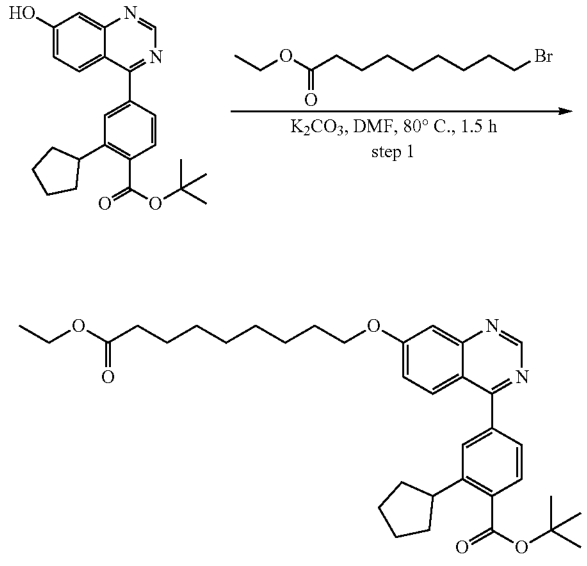

A mixture of tert-butyl 2-cyclopentyl-4-(7-hydroxyquinazolin-4-yl)benzoate (1500 mg, 3.84 mmol), ethyl 9-bromononanoate (1121 mg, 4.23 mmol) and $K_2CO_3$ (1222 mg, 11.52 mmol) in DMF (20 mL) was stirred at 80° C. for 1.5 h. Then the mixture was quenched with water and extracted with EA. The extracts were combined and dried over $Na_2SO_4$, filtered and concentrated. The obtained oil was purified by silica gel column chromatography using PE/EA (10-20%) as eluent. Pure fractions were combined and concentrated to obtain tert-butyl 2-cyclopentyl-4-[7-(9-ethoxy-9-oxo-nonoxy)quinazolin-4-yl]benzoate (1820 mg, 82.4% yield) as a light yellow oil. MS: m/z: Calc'd for $C_{35}H_{46}N_2O_5$ $[M+H]^+$ 575, found 575.40 $[M+H]^+$.

Step 2. Synthesis of 9-[4-(4-tert-butoxycarbonyl-3-cyclopentyl-phenyl)quinazolin-7-yl]oxynonanoic acid

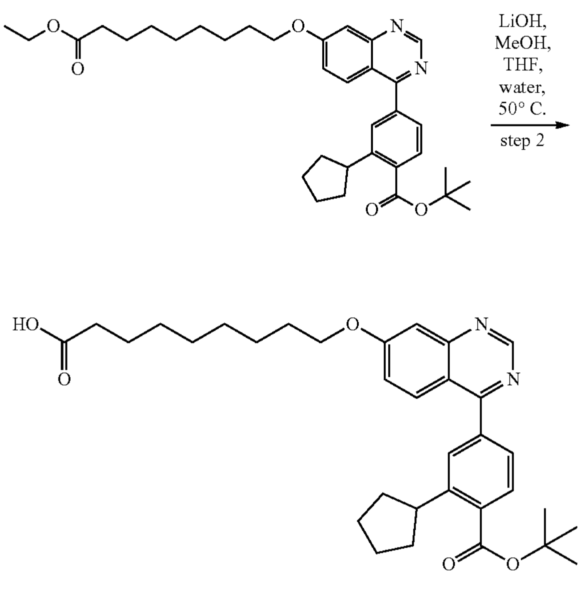

To a stirred solution of tert-butyl 2-cyclopentyl-4-[7-(9-ethoxy-9-oxo-nonoxy)quinazolin-4-yl]benzoate (1820 mg, 3.17 mmol) in MeOH (10 mL), THF (10 mL) and water (4 mL) was added LiOH (379.2 mg, 15.83 mmol) at room temperature. The resulting solution was stirred at 50° C. for 1.5 h. LCMS showed the reaction was completed. The reaction solution was concentrated, and the residue was purified by reverse flash chromatography (0.05% $NH_4HCO_3$/MeCN) to obtain 9-[4-(4-tert-butoxycarbonyl-3-cyclopentyl-phenyl)quinazolin-7-yl]oxynonanoic acid (1340 mg, 77.4% yield) as a white solid. MS: m/z: Calc'd for $C_{33}H_{42}N_2O_5$ $[M+H]^+$ 547, found 547.25 $[M+H]^+$.

Step 3. Synthesis of tert-butyl 2-cyclopentyl-4-[7-[9-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-9-oxo-nonoxy]quinazolin-4-yl]benzoate

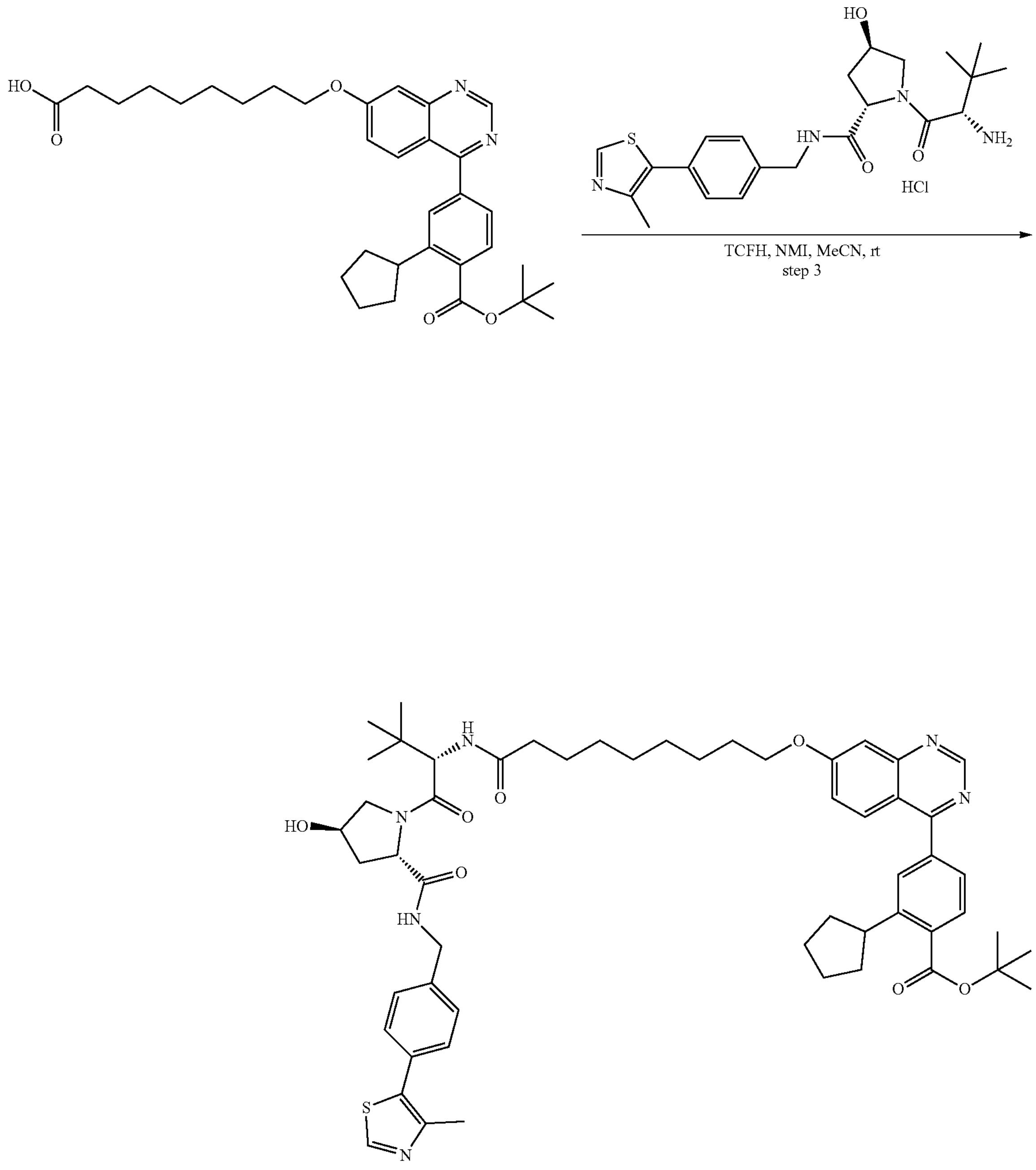

To a stirred solution of 9-[4-(4-tert-butoxycarbonyl-3-cyclopentyl-phenyl)quinazolin-7-yl]oxynonanoic acid (1340 mg, 2.45 mmol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (I-1 from Example S1) (1055 mg, 2.45 mmol) in MeCN (15 mL) were added TCFH (1375 mg, 4.9 mmol) and NMI (0.97 mL, 12.26 mmol). The resulting mixture was stirred at room temperature for 2 h. Then the reaction solution was concentrated, and the residue was purified by reverse flash chromatography (0.05% TFA/MeCN). Pure fractions were combined and concentrated to obtain tert-butyl 2-cyclopentyl-4-[7-[9-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-9-oxo-nonoxy]quinazolin-4-yl]benzoate (1700 mg, 72.3% yield) as a white solid. MS: m/z: Calc'd for $C_{55}H_{70}N_6O_7S$ $[M+H]^+$ 959, found 959.55 $[M+H]^+$.

Step 4. Synthesis of 2-cyclopentyl-4-[7-[9-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-9-oxo-nonoxy]quinazolin-4-yl]benzoic acid (4)

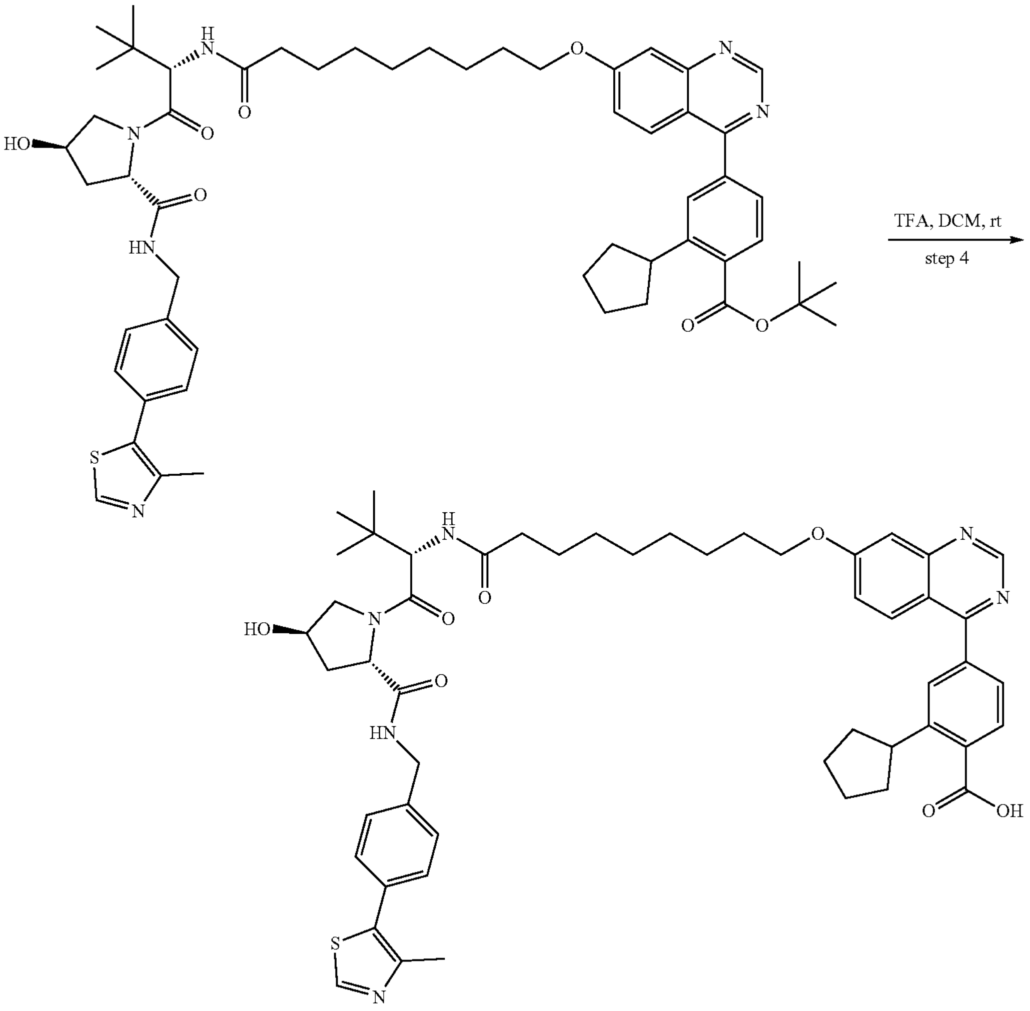

4

To a stirred solution of tert-butyl 2-cyclopentyl-4-[7-[9-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-9-oxo-nonoxy]quinazolin-4-yl]benzoate (1730 mg, 1.8 mmol) in DCM (4 mL) was added TFA (1 mL, 3.92 mmol) at 0° C. The resulting mixture was stirred at room temperature for 4 h. Then the reaction solution was concentrated and purified by reverse flash chromatography (0.05% $NH_4HCO_3$/MeCN, gradient: 10% MeCN to 20% MeCN in 20 min). Pure fractions were combined and concentrated to obtain 2-cyclopentyl-4-[7-[9-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-9-oxo-nonoxy]quinazolin-4-yl]benzoic acid (4) (982.5 mg, 59.9% yield) as a white solid. (Around 300 mg compound with 98% purity was further purified by Prep-HPLC after first reverse phase column purification, and the two batches were combined to afford 982.5 mg).

MS: m/z: Calc'd for $C_{51}H_{62}N_6O_7S$ $[M+H]^+$ 903, found 903.40 $[M+H]^+$.

$^1H$ NMR (400 MHz, Methanol-d4) δ 9.21 (s, 1H), 8.97 (s, 1H), 8.03 (d, J=9.2 Hz, 1H), 7.95 (d, J=8.0 Hz, 1H), 7.83 (d, J=1.7 Hz, 1H), 7.64 (dd, J=8.0, 1.8 Hz, 1H), 7.49 (m, 2H), 7.48-7.37 (m, 4H), 4.65 (s, 1H), 4.57-4.51 (m, 3H), 4.37 (m, 1H), 4.26 (t, J=6.4 Hz, 2H), 3.92-3.82 (m, 3H), 2.49 (s, 3H), 2.39-2.03 (m, 7H), 1.96-1.84 (m, 3H), 1.79-1.61 (m, 6H), 1.59-1.51 (m, 3H), 1.49-1.35 (m, 5H), 1.05 (s, 9H).

Prep-HPLC conditions: Column: XBridge Shield RP18 OBD Column, 30*150 mm, 5 μm; Mobile Phase A: water (10 mmol/L $NH_4HCO_3$+0.1% $NH_3 \cdot H_2O$), Mobile Phase B: ACN; Flow rate: 60 mL/min; Gradient: 9% B to 33% B in 7 min; 254/210 nm; Rtl: 5.93.

Example S6: Synthesis of Compound 3 (n=7)
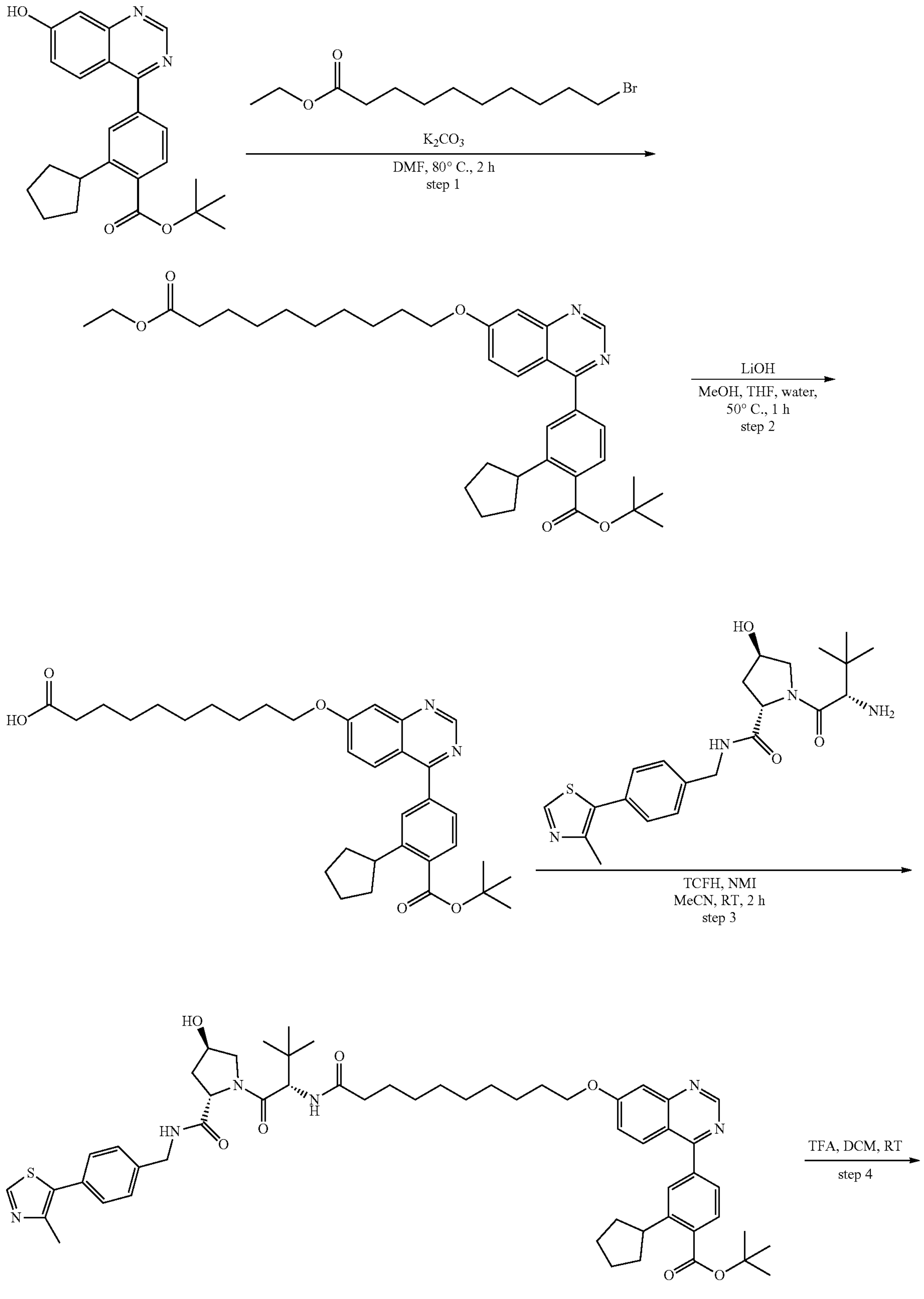

-continued

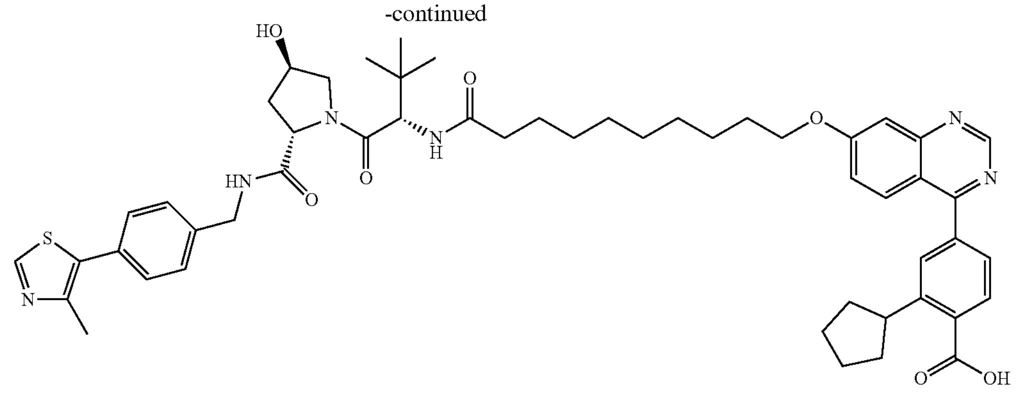

3

Step 1. Synthesis of tert-butyl 2-cyclopentyl-4-[7-(10-ethoxy-10-oxo-decoxy)quinazolin-4-yl]benzoate

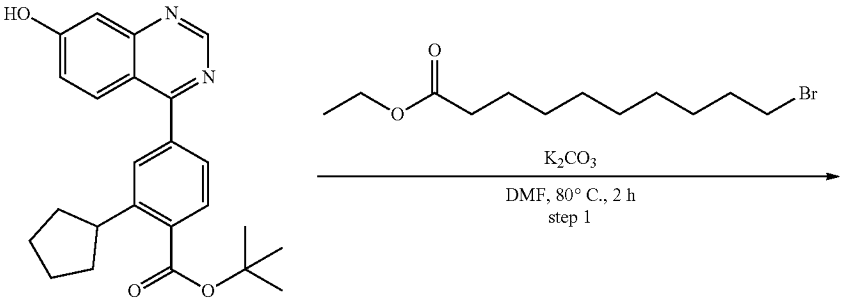

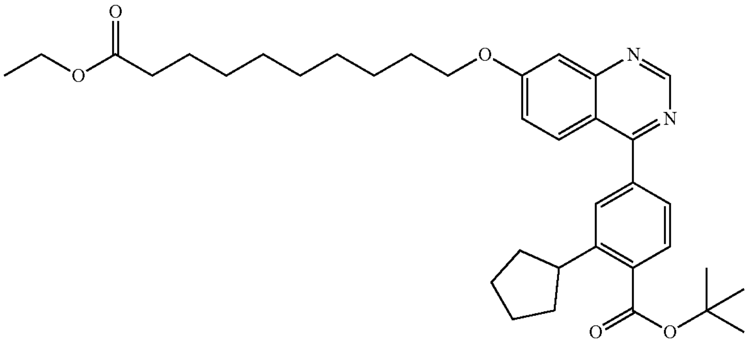

To a stirred solution of tert-butyl 2-cyclopentyl-4-(7-hydroxyquinazolin-4-yl)benzoate (1000 mg, 2.56 mmol) in DMF (10 mL) were added $K_2CO_3$ (1060 mg, 7.68 mmol) and ethyl 10-bromodecanoate (857 mg, 3.07 mmol) at room temperature and then stirred at 80° C. for 2 h. The reaction mixture was quenched with water and extracted with EA. The extracts were combined and washed with brine, dried over sodium sulfate, filtered and concentrated. The crude product was purified by silica gel column chromatography (PE/EA, 1:1) to obtain tert-butyl 2-cyclopentyl-4-[7-(10-ethoxy-10-oxo-decoxy)quinazolin-4-yl]benzoate (1400 mg, 2.38 mmol, 92.8% yield) as a light-yellow oil. MS: m/z: Calc'd for $C_{36}H_{48}N_2O_5$ $[M+H]^+$ 589, found $[M+H]^+$ 589.

Step 2. Synthesis of 10-[4-(4-tert-butoxycarbonyl-3-cyclopentyl-phenyl)quinazolin-7-yl]oxydecanoic acid

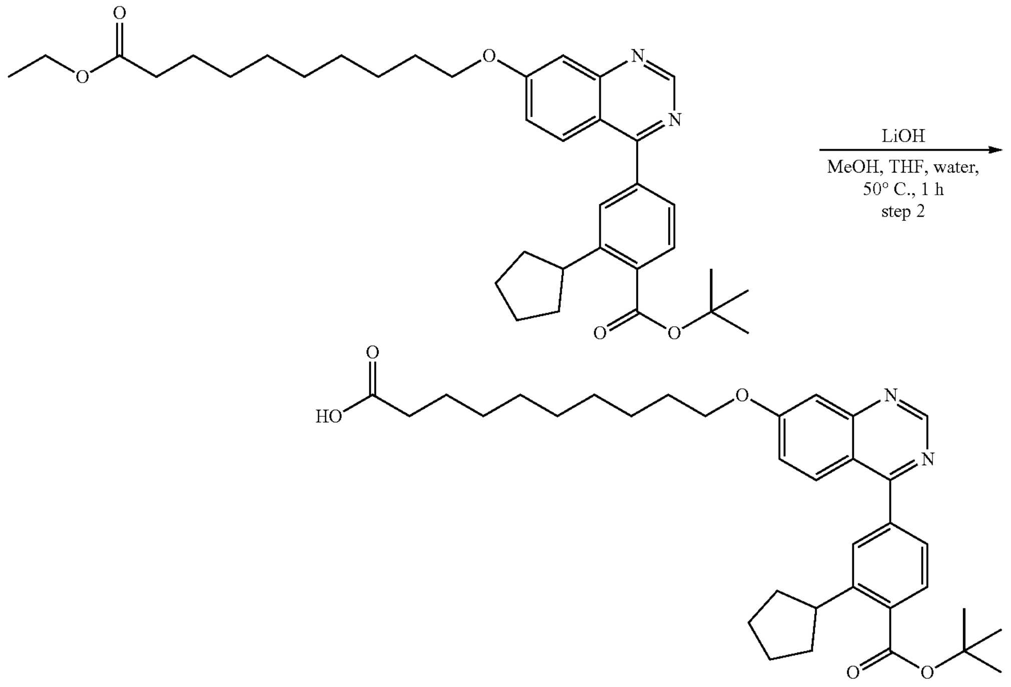

To a stirred solution of tert-butyl 2-cyclopentyl-4-[7-(10-ethoxy-10-oxo-decoxy)quinazolin-4-yl]benzoate (1390 mg, 2.36 mmol) in methanol (5 mL), THF (5 mL) and water (2 mL) was added LiOH (113 mg, 4.72 mmol) at room temperature and the reaction mixture was stirred at 50° C. for 1 h. The reaction mixture was concentrated, and then diluted with water, pH value was adjusted to 4-5 with 1.0 N HCl, and filtered to obtain 10-[4-(4-tert-butoxycarbonyl-3-cyclopentyl-phenyl)quinazolin-7-yl]oxydecanoic acid (1300 mg, 2.32 mmol, 98.2% yield) as a white solid. MS: m/z: Calc'd for $C_{34}H_{44}N_2O_5$ $[M+H]^+$ 561, found $[M+H]^+$ 561.

Step 3. Synthesis of tert-butyl 2-cyclopentyl-4-[7-[10-oxo-10-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]decoxy]quinazolin-4-yl]benzoate

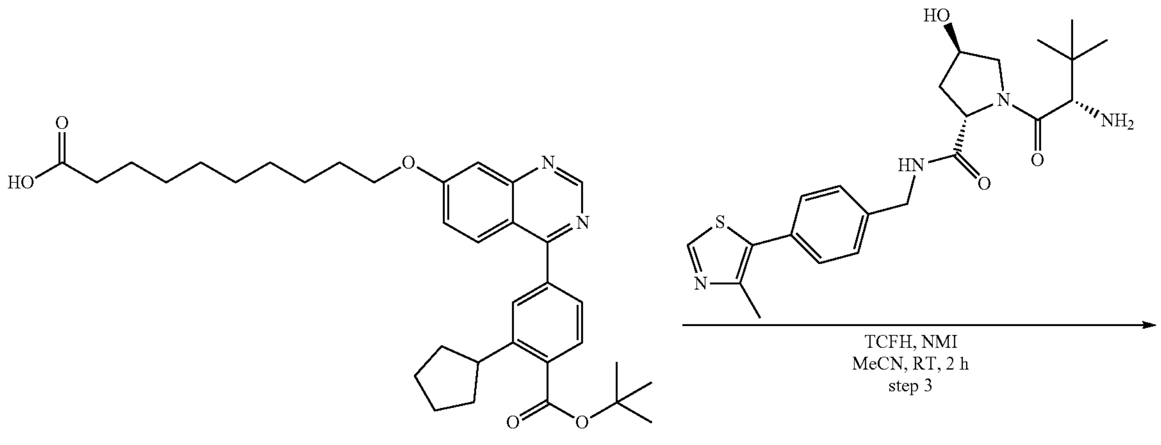

-continued

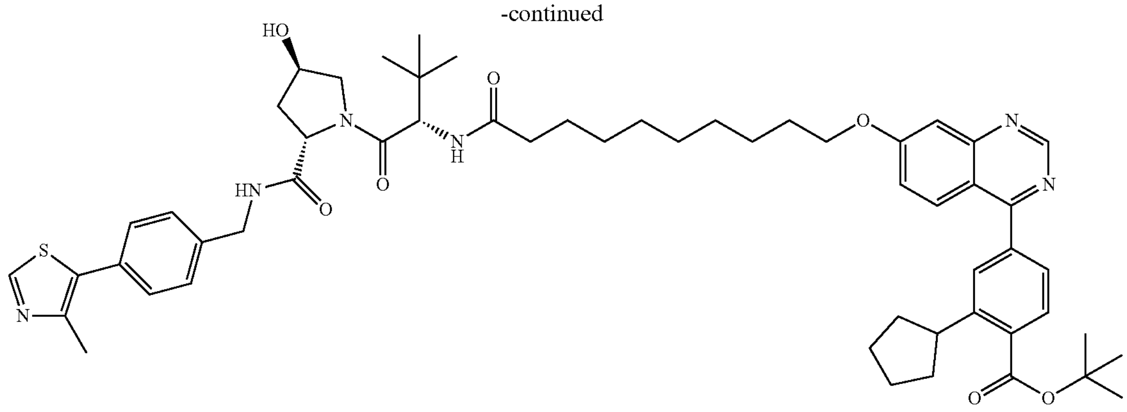

To a solution of 10-[4-(4-tert-butoxycarbonyl-3-cyclopentyl-phenyl)quinazolin-7-yl]oxydecanoic acid (1280 mg, 2.28 mmol) in dry MeCN (20 mL) were added TCFH (1281 mg, 4.57 mmol), NMI (0.9 mL, 11.41 mmol) and rac-(2S,4R)-4-hydroxy-N-[[4-(4-methylthiazol-5-yl)phenyl]methyl]-1-[rac-(2S)-2-amino-3,3-dimethyl-butanoyl]pyrrolidine-2-carboxamide (983 mg, 2.28 mmol), and then the reaction mixture was stirred at room temperature for 2 h. The resulting mixture was concentrated. The crude was purified by reverse flash (0.05% TFA/MeCN) to obtain tert-butyl 2-cyclopentyl-4-[7-[10-oxo-10-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]decoxy]quinazolin-4-yl]benzoate (1500 mg, 1.54 mmol, 67.5% yield) as a white solid. MS: m/z: Calc'd for $C_{56}H_{72}N_6O_7S$ $[M+H]^+$ 973; Found, 973 $[M+H]^+$.

Step 4. Synthesis of 2-cyclopentyl-4-[7-[10-oxo-10-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]decoxy]quinazolin-4-yl]benzoic acid (3)

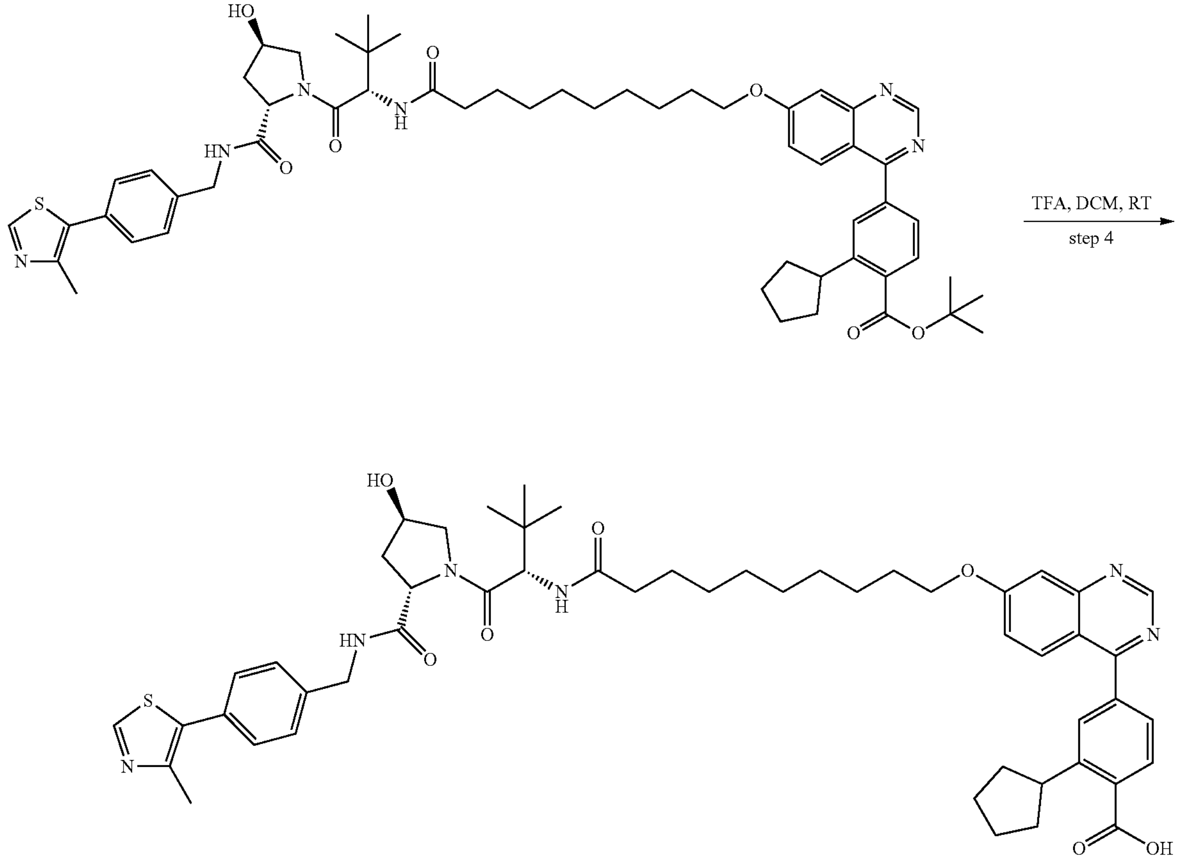

To a stirred solution of tert-butyl 2-cyclopentyl-4-[7-[10-oxo-10-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]decoxy]quinazolin-4-yl] benzoate (1490 mg, 1.53 mmol) in DCM (8 mL) was added TFA (4 mL, 49.11 mmol) at 0° C., and stirred at room temperature for 3 h. The reaction mixture was concentrated to dryness in vacuum. The crude product was first purified by reverse flash column chromatography and then purified by HP-FLASH chromatography to obtain 2-cyclopentyl-4-[7-[10-oxo-10-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]decoxy] quinazolin-4-yl]benzoic acid (696 mg, 0.75 mmol, 49.5% yield) as a white solid.

MS: m/z: Calc'd for $C_{52}H_{64}N_6O_7S$ $[M+H]^+$ 917; Found, 917 $[M+H]^+$.

$^1H$ NMR (300 MHz, Methanol-$d_4$) δ 9.15 (d, J=1.4 Hz, 1H), 8.87 (d, J=1.3 Hz, 1H), 7.98 (dd, J=9.2, 1.7 Hz, 1H), 7.86 (m, 1H), 7.73 (m, 1H), 7.57 (m, 1H), 7.52-7.28 (m, 6H), 4.70-4.50 (m, 4H), 4.36 (m, 1H), 4.27-4.17 (m, 2H), 3.92-3.76 (m, 3H), 2.48 (s, 3H), 2.40-2.02 (m, 6H), 1.95-1.82 (m, 4H), 1.80-1.50 (m, 8H), 1.38 (m, 8H), 1.05 (s, 9H).

HP-FLASH conditions. Column: Ultimate XB-C18 Column, 50*250 mm, 10 μm; Mobile Phase A: Water (10 mmol/L $NH_4HCO_3$); Mobile Phase B: ACN; Flow rate: 90 mL/min; Gradient: 10 B to 50 B in 35 min; 254/210 nm.

Example S7: Synthesis of Compound 2 (n=8)

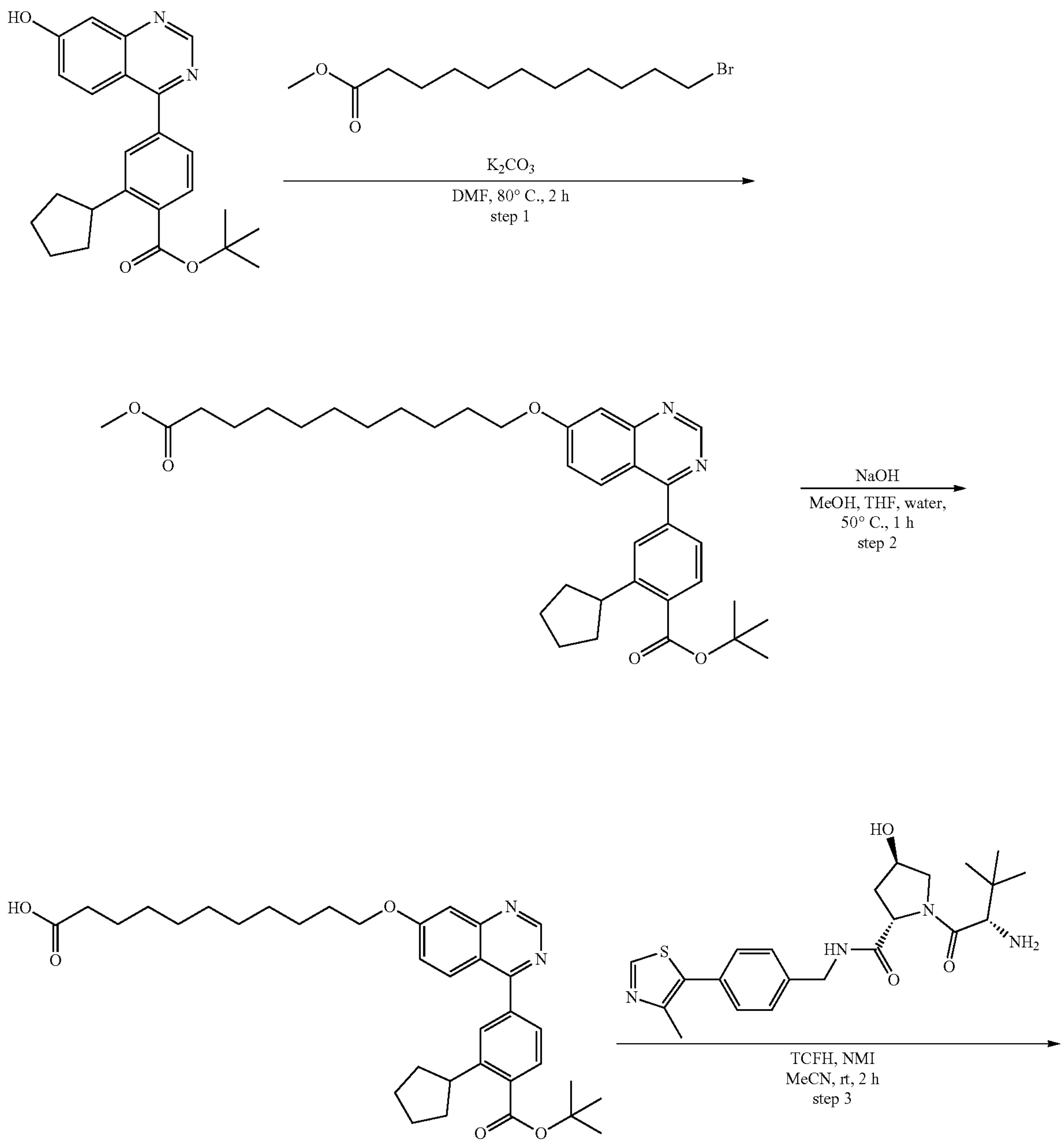

-continued
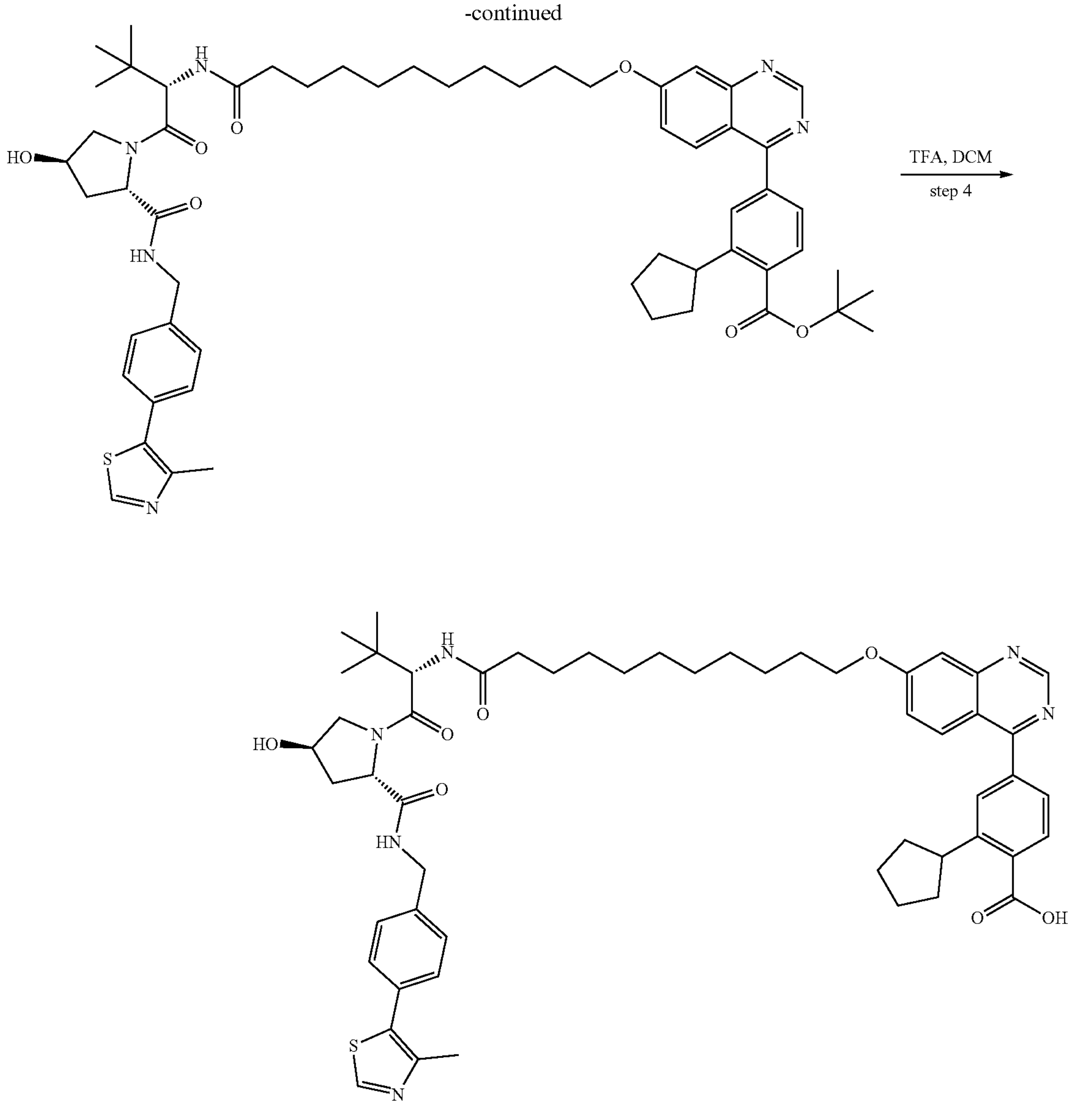
2
Step 1. Synthesis of tert-butyl 2-cyclopentyl-4-[7-(11-methoxy-11-oxo-undecoxy)quinazolin-4-yl]benzoate
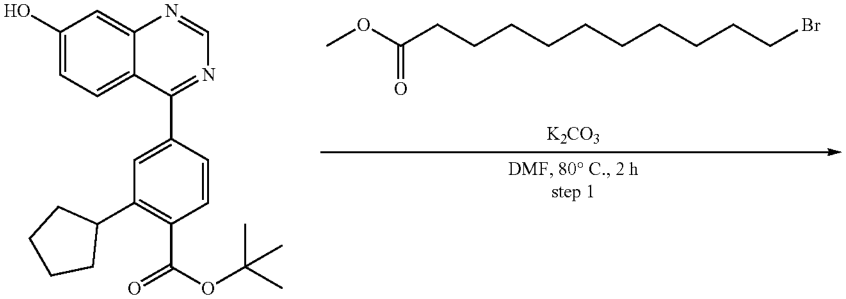

-continued

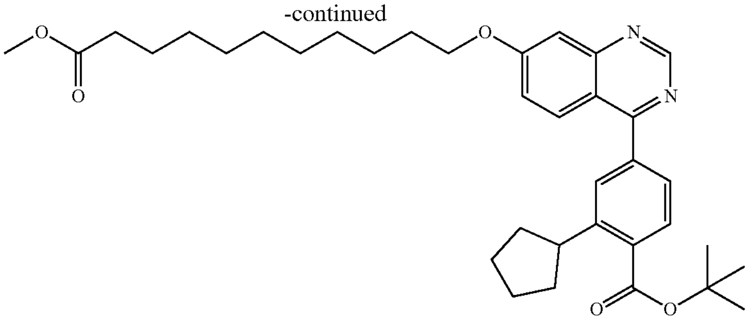

To a stirred solution of tert-butyl 2-cyclopentyl-4-(7-hydroxyquinazolin-4-yl)benzoate (200 mg, 0.51 mmol) in DMF (5 mL) was added $K_2CO_3$ (212 mg, 1.54 mmol) and methyl 11-bromoundecanoate (171 mg, 0.61 mmol) at room temperature, and the resulting solution was stirred at 80° C. for 2 h. The reaction mixture was diluted with EA and washed with brine. The organic layer was dried over sodium sulfate, filtered, and concentrated. The crude was purified by silica gel column chromatography to obtain tert-butyl 2-cyclopentyl-4-[7-(11-methoxy-11-oxo-undecoxy)quinazolin-4-yl]benzoate (270 mg, 89.5% yield) as a colorless oil. MS: m/z: Calc'd for $C_{36}H_{48}N_2O_5$ $[M+H]^+$ 589; Found, 589.35 $[M+H]^+$.

Step 2. Synthesis of 11-[4-(4-tert-butoxycarbonyl-3-cyclopentyl-phenyl)quinazolin-7-yl]oxyundecanoic acid

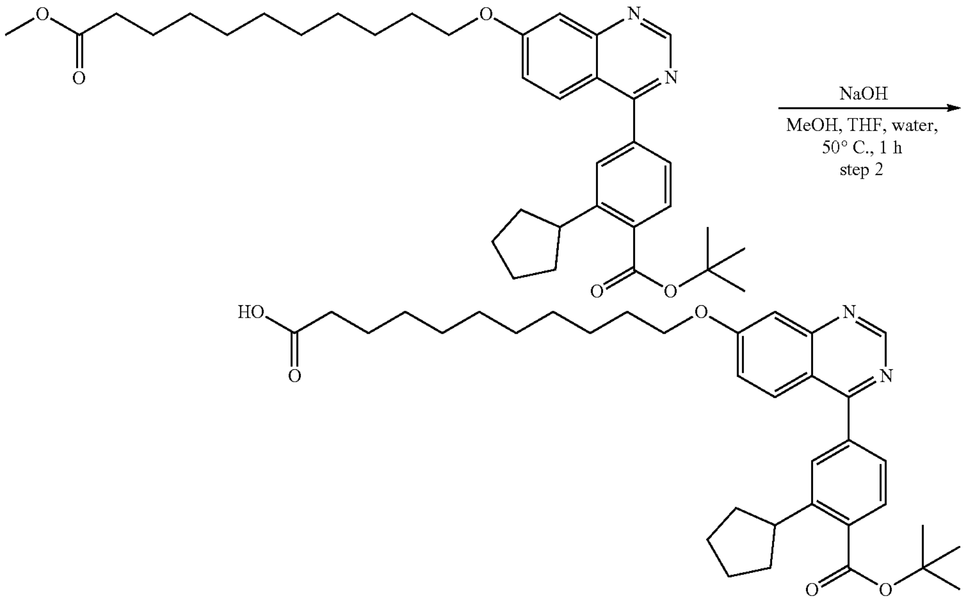

To a stirred solution of tert-butyl 2-cyclopentyl-4-[7-(11-methoxy-11-oxo-undecoxy)quinazolin-4-yl]benzoate (260 mg, 0.44 mmol) in methanol (3 mL), THF (3 mL) and water (1.2 mL) was added NaOH (53 mg, 1.32 mmol) at room temperature. The resulting mixture was stirred at 50° C. for 1 h. The reaction mixture was concentrated, and then diluted with water, the pH value was adjusted to 3-4 with 1.0 N HCl, and the resulting precipitate filtered. The obtained solid was further purified by reverse flash chromatography to obtain 11-[4-(4-tert-butoxycarbonyl-3-cyclopentyl-phenyl)quinazolin-7-yl]oxyundecanoic acid (200 mg, 78.8% yield) as a white solid. MS: m/z: Calc'd for $C_{35}H_{46}N_2O_5$ $[M+H]^+$ 575; Found, 575.40 $[M+H]^+$.

Step 3. Synthesis of tert-butyl 2-cyclopentyl-4-[7-[11-oxo-11-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]undecoxy]quinazolin-4-yl]benzoate

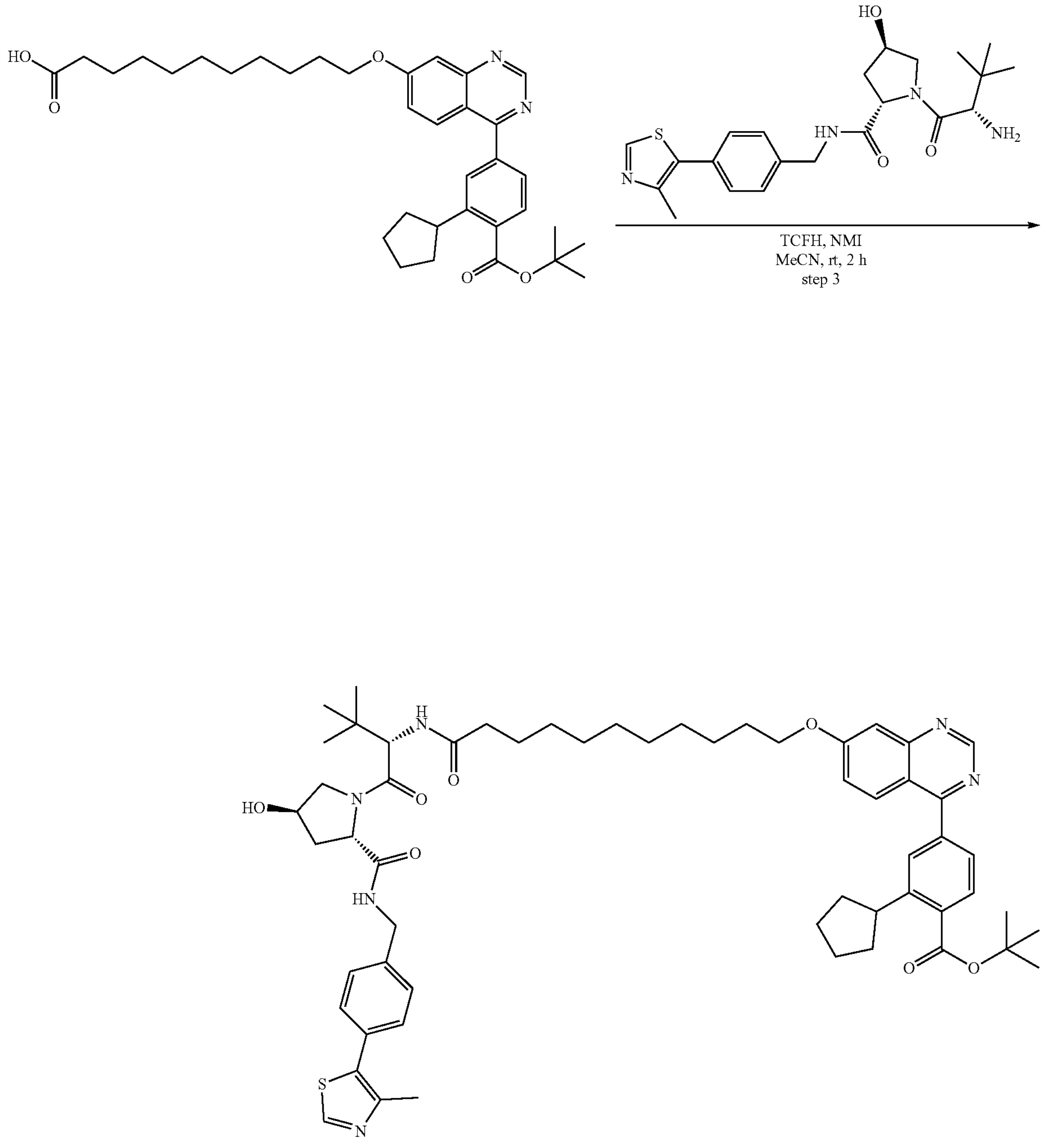

To a solution of 11-[4-(4-tert-butoxycarbonyl-3-cyclopentyl-phenyl)quinazolin-7-yl]oxyundecanoic acid (90 mg, 0.16 mmol) in dry MeCN (4 mL) was added TCFH (88 mg, 0.31 mmol), NMI (0.06 mL, 0.78 mmol) and rac-(2S,4R)-4-hydroxy-N-[[4-(4-methylthiazol-5-yl)phenyl]methyl]-1-[rac-(2S)-2-amino-3,3-dimethyl-butanoyl]pyrrolidine-2-carboxamide (67 mg, 0.16 mmol). The resulting mixture was stirred at room temperature for 2 h. The reaction mixture was concentrated. The crude product was purified by reverse flash chromatography (0.5% TFA/MeCN) to obtain tert-butyl 2-cyclopentyl-4-[7-[11-oxo-11-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]undecoxy]quinazolin-4-yl]benzoate (100 mg, 64.7% yield) as a white solid. MS: m/z: Calc'd for $C_{57}H_{74}N_6O_7$ S $[M+H]^+$ 988; Found, 988 $[M+H]^+$.

Step 4. Synthesis of 2-cyclopentyl-4-[7-[11-oxo-11-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]undecoxy]quinazolin-4-yl]benzoic acid (2)

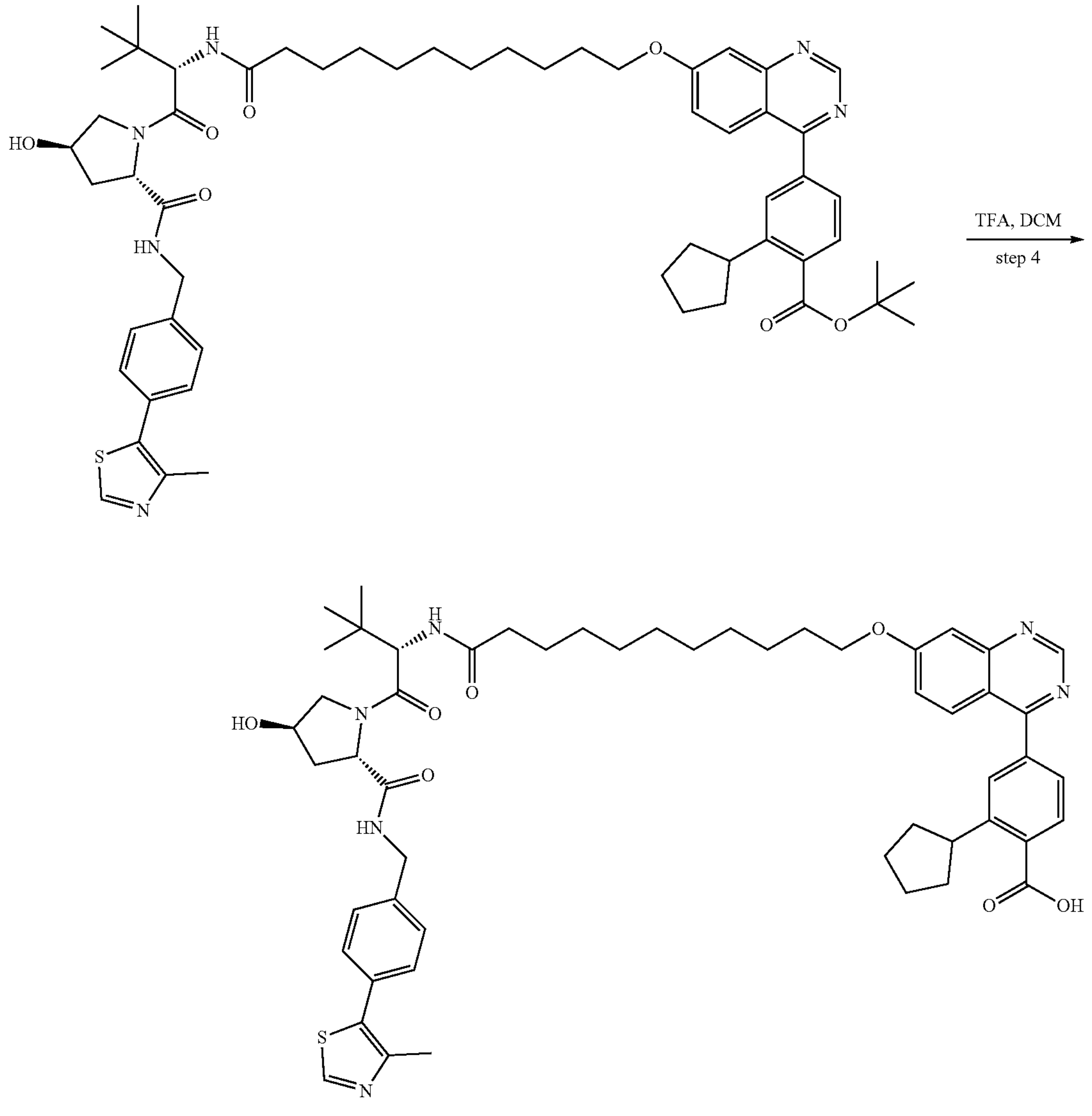

2

To a stirred solution of tert-butyl 2-cyclopentyl-4-[7-[11-oxo-11-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]undecoxy]quinazolin-4-yl]benzoate (90 mg, 0.09 mmol) in DCM (2 mL) was added TFA (1 mL, 12.28 mmol) at room temperature, and the resulting mixture was stirred for 1 h. The reaction mixture was concentrated to dryness under vacuum. The crude product was purified by Prep-HPLC to obtain 2-cyclopentyl-4-[7-[11-oxo-11-[[rac-(1S)-2,2-dimethyl-1-[rac-(2S,4R)-4-hydroxy-2-[[4-(4-methylthiazol-5-yl)phenyl]methylcarbamoyl]pyrrolidine-1-carbonyl]propyl]amino]undecoxy]quinazolin-4-yl]benzoic acid (2) (50.6 mg, 58.8% yield) as a white solid.

MS: m/z: Calc'd for $C_{53}H_{66}N_6O_7$ S $[M+H]^+$ 931; Found, 931 $[M+H]^+$.

$^1$H NMR (400 MHz, DMSO-$d_6$) δ 9.24 (s, 1H), 8.99 (s, 1H), 8.57 (t, J=6.1 Hz, 1H), 7.93-7.77 (m, 4H), 7.62 (dd, J=7.9, 1.7 Hz, 1H), 7.47-7.32 (m, 6H), 4.58-4.51 (m, 1H), 4.43 (m, 2H), 4.35 (s, 1H), 4.26-4.17 (m, 4H), 3.82-3.74 (m, 1H), 3.71-3.60 (m, 2H), 2.44 (s, 3H), 2.26 (m, 1H), 2.07 (m, 4H), 1.90 (m, 1H), 1.84-1.75 (m, 4H), 1.63 (m, 4H), 1.48-1.34 (m, 4H), 1.26 (m, 10H), 0.93 (s, 9H).

Prep-HPLC conditions: Column: X Select CSH Prep C18 OBD Column, 5 μm, 19*150 mm; Mobile Phase A: water (0.05% TFA), Mobile Phase B: ACN; Flow rate: 25 mL/min; Gradient: 55% B to 82% B in 7 min; 254/210 nm; Rtl: 6.87.

Example S8. Synthesis of Compound 1 (n=9)
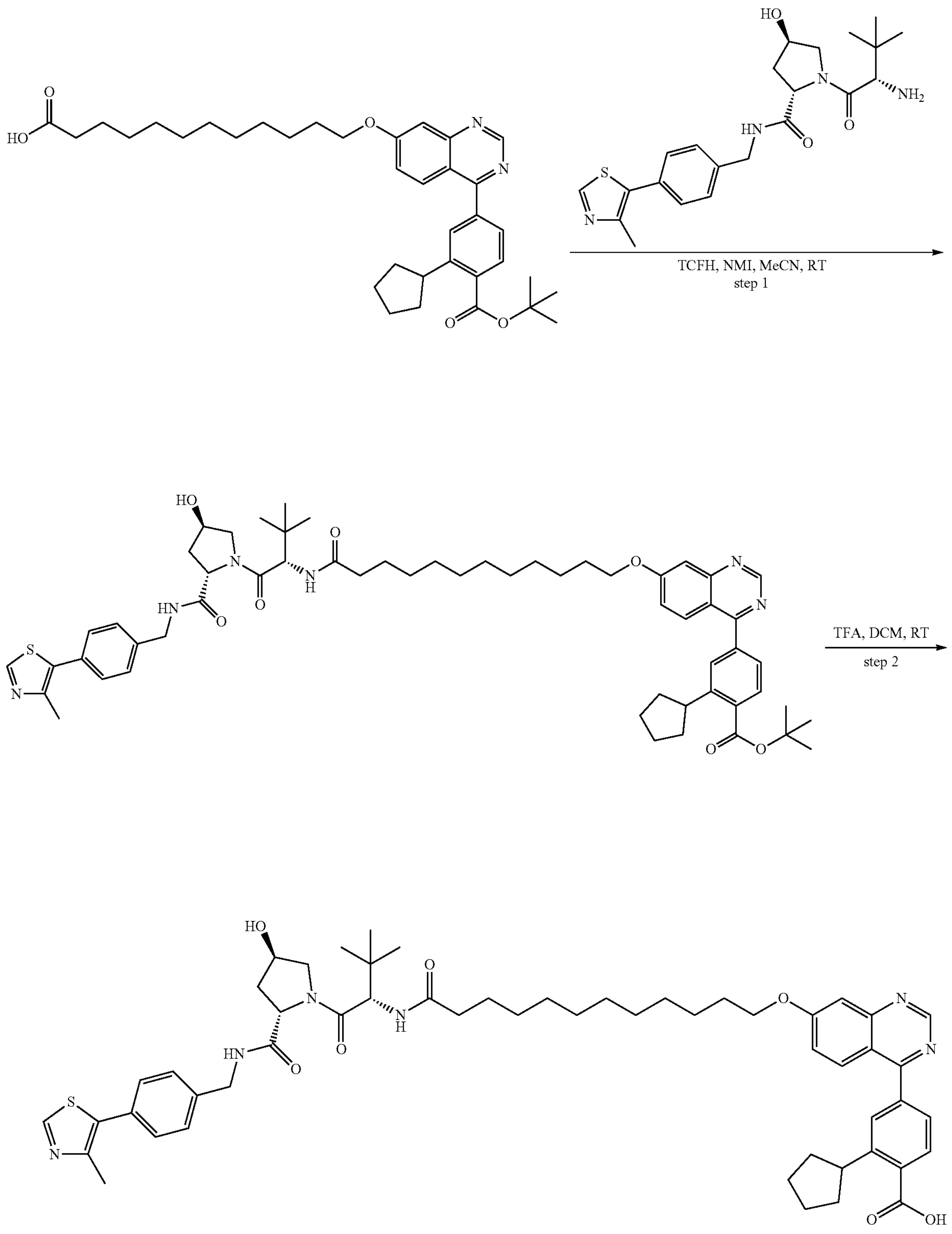
1

Step 1. Synthesis of tert-butyl 2-cyclopentyl-4-[7-[12-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-12-oxo-dodecoxy]quinazolin-4-yl]benzoate

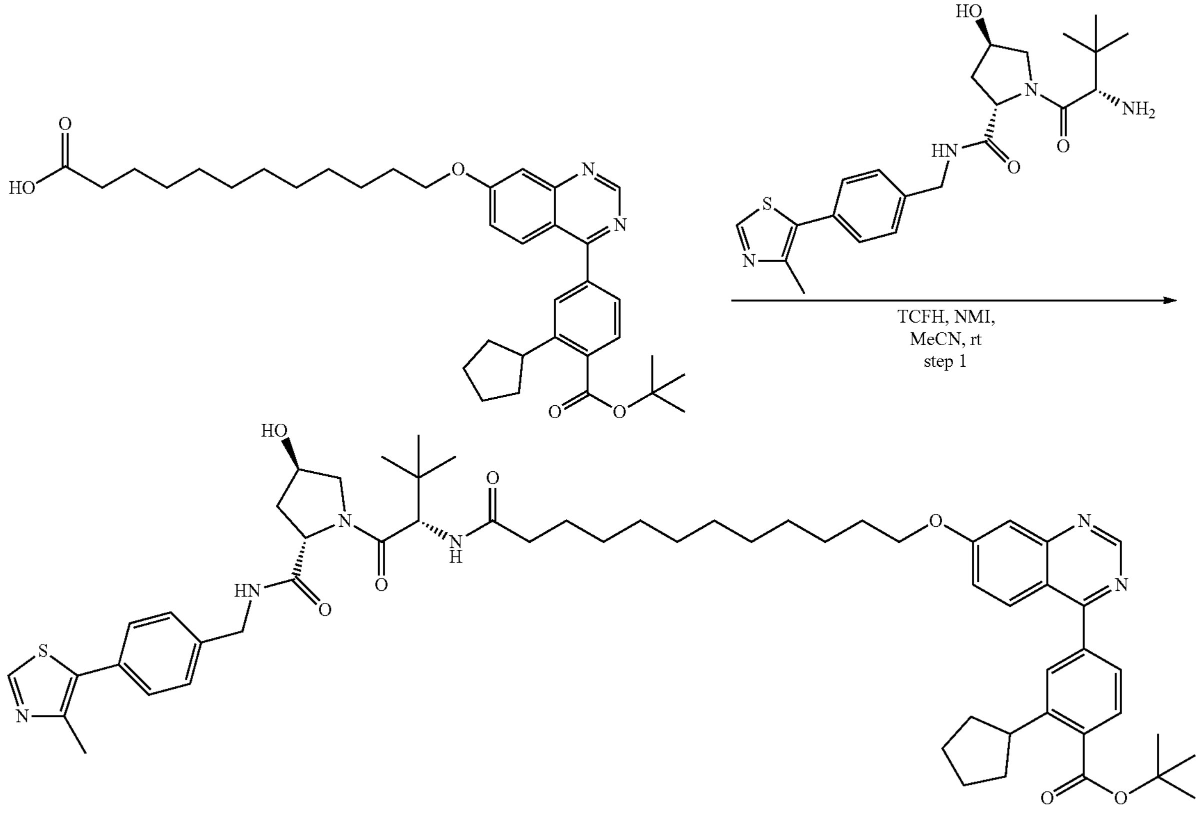

A mixture of 12-[4-(4-tert-butoxycarbonyl-3-cyclopentyl-phenyl)quinazolin-7-yl]oxydodecanoic acid (75 mg, 0.13 mmol), (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (I-1 from Example S1) (60.33 mg, 0.14 mmol), TCFH (71.48 mg, 0.25 mmol) and NMI (0.06 mL, 0.76 mmol) in MeCN (5 mL) was stirred at room temperature for 2 h. LCMS showed the reaction was completed. The solvent was evaporated under vacuum, and the crude product was purified by Prep-HPLC to obtain tert-butyl 2-cyclopentyl-4-[7-[12-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-12-oxo-dodecoxy]quinazolin-4-yl]benzoate (90 mg, 70.56% yield) as a brown solid. MS: m/z: Calc'd for $C_{58}H_{76}N_6O_7S$ $[M+H]^+$ 1001, found 1001 $[M+H]^+$.

Step 2. Synthesis of 2-cyclopentyl-4-[7-[12-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-12-oxo-dodecoxy]quinazolin-4-yl]benzoic acid (1)

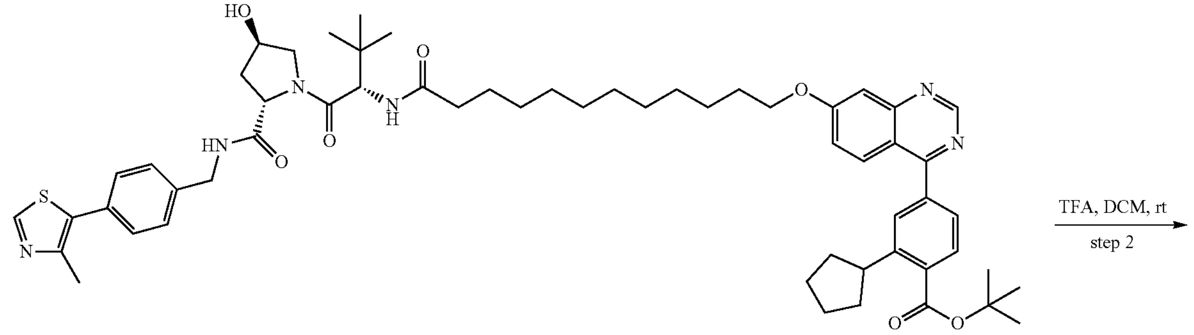

-continued

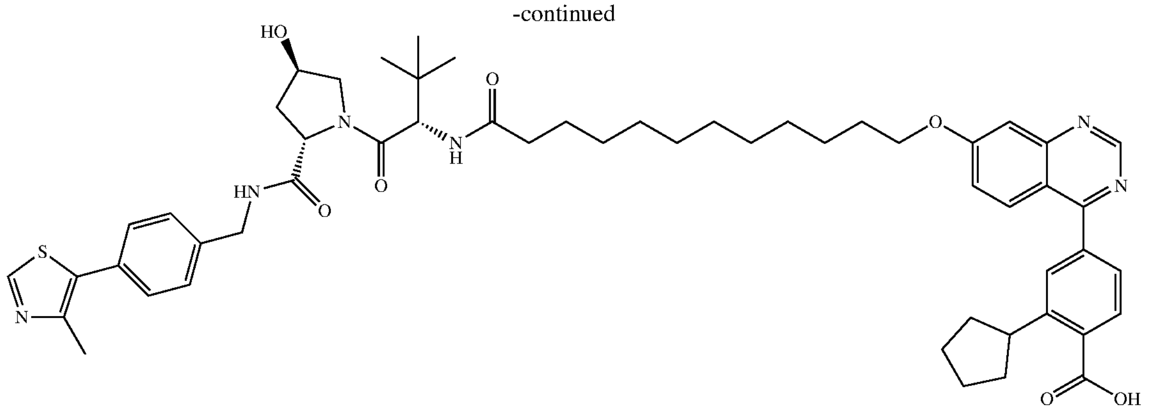

1

To a solution of tert-butyl 2-cyclopentyl-4-[7-[12-[[(1S)-1-[(2S,4R)-4-hydroxy-2-[[4-(4-methylthiazol-5-yl)phenyl] methylcarbamoyl]pyrrolidine-1-carbonyl]-2,2-dimethyl-propyl]amino]-12-oxo-dodecoxy]quinazolin-4-yl]benzoate (80. mg, 0.0800 mmol) in DCM (10 mL) was added TFA (4.5 mL) dropwise at 0° C. The resulting mixture was stirred at room temperature for 2 h. LCMS showed the reaction was completed. After removing solvents, the crude product was purified by Prep-HPLC to obtain 2-cyclopentyl-4-[7-[12-[[(1S)-1-[(2S,4R)-4-hydroxy-2-[[4-(4-methylthiazol-5-yl) phenyl]methylcarbamoyl]pyrrolidine-1-carbonyl]-2,2-dimethyl-propyl]amino]-12-oxo-dodecoxy]quinazolin-4-yl] benzoic acid (1) (18.2 mg, 23.86% yield) as a white solid.

MS: m/z: Calc'd for $C_{54}H_{68}N_6O_7S$ $[M+H]^+$ 945.35; Found, 945 $[M+H]^+$.

$^1H$ NMR (400 MHz, DMSO-$d_6$) δ 9.23 (s, 1H), 8.97 (s, 1H), 8.55 (t, J=6.2 Hz, 1H), 7.92 (d, J=9.3 Hz, 1H), 7.86-7.78 (m, 2H), 7.75 (d, J=1.7 Hz, 1H), 7.61 (dd, J=7.9, 1.7 Hz, 1H), 7.45-7.33 (m, 6H), 5.11 (s, 1H), 4.54 (d, J=9.4 Hz, 1H), 4.48-4.38 (m, 2H), 4.34 (s, 1H), 4.25-4.17 (m, 3H), 3.82-3.73 (m, 1H), 3.71-3.59 (m, 2H), 2.44 (s, 3H), 2.29-2.22 (m, 1H), 2.14-2.01 (m, 4H), 1.93-1.85 (m, 1H), 1.79 (q, J=5.9, 5.0 Hz, 4H), 1.69-1.56 (m, 4H), 1.53-1.41 (m, 4H), 1.36-1.19 (m, 12H), 0.92 (s, 9H).

Prep-reverse flash conditions: [Column: XBridge Shield RP18 OBD Column, 30*150 mm, 5 μm; Mobile Phase A: water (10 mmol/L $NH_4HCO_3$+0.1% $NH_3 \cdot H_2O$), Mobile Phase B: ACN; Flow rate: 60 mL/min; Gradient: 20% B to 49% B in 7 min; 254/220 nm.]

BIOLOGICAL EXAMPLES

Example B1. Determination of Potency and Efficiency of Test Compounds to Degrade Stably Expressed Enhanced ProLabel (ePL)-Tagged CAMKK2 in 293T Cells CAMKK2 degradation assay cell line 293T was generated via lentiviral infection with pCDH-ePL-CAMKK2, and stable integrants were selected with 1 μg/mL Puromycin. Cells were dispensed into 384 well plates pre-spotted with serial diluted test compounds. After 24 h incubation, degradation was terminated by the addition of DiscoverX InCELL Hunter Detection reagent.

Fifty nanoliters of test compound in DMSO was dispensed with an acoustic dispenser (ATS acoustic transfer system from EDC Biosystems) into 384 well plate (Corning #3570) in 10 point 3-fold serial dilutions starting at 5 mM. Twenty-five microliters 400 ePL-CAMKK2 293T cells in media (RPMI 1640+10% Heat Inactivated FBS) were dispensed to each well. Assay plates were incubated at 37° C. with 5% $CO_2$ for 24 hours. Plates were kept at room temperature for 30 min, after which 25 μL of the InCELL Hunter Detection Reagent Working Solution was added (catalog number 96-0002, DiscoverX, Fremont, CA). After plates were incubated at room temperature for 30 min, protected from light, luminescence was read on a PHER-Astar reader (BMG LABTECH, Cary, N.C.). Data was normalized and fit using Activity Base (IDBS, Alameda, Calif.) as described below.

Percentage of CAMKK2 level (PoC) was determined using the luminescent signal in compound-treated wells, normalized to that of DMSO control and fully inhibited luciferase activity control. A Four Parameter Logistic Model (Sigmoidal Dose-Response Model, equation 1) was used to determine the compound's $EC_{50}$ and degradation $Y_{min}$.

$$PoC = A + (100 - A)/(1 + (C/x)^D) \quad \text{(equation 1)}$$

where C is CAMKK2 degradation potency $EC_{50}$, D is the correlation coefficient, A is the lower limit reported as $Y_{min}$. $Y_{min}$ and $EC_{50}$ were used to characterize compound-mediated CAMKK2 degradation efficiency.

Results are shown in Table 2, where $Y_{min}$ is the minimum % protein remaining, and $EC_{50}$ is the concentration that elicits 50% decrease in protein levels relative to $Y_{min}$.

TABLE 2

| Compound No. | (ePL) HEK293 24 h CAMKK2 $Y_{min}$(%) | (ePL) HEK293 24 h CAMKK2 $EC_{50}$ (mM) |
|---|---|---|
| 1 | 43 | 1.26 |
| 2 | 37 | 1.62 |
| 3 | 24 | 0.841 |
| 4 | 19 | 1.49 |
| 5 | 32 | 2.44 |
| 6 | 42 | 1.93 |

Although the present invention has been described in some detail by way of illustration and example for purposes of clarity of understanding, the descriptions and examples should not be construed as limiting the scope of the invention. The disclosures of all patent and scientific literature cited herein are expressly incorporated herein in their entirety by reference.

The invention claimed is:

1. A compound of Formula (Ia):

(Ia)

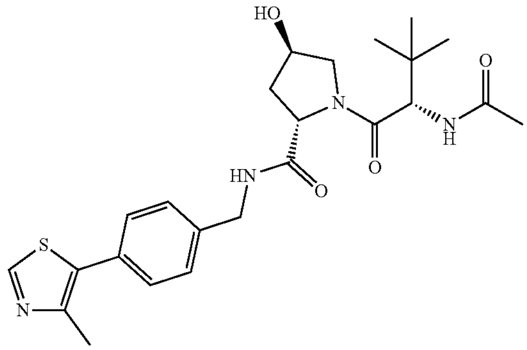

-continued

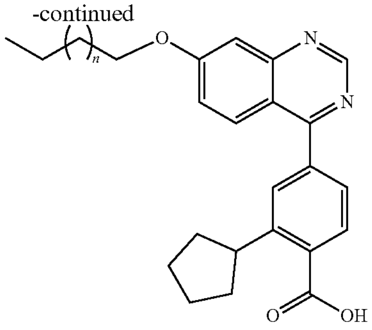

or a pharmaceutically acceptable salt thereof, wherein:
n is 2-10.

2. The compound of claim 1, or a pharmaceutically acceptable salt thereof, wherein:
n is 4.

3. The compound of claim 1, or a pharmaceutically acceptable salt thereof, wherein:
n is 5.

4. The compound of claim 1, or a pharmaceutically acceptable salt thereof, wherein:
n is 6.

5. The compound of claim 1, or a pharmaceutically acceptable salt thereof, wherein:
n is 7.

6. The compound of claim 1, or a pharmaceutically acceptable salt thereof, wherein:
n is 8.

7. The compound of claim 1, or a pharmaceutically acceptable salt thereof, wherein:
n is 9.

8. A compound selected from

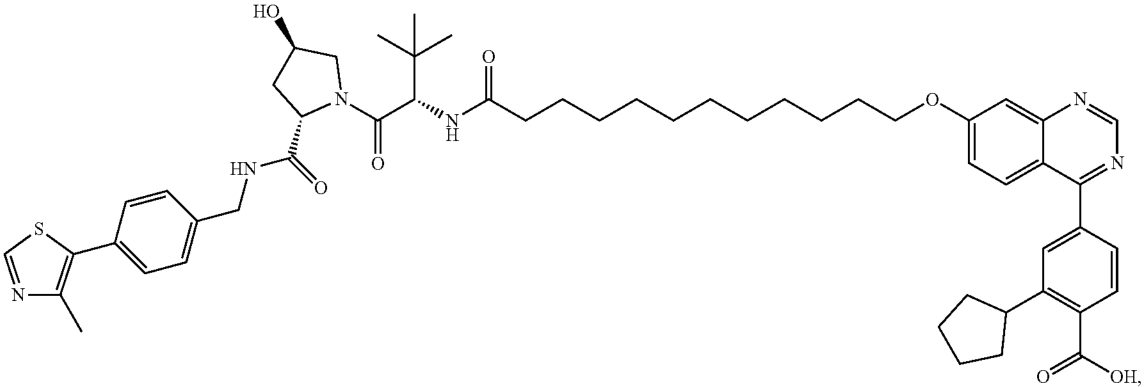
,

-continued
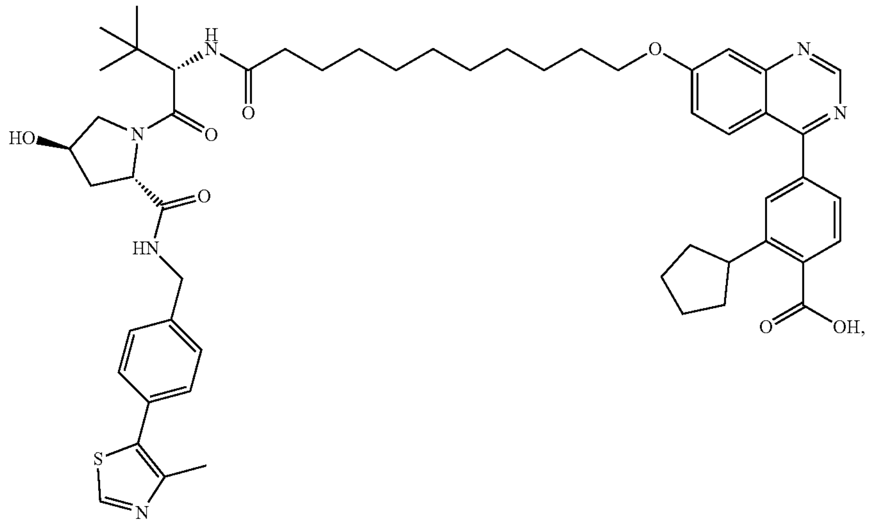
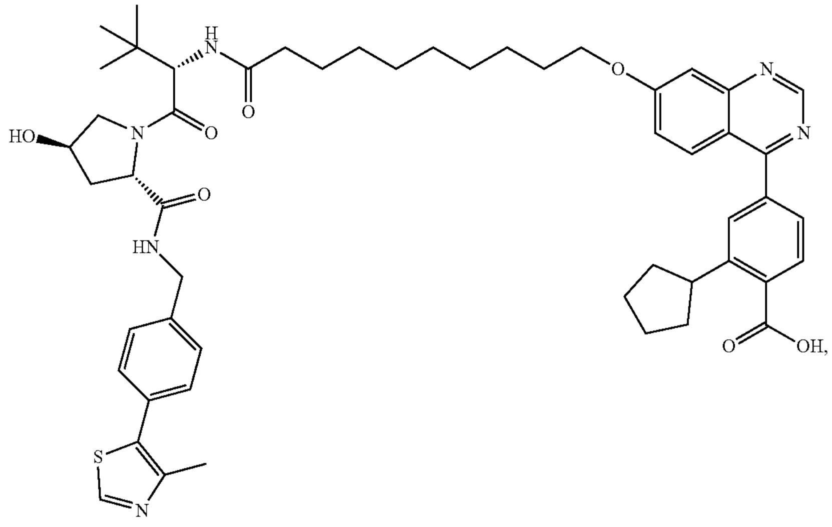
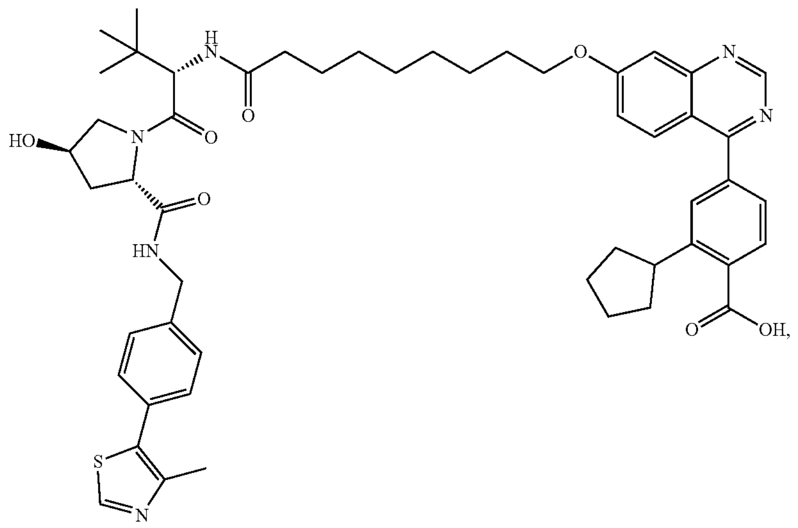

-continued

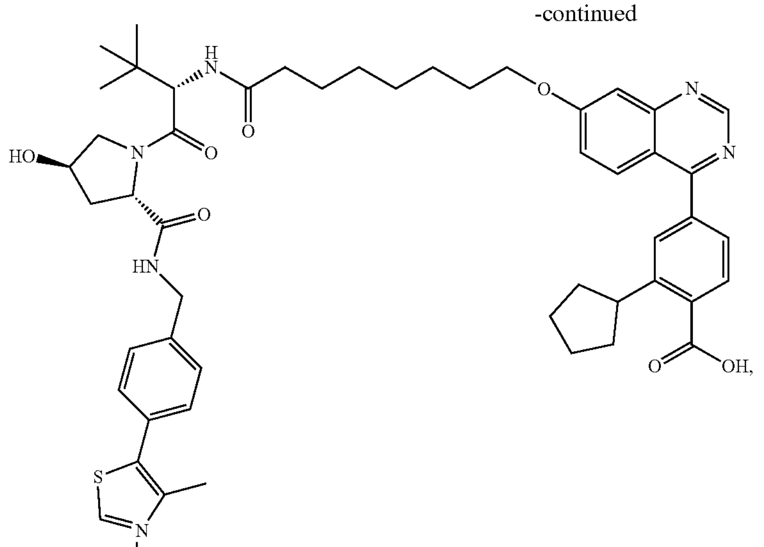

and

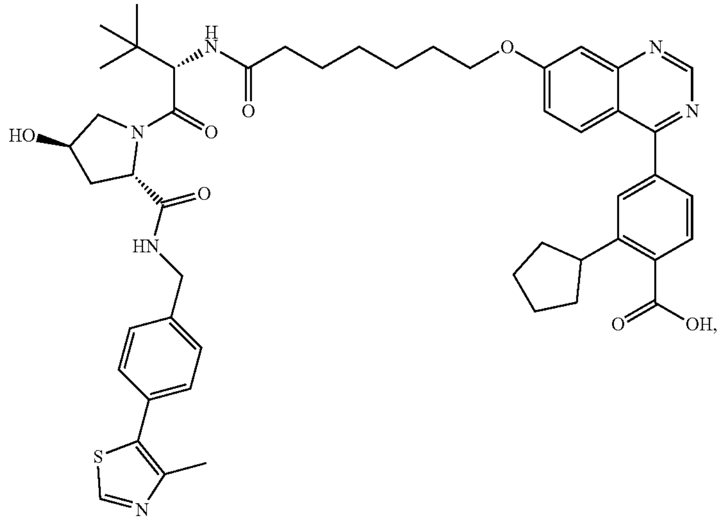

or a pharmaceutically acceptable salt thereof.

9. A pharmaceutical composition comprising the compound of claim 1, or a pharmaceutically acceptable salt thereof, and a pharmaceutically acceptable excipient.

10. A method of treating a cancer in a subject in need thereof, comprising administering to the subject an effective amount of the compound of claim 1, or a pharmaceutically acceptable salt thereof, wherein the cancer is acute myeloid leukemia (AML) acute lymphoblastic leukemia (ALL), small cell lung cancer (SCLC), non-small cell lung cancer (NSCLC), neuroblastoma, small round blue cell tumors, glioblastoma, glioma, prostate cancer, breast cancer, bladder cancer, lung cancer, or melanoma.

11. A pharmaceutical composition comprising the compound of claim 8, or a pharmaceutically acceptable salt thereof, and a pharmaceutically acceptable excipient.

12. A method of treating a cancer in a subject in need thereof, comprising administering to the subject an effective amount of the compound of claim 8, or a pharmaceutically acceptable salt thereof, wherein the cancer is acute myeloid leukemia (AML), acute lymphoblastic leukemia (ALL), small cell lung cancer (SCLC), non-small cell lung cancer (NSCLC), neuroblastoma, small round blue cell tumors, glioblastoma, glioma, prostate cancer, breast cancer, bladder cancer, lung cancer, or melanoma.

* * * * *